United States Patent
Riggs-Sauthier et al.

(10) Patent No.: US 9,421,275 B2
(45) Date of Patent: *Aug. 23, 2016

(54) OLIGOMER-CALCIMIMETIC CONJUGATES AND RELATED COMPUNDS

(71) Applicant: Nektar Therapeutics, San Francisco, CA (US)

(72) Inventors: Jennifer Riggs-Sauthier, San Francisco, CA (US); Lin Cheng, Millbrae, CA (US); David Martin, San Francisco, CA (US)

(73) Assignee: Nektar Therapeutics, San Francisco, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/223,572

(22) Filed: Mar. 24, 2014

(65) Prior Publication Data

US 2014/0323565 A1    Oct. 30, 2014

Related U.S. Application Data

(63) Continuation of application No. 13/433,100, filed on Mar. 28, 2012, now Pat. No. 8,722,732, which is a continuation-in-part of application No. PCT/US2010/050761, filed on Sep. 29, 2010.

(60) Provisional application No. 61/246,931, filed on Sep. 29, 2009, provisional application No. 61/597,663, filed on Feb. 10, 2012.

(51) Int. Cl.
| | |
|---|---|
| *A61P 5/10* | (2006.01) |
| *A61K 31/137* | (2006.01) |
| *A61K 31/27* | (2006.01) |
| *C07C 271/14* | (2006.01) |
| *A61K 47/48* | (2006.01) |
| *C07C 211/30* | (2006.01) |

(52) U.S. Cl.
CPC ......... *A61K 47/48215* (2013.01); *C07C 211/30* (2013.01); *C07C 271/14* (2013.01); *C07B 2200/11* (2013.01)

(58) Field of Classification Search
USPC ...................... 514/481, 654; 560/28; 564/374
See application file for complete search history.

(56) References Cited

U.S. PATENT DOCUMENTS

| | | | |
|---|---|---|---|
| 4,966,988 A | 10/1990 | Schinski et al. | |
| 5,648,541 A | 7/1997 | VanWagenen et al. | |
| 5,672,662 A | 9/1997 | Harris et al. | |
| 6,011,068 A | 1/2000 | Nemeth et al. | |
| 6,031,003 A | 2/2000 | Nemeth et al. | |
| 6,211,244 B1 | 4/2001 | Van Wagenen et al. | |
| 6,313,146 B1 | 11/2001 | Van Wagenen et al. | |
| 7,250,533 B2 | 7/2007 | Lifshitz-Liron et al. | |
| 7,294,735 B2 | 11/2007 | Lifshitz-Liron et al. | |
| 7,393,967 B2 | 7/2008 | Lifshitz-Liron et al. | |
| 7,563,930 B2 | 7/2009 | Wizel et al. | |
| 7,744,861 B2 | 6/2010 | Zhao et al. | |
| 7,786,133 B2 | 8/2010 | Bentley et al. | |
| 8,722,732 B2 | 5/2014 | Riggs-Sauthier et al. | |
| 2005/0136031 A1 | 6/2005 | Bentley et al. | |
| 2006/0293499 A1 | 12/2006 | Bentley et al. | |
| 2010/0010158 A1 | 1/2010 | McManus et al. | |
| 2010/0010194 A1 | 1/2010 | Zhang | |
| 2011/0200550 A1 | 8/2011 | Kozlowski et al. | |
| 2012/0238621 A1 | 9/2012 | Riggs-Sauthier et al. | |

FOREIGN PATENT DOCUMENTS

| | | |
|---|---|---|
| WO | WO 02/098949 | 12/2002 |
| WO | WO 2005/028539 | 3/2005 |
| WO | WO 2005/058367 | 6/2005 |
| WO | WO 2007/098466 | 8/2007 |
| WO | WO 2008/121386 | 10/2008 |
| WO | WO 2009/151590 | 12/2009 |
| WO | WO 2011/056325 | 5/2011 |

OTHER PUBLICATIONS

Bacchi, et al., "Novel Synthetic Polyamines Are Effective in the Treatment of Experimental Microsporidiosis, an Opportunistic AIDS-Associated Infection", Antimicrobial Agents and Chemotherapy, vol. 46, No. 1, pp. 55-61, (Jan. 2002).

Block, et al., "Cinacalcet for Secondary Hyperparathyroidism in Patients Receiving Hemodialysis", N. Engl. J. Med., vol. 350, No. 15, pp. 1516-1525, (Apr. 2004).

Brinkley, "A Brief Survey of Methods for Preparing Protein Conjugates with Dyes, Haptens, and Cross-Linking Reagents", Bioconjugate Chem., vol. 3, pp. 2-13, (1992).

Brown, et al., "Cloning and Characterization of an Extracellular Ca2+-Sensing Receptor from Bovine Parathyroid", Nature, vol. 366, pp. 575-580, (Dec. 1993).

Chen, et al., "Synthesis and Properties of ABA Amphiphiles", J. Org. Chem., vol. 64, pp. 6870-6873, (1999).

Lopez, et al., "The Effect of Calcitriol, Paricalcitol, and a Calcimimetic on Extraosseous Calcifications in Uremic Rats", Kidney International, vol. 73, pp. 300-307, (2008).

Marcus, et al., "Turning Low-Molecular-Weight Drugs into Prolonged Acting Prodrugs by Reversible Pegylation: A Study with Gentamicin", Journal of Medicinal Chemistry, vol. 51, No. 14, pp. 4300-4305, (2008).

Nemeth, et al., "Calcimimetics with Potent and Selective Activity on the Parathyroid Calcium Receptor", Proc. Natl. Acad. Sci. USA, vol. 95, pp. 4040-4045, (Mar. 1998).

Nemeth, et al., "Pharmacodynamics of the Type II Calcimimetic Compound Cinacalcet HCl", Journal of Pharmacology and Experimental Therapeutics, vol. 308, No. 2, pp. 627-635, (2004).

(Continued)

*Primary Examiner* — Kathrien Cruz

(57) ABSTRACT

The invention relates to (among other things) oligomer-calcimimetic conjugates and related compounds. A conjugate of the invention, when administered by any of a number of administration routes, exhibits advantages over previously administered compounds.

20 Claims, 13 Drawing Sheets

(56) References Cited

OTHER PUBLICATIONS

Rodriguez, et al., "The Calcium-Sensing Receptor: a Key Factor in the Pathogenesis of Secondary Hyperparathyroidism", Am. J. Physiol. Renal Physiol., vol. 288, pp. F253-F264, (Feb. 2005).

Urena, et al., "Calcimimetic agents: Review and perspectives", Kidney International, vol. 63, Supplement No. 85, pp. S91-S96, (2003).

Zhao, et al., "Novel Prodrugs of SN38 Using Multiarm Poly(ethylene glycol) Linkers", Bioconjugate Chem., vol. 19, pp. 849-859, (2008).

PCT International Search Report corresponding to PCT Application No. PCT/US2010/050761 date of mailing May 20, 2011.

PCT International Preliminary Report on Patentability and Written Opinion corresponding to PCT Application No. PCT/US2010/050761 date of mailing Apr. 12, 2012.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005—2006).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Chinese First Office Action corresponding to Chinese Patent Application No. 201080043400.0 dated Feb. 28, 2013.

European Office Action corresponding to European Patent Application No. 10 810 996.8-1453 dated Jun. 17, 2013.

Chinese Second Office Action corresponding to Chinese Patent Application No. 201080043400.0 dated Nov. 25, 2013.

Australian Patent Examination Report No. 1 in Australian Patent Application No. 2010315805 dated Sep. 10, 2014.

English translation of Chinese Third Office Action in Chinese Patent Application No. 201080043400.0 dated Jun. 4, 2014.

English translation of Chinese Fourth Office Action in Chinese Patent Application No. 201080043400.0 dated Feb. 3, 2015.

English translation of Israeli First Substantive Examination Report in Israeli Patent Application No. 218869 dated Jan. 25, 2015.

English translation of Japanese Notice of Reasons for Rejection in Japanese Patent Application No. 2012-531124 mailed Oct. 30, 2014.

English Translation of Israeli Substantive Examination Report in Israeli Patent Application No. 218869 dated Jun. 30, 2015.

Dashed line indicates baseline PTH level without drug treatment

Dashed line indicates baseline PTH level without drug treatment

Dashed line indicates baseline PTH level without drug treatment

OLIGOMER-CALCIMIMETIC CONJUGATES AND RELATED COMPUNDS

CROSS REFERENCE TO RELATED APPLICATIONS

This application is a continuation of U.S. patent application Ser. No. 13/433,100, filed Mar. 28, 2012, now U.S. Pat. No. 8,722,732, which is a Continuation-In-Part of International Patent Application No. PCT/US2010/050761, filed Sep. 29, 2010, which claims priority to U.S. Provisional Application Ser. No. 61/246,931, filed Sep. 29, 2009, and said U.S. patent application Ser. No. 13/433,100, additionally claims priority to U.S. Provisional Application No. 61/597,663, filed Feb. 10, 2012, the disclosures of which are incorporated by reference in their entireties.

FIELD OF THE INVENTION

This invention comprises (among other things) conjugates of a calcimimetic that possess certain advantages over the calcimimetic in unconjugated form. The conjugates (also referred to as "inventive compounds" and "compounds of the invention") described herein relate to and/or have application(s) in (among others) the fields of drug discovery, pharmacotherapy, physiology, organic chemistry and polymer chemistry.

BACKGROUND OF THE INVENTION

Calcimimetics are small molecule drugs that mimic the action of calcium on tissues through allosteric activation of the calcium-sensing receptor that is expressed in various human organ tissues. Among other uses, calcimimetics are used to treat patients suffering from hyperparathyroidism, often caused by parathyroid cancers and chronic renal failure. A calcimimetic available commercially is $(\alpha R)\text{-}(-)\text{-}\alpha\text{-methyl-}N\text{-}[3\text{-}[3\text{-}[trifluoromethylphenyl]propyl]\text{-}1\text{-napthalenemethanamine}$ or cinacalcet, sold as the SENSIPAR® brand of cinacalcet in North America and Australia (Amgen Inc., Thousand Oaks, Calif.) and the MIMPARA® brand of cinacalcet in Europe (Amgen Inc., Thousand Oaks, Calif.).

Briefly, calcimimetics are a class of orally active, small molecules that decrease the secretion of parathyroid hormone (PTH) by activating calcium receptors. The secretion of parathyroid hormone is normally regulated by the calcium-sensing receptor. Calcimimetics increase the sensitivity of this receptor to calcium, which inhibits the release of parathyroid hormone, thereby lowering parathyroid hormone levels within a few hours.

Despite the availability of cinacalcet as a representative member of the calcimimetics, its use in patients is associated with drawbacks. For example, cinacalcet is an inhibitor of CYP2D6, which can increase the blood concentration of drugs metabolized by CYP2D6. Thus, co-administration of cinacalcet with other drugs may cause deleterious drug-drug interactions. In addition, cinacalcet is typically administered at least once daily, whereas a less frequent dose (e.g., once a week dosing) would allow for a more convenient regimen. Further, a calcimimetic with a half-life longer than cinacalcet's 30 to 40 hours would allow for less frequent dosing, providing a more convenient treatment regimen, increased patient compliance, and reduced side effects. Additionally, reducing Cmax would avoid potential hypocalcemia and other risks associated with a high Cmax. Reduction of one or more of these side effects from calcimimetics would enhance their desirability as therapeutic drugs.

The present invention seeks to address these and other needs in the art.

SUMMARY OF THE INVENTION

In one or more embodiments of the invention, a compound is provided, the compound comprising a calcimimetic residue covalently attached via a stable or releasable linkage to a water-soluble, non-peptidic oligomer, and pharmaceutically acceptable acid addition salts or complexes thereof. Compositions of enantiomers of the calcimimetic are also contemplated wherein the composition comprises one enantiomer in an amount greater than the other (e.g., one enantiomer is substantially present in the composition and the other enantiomer is substantially absent in the composition), wherein R enantiomers are preferred.

Exemplary compounds of the invention include those compounds comprising a calicimimetic residue covalently attached via a stable or releasable linkage to a water-soluble, non-peptidic oligomer, and pharmaceutically acceptable acid addition salt or complexes thereof.

Exemplary compounds of the invention include those having the following structure:

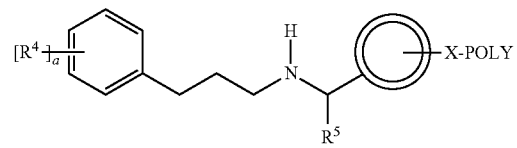

(Formula II-Ca)

wherein:

◎ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)O$CH_3$), —C(O)NH-lower alkyl (e.g., —C(O)NH—$CH_3$), —C(O)N-lower alkyl$_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl);

where "lower alkyl" is selected from a group consisting of 1 to 6 carbon atoms;

X is a spacer moiety (or "linkage"); and

POLY is a water-soluble, non-peptidic oligomer; or a pharmaceutically acceptable salt or solvate thereof.

Further exemplary compounds of the invention include those having the following structure:

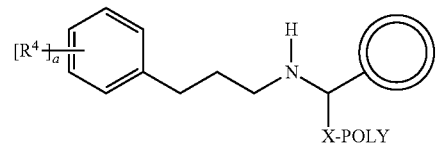

(Formula II-Cb)

wherein:
◎ is selected from the group consisting of 3-methoxyphenyl, 3-chlorophenyl and 1-naphthyl;
each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;
where "lower alkyl" is selected from a group consisting of 1 to 6 carbon atoms;
X is a spacer moiety (or "linkage"); and
POLY is a water-soluble, non-peptidic oligomer.
Further exemplary compounds of the invention include those having the following structure:

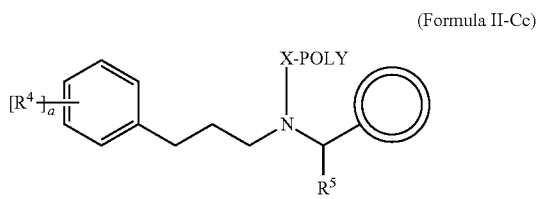

(Formula II-Cc)

wherein:
◎ is selected from the group consisting of 3-methoxyphenyl, 3-chlorophenyl and 1-naphthyl;
each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;
$R^5$ is lower alkyl (e.g., methyl);
where "lower alkyl" is selected from a group consisting of 1 to 6 carbon atoms;
X is a spacer moiety (or "linkage"); and
POLY is a water-soluble, non-peptidic oligomer.
Further exemplary compounds of the invention include those having the following structure:

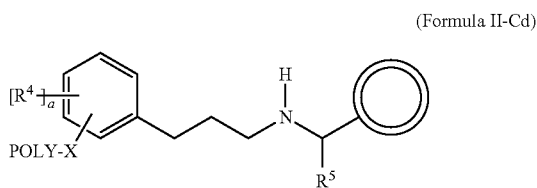

(Formula II-Cd)

wherein
◎ is selected from the group consisting of 3-methoxyphenyl, 3-chlorophenyl and 1-naphthyl;
each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a') is an integer from 1 to 4;
$R^5$ is lower alkyl (e.g., methyl);
where "lower alkyl" is selected from a group consisting of 1 to 6 carbon atoms;
X is a spacer moiety (or "linkage"); and
POLY is a water-soluble, non-peptidic oligomer; or a pharmaceutically acceptable salt or solvate thereof.
Further exemplary compounds of the invention include those having the following structure:

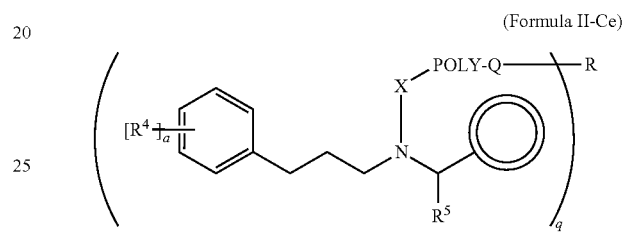

(Formula II-Ce)

wherein:
◎ is selected from the group consisting of 3-methoxyphenyl, 3-chlorophenyl and 1-naphthyl;
each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;
$R^5$ is lower alkyl (e.g., methyl);
where "lower alkyl" is selected from a group consisting of 1 to 6 carbon atoms;
R is a residue of polyol, polythiol or polyamine bearing from 3 to about 50 hydroxyl, thiol or amino groups;
Q is a linker (and, in one or more embodiments, a hydrolytically stable linker);
POLY is a water-soluble, non-peptidic polymer;
each X is independently a spacer moiety that includes a releasable linkage (e.g., a hydrolyzable linkage, an enzymatically degradable linkage, and so forth); and
q is a positive integer from 3 to about 50 (e.g., 4), or a pharmaceutically acceptable salt or solvate thereof.
In one or more embodiments of the invention, a composition is provided, the composition comprising four-arm compounds, wherein at least 80% of the four-arm compounds in the composition have a structure encompassed by the formula,

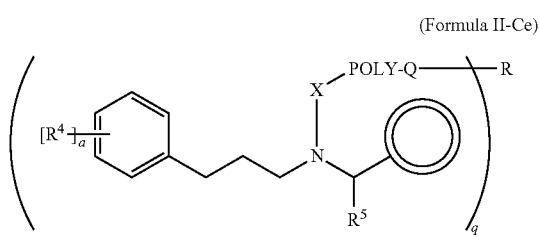

(Formula II-Ce)

wherein:

◯ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl);

where "lower alkyl" is selected from a group consisting of 1 to 6 carbon atoms;

R is a residue of polyol, polythiol or polyamine bearing from 3 to about 50 hydroxyl, thiol or amino groups;

Q is a linker (and, in one or more embodiments, a hydrolytically stable linker);

POLY is a water-soluble, non-peptidic polymer;

each X is independently a spacer moiety that includes a releasable linkage (e.g., a hydrolyzable linkage, an enzymatically degradable linkage, and so forth); and q is 4; or a pharmaceutically acceptable salt or solvate thereof.

The "calcimimetic residue" is a compound having a structure of a calcimimetic that is altered by the presence of one or more bonds, which bonds serve to attach (either directly or indirectly) one or more water-soluble, non-peptidic oligomers.

In this regard, any compound that is a calcimimetic can be used as a calcimimetic. Preferred calcimimetics are described in U.S. Pat. No. 6,011,068.

Exemplary calcimimetic moieties have a structure encompassed by Formula I:

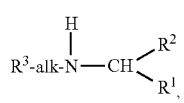

(Formula I)

wherein:

alk is selected from the group consisting of n-propylene, 2,4-butylene and 1,3-butylene;

$R^1$ is selected from the group consisting of lower alkyl of from 1 to 3 carbon atoms and lower haloalkyl of from 1 to 3 carbon atoms substituted with from 1 to 7 halogen atoms; and $R^2$ and $R^3$ are independently selected monocyclic or bicyclic carbocyclic aryl or cycloalkyl groups, having 5- to 7-membered rings optionally substituted with 1 to 5 substituents independently selected from the group consisting of: $OCF_3$, lower alkyl of 1 to 3 carbon atoms, lower haloalkyl of 1 to 3 carbon atoms substituted with 1 to 7 halogen atoms, lower alkoxy of 1 to 3 carbon atoms, halogen, nitro, amino, alkylamino, amido, lower alkylamido of 1 to 3 carbon atoms, cyano, hydroxy, acyl of 2 to 4 carbon atoms, lower hydroxyalkyl of 1 to 3 carbon atoms, and lower thioalkyl of 1 to 3 carbon atoms; and optionally, if $R_2$ is phenyl, then said phenyl $R_2$ has at least one substituent that is not 4-OH-phenyl.

Preferred calcimimetics are encompassed by the following formula:

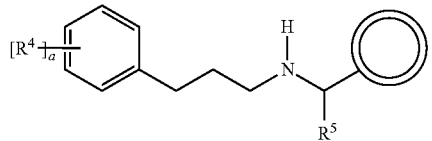

(Formula II)

wherein:

◯ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)$OCH_3$), —C(O)NH-lower alkyl (e.g., —C(O)NH—$CH_3$), —C(O)N-lower $alkyl_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl); and where "lower alkyl" is selected from a group consisting of 1 to 6 carbon atoms.

In one or more embodiments of the invention, a composition is provided, the composition comprising a compound comprising a calcimimetic residue covalently attached via a stable or releasable linkage to a water-soluble, non-peptidic oligomer, and optionally, a pharmaceutically acceptable excipient.

In one or more embodiments of the invention, a dosage form is provided, the dosage form comprising a compound comprising a calcimimetic residue covalently attached via a stable or releasable linkage to a water-soluble, non-peptidic oligomer, wherein the compound is present in a dosage form.

In one or more embodiments of the invention, a method is provided, the method comprising covalently attaching a water-soluble, non-peptidic oligomer to a calcimimetic.

In one or more embodiments of the invention, a method is provided, the method comprising administering a compound comprising a calcimimetic residue covalently attached via a stable or releasable linkage to a water-soluble, non-peptidic oligomer.

These and other objects, aspects, embodiments and features of the invention will become more fully apparent to one of ordinary skill in the art when read in conjunction with the following detailed description.

DETAILED DESCRIPTION OF THE INVENTION

Figure 1A:
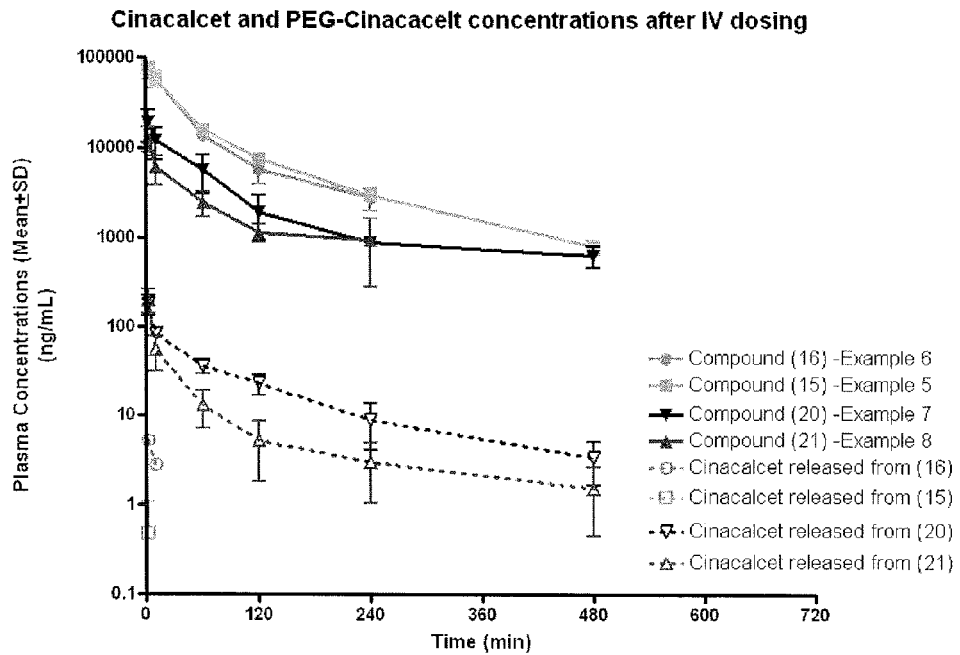
FIG. 1A and FIG. 1B are each graphs showing plasma concentration-time profiles for exemplary compounds and released cinacalcet from exemplary compounds, as further described in Example 14.

As used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 30 monomers. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which substantially all (preferably all) monomeric subunits are ethylene oxide subunits, though the oligomer may contain distinct end capping moieties or functional groups, e.g., for conjugation. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG oligomers, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" is used herein to refer to a molecular structure that helps the conjugates of the invention to localize to a targeting area, e.g., help enter a cell, or bind a receptor. Preferably, the targeting moiety comprises of vitamin, antibody, antigen, receptor, DNA, RNA, sialyl Lewis X antigen, hyaluronic acid, sugars, cell specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidyl glycerol, and phospatidylethanolamine. These lipids may be in the form of micelles or liposomes and the like. The targeting moiety may further comprise a detectable label or alternately a detectable label may serve as a targeting moiety. When the conjugate has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Branched," in reference to the geometry or overall structure of an oligomer, refers to an oligomer having two or more polymer "arms" extending from a branch point.

"Forked," in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically releasable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the calcimimetic. A composition comprised of monodisperse conjugates may, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the calcimimetic. A composition comprised of bimodal conjugates may, however, include one or more nonconjugate substances such as solvents, reagents, excipients, and so forth.

A "calcimimetic" refers to an organic, inorganic, or organometallic compound having a molecular weight of less than about 1000 Daltons and having some degree of calcimimetic activity. By using known assays, one of ordinary skill in the art will be able to determine whether any given compound has calcimimetic activity. Among the activities of a calcimimetic, increasing the sensitivity of the calcium-sensing receptor to activation by extracellular calcium is exemplary.

A "biological membrane" is any membrane made of cells or tissues that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, and rectal mucosa. Unless the context clearly dictates otherwise, the term "biological membrane" does not include those membranes associated with the middle gastro-intestinal tract (e.g., stomach and small intestines).

A "biological membrane crossing rate," provides a measure of a compound's ability to cross a biological membrane, such as the blood-brain barrier ("BBB"). A variety of methods may be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or may be determined by one of ordinary skill in the art.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, 2-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to a component that may be included in the compositions of the invention causing no significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a calcimimetic residue covalently attached via a stable or releasable linkage to a water-soluble, non-peptidic oligomer, and pharmaceutically acceptable acid addition salts or complexes thereof.

In one or more embodiments of the invention, a compound is provided, the compound comprising a calicimimetic residue covalently attached via a stable or releasable linkage to a water-soluble, non-peptidic oligomer, and pharmaceutically acceptable acid addition salt or complexes thereof, wherein the calcimimetic has the following structure:

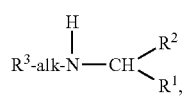

(Formula I)

wherein:

alk is selected from the group consisting of n-propylene, 2,4-butylene and 1,3-butylene;

$R^1$ is selected from the group consisting of lower alkyl of from 1 to 3 carbon atoms and lower haloalkyl of from 1 to 3 carbon atoms substituted with from 1 to 7 halogen atoms; and $R^2$ and $R^3$ are independently selected monocyclic or bicyclic carbocyclic aryl or cycloalkyl groups, having 5- to 7-membered rings optionally substituted with 1 to 5 substituents independently selected from the group consisting of: $OCF_3$, lower alkyl of 1 to 3 carbon atoms, lower haloalkyl of 1 to 3 carbon atoms substituted with 1 to 7 halogen atoms, lower alkoxy of 1 to 3 carbon atoms, halogen, nitro, amino, alkylamino, amido, lower alkylamido of 1 to 3 carbon atoms, cyano, hydroxy, acyl of 2 to 4 carbon atoms, lower hydroxyalkyl of 1 to 3 carbon atoms, and lower thioalkyl of 1 to 3 carbon atoms; and optionally, if $R_2$ is phenyl, then said phenyl $R_2$ has at least one substituent that is not 4-OH-phenyl.

Preferred calcimimetics are encompassed by the following formula:

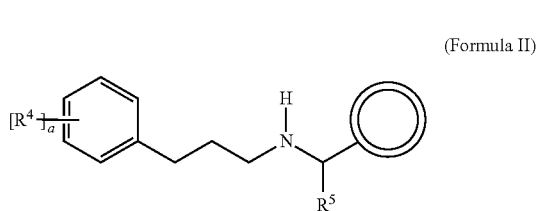

(Formula II)

wherein:

◎ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)O$CH_3$), —C(O)NH-lower alkyl (e.g., —C(O)NH—$CH_3$), —C(O)N-lower alkyl$_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl); and where "lower alkyl" is selected from a group consisting of 1 to 6 carbon atoms.

Calcimimetic moieties encompassed by Formulae I and II and other calcimimetics are described in U.S. Pat. Nos. 6,011,068 and 6,211,244. Approaches for preparing calcimimetics are described in U.S. Pat. Nos. 7,563,930, 7,393,967, 7,250,533, 6,211,244, 6,011,068, 5,648,541 and 4,966,988.

Exemplary compounds of the invention include those having the following structure:

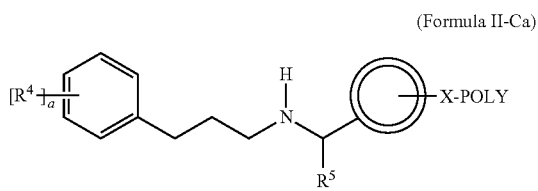

(Formula II-Ca)

wherein:

◎ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)O$CH_3$), —C(O)NH-lower alkyl (e.g., —C(O)NH—$CH_3$), —C(O)N-lower alkyl$_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl);

where "lower alkyl" is selected from a group consisting of 1 to 6 carbon atoms;

X is a spacer moiety (or "linkage"); and

POLY is a water-soluble, non-peptidic oligomer; or a pharmaceutically acceptable salt or solvate thereof.

Further exemplary compounds of the invention include those having the following structure:

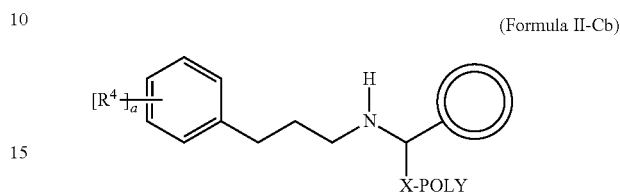

(Formula II-Cb)

wherein:

◎ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)O$CH_3$), —C(O)NH-lower alkyl (e.g., —C(O)NH—$CH_3$), —C(O)N-lower alkyl$_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

where "lower alkyl" is selected from a group consisting of 1 to 6 carbon atoms;

X is a spacer moiety (or "linkage"); and

POLY is a water-soluble, non-peptidic oligomer; or a pharmaceutically acceptable salt or solvate thereof.

Further exemplary compounds of the invention include those having the following structure:

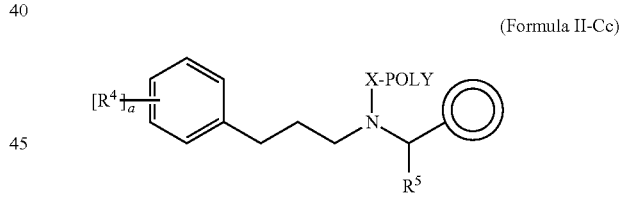

(Formula II-Cc)

wherein

◎ is selected from the group consisting of 3-methoxyphenyl, 3-chlorophenyl and 1-naphthyl;

each $R^4$ is independently selected from the group consisting of —H, —F, —Cl, —Br, —I, phenyl, —$CF_3$, —$CF_2H$, —$CFH_2$, lower alkyl (e.g., —$CH_3$), —O-lower alkyl (e.g., —$OCH_3$), —$OCH_2CF_3$, —OH, —CN, —$NO_2$, —C(O)-lower alkyl (e.g., —C(O)$CH_3$), —C(O)O-lower alkyl (e.g., —C(O)O$CH_3$), —C(O)NH-lower alkyl (e.g., —C(O)NH—$CH_3$), —C(O)N-lower alkyl$_2$ (e.g., —C(O)N($CH_3$)$_2$), —OC(O)-lower alkyl (e.g., —OC(O)$CH_3$), and —NH—C(O)-lower alkyl (e.g., —NH—C(O)$CH_3$);

(a) is an integer from 1 to 5;

$R^5$ is lower alkyl (e.g., methyl);

where "lower alkyl" is selected from a group consisting of 1 to 6 carbon atoms;

X is a spacer moiety (or "linkage"); and

POLY is a water-soluble, non-peptidic oligomer; or a pharmaceutically acceptable salt or solvate thereof.

Further exemplary compounds of the invention include those having the following structure:

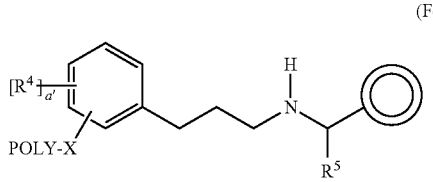

(Formula II-Cd)

wherein:

◎ is selected from the group consisting of 3-methoxyphenyl, 3-chiorophenyl and 1-naphthyl;

each $R^4$ is independently selected from the group consisting of —H, —F, —Cl, —Br, —I, phenyl, —CF$_3$, —CF$_2$H, —CFH$_2$, lower alkyl (e.g., —CH$_3$), —O-lower alkyl (e.g., —OCH$_3$), —OCH$_2$CF$_3$, —OH, —CN, —NO$_2$, —C(O)-lower alkyl (e.g., —C(O)CH$_3$), —C(O)O-lower alkyl (e.g., —C(O)OCH$_3$), —C(O)NH-lower alkyl (e.g., —C(O)NH—CH$_3$), —C(O)N-lower alkyl$_2$ (e.g., —C(O)N(CH$_3$)$_2$), —OC(O)-lower alkyl (e.g., —OC(O)CH$_3$), and —NH—C(O)-lower alkyl (e.g., —NH—C(O)CH$_3$);

(a') is an integer from 1 to 4;

$R^5$ is lower alkyl (e.g., methyl);

where "lower alkyl" is selected from a group consisting of 1 to 6 carbon atoms;

X is a spacer moiety (or "linkage"); and

POLY is a water-soluble, non-peptidic oligomer; or a pharmaceutically acceptable salt or solvate thereof.

Further exemplary compounds of the invention include those having the following structure:

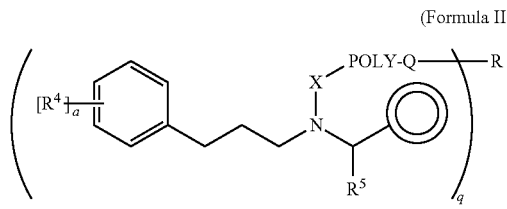

(Formula II-Ce)

wherein:

◎ is selected from the group consisting of 3-methoxyphenyl, 3-chiorophenyl and 1-naphthyl;

each $R^4$ is independently selected from the group consisting of —H, —F, —Cl, —Br, —I, phenyl, —CF$_3$, —CF$_2$H, —CFH$_2$, lower alkyl, —O-lower alkyl, —OCH$_2$CF$_3$, —OH, —CN, —NO$_2$, —C(O)-lower alkyl, —C(O)O-lower alkyl, —C(O)NH-lower alkyl, —C(O)N-lower alkyl$_2$, —OC(O)-lower alkyl, and —NH—C(O)-lower alkyl;

(a) is an integer from 1 to 5;

$R^5$ is lower alkyl;

R is a residue of polyol, polythiol or polyamine bearing from 3 to about 50 hydroxyl, thiol or amino groups;

Q is a linker;

POLY is a water-soluble, non-peptidic polymer;

each X is independently a spacer moiety; and q is a positive integer from 3 to about 50, or a pharmaceutically acceptable salt or solvate thereof.

In one or more embodiments, $R^4$ is selected from the group consisting of —H, —F, —Cl, —Br, —I, —CF$_3$, —CF$_2$H, —CFH$_2$, —CH$_3$, —OCH$_3$, —OCH$_2$CF$_3$, —OH, —CN, —NO$_2$, —C(O)CH$_3$, —C(O)OCH$_3$, —C(O)NH—CH$_3$, —C(O)N(CH$_3$)$_2$, —OC(O)CH$_3$, and —NH—C(O)CH$_3$. In one or more embodiments, $R^4$ is —CF$_3$.

In one or more embodiments, (a) is 1.

In one or more embodiments, $R^5$ is methyl.

In one or more embodiments, Q is a hydrolytically stable linker.

In one or more embodiments, each X is independently a spacer moiety that includes a releasable linkage. In one or more embodiments, each X is independently a spacer moiety that includes a hydrolyzable linkage or an enzymatically degradable linkage.

In one or more embodiments, R is a polyol bearing from 3 to 6 hydroxyl groups. In one or more embodiments, R is pentaerythritol.

In one or more embodiments, the compound of Formula II-Ce is a compound of Formula III:

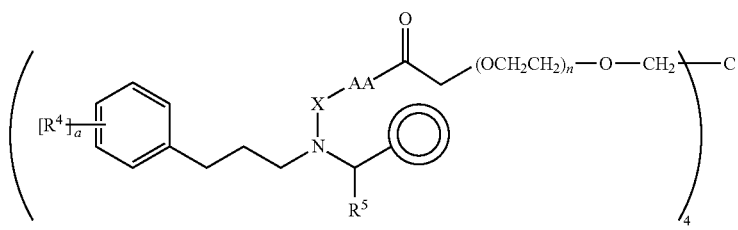

Formula III wherein:

◎ is selected from the group consisting of 3-methoxyphenyl, 3-chloropheny and 1-naphthyl;

each $R^4$ is independently selected from the group consisting of —H, —F, —Cl, —Br, —I, phenyl, —CF$_3$, —CF$_2$H, —CFH$_2$, lower alkyl, —O-lower alkyl, —OCH$_2$CF$_3$, —OH, —CN, —NO$_2$, —C(O)-lower alkyl, —C(O)O-lower alkyl, —C(O)NH-lower alkyl, —C(O)N-lower alkyl$_2$, —OC(O)-lower alkyl, and —NH—C(O)-lower alkyl;

(a) is an integer from 1 to 5;

$R^5$ is lower alkyl;

each n is a positive integer from 10 to about 500;

each X is independently a spacer moiety; and

AA is an amino acid residue;

or a pharmaceutically acceptable salt or solvate thereof.

In one or more embodiments, the compound is a compound of Formula III, wherein $R^4$ is —CF$_3$; (a) is 1; $R^5$ is methyl; ◎ is 1-naphthyl; each n is a positive integer from 10 to about 400; each X is independently a spacer moiety; and AA is an amino acid residue; or a pharmaceutically acceptable salt or solvate thereof.

In one or more embodiments, the compound of Formula II-Ce is a compound of Formula IV:

Formula IV

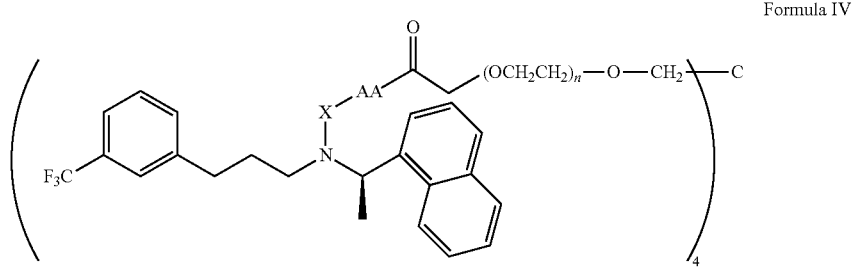

wherein:
each n is a positive integer from 10 to about 500;
each X is independently a spacer moiety; and
AA is an amino acid residue;
or a pharmaceutically acceptable salt or solvate thereof.

In one or more embodiments, the compound of Formula II-Ce is a compound of Formula V:

Formula V

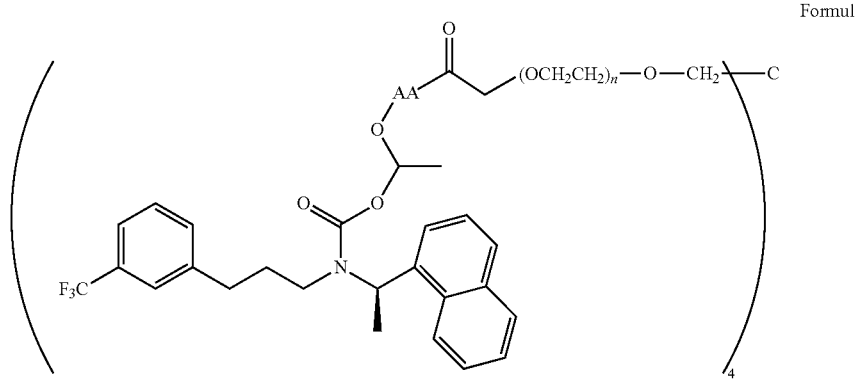

wherein:
each n is a positive integer from 10 to about 500; and
AA is an amino acid residue; or
a pharmaceutically acceptable salt or solvate thereof.

In one or more embodiments of a compound of Formula III, IV, and/or V, n is an integer from about 10 to about 400. In one or more embodiments of a compound of Formula III, IV, and/or V, n is an integer from about 50 to about 400. In one or more embodiments of a compound of Formula III, IV, and/or V, n is an integer from about 50 to about 300. In one or more embodiments of a compound of Formula III, IV, and/or V, n is an integer from about 50 to about 250. In one or more embodiments of a compound of Formula III, IV, and/or V, n is an integer from about 50 to about 200.

In one or more embodiments, the compound of Formula II-Cc is a compound of Formula VI:

wherein:
◎ is selected from the group consisting of 3-methoxyphenyl, 3-chlorophenyl and 1-naphthyl;
each $R^4$ is independently selected from the group consisting of —H, —F, —Cl, —Br, —I, phenyl, —$CF_3$, —$CF_2H$, —$CFH_2$, lower alkyl, —O-lower alkyl, —$OCH_2CF_3$, —OH, —CN, —$NO_2$, —C(O)-lower alkyl, —C(O)O-lower alkyl, —C(O)NH-lower alkyl, —C(O)N-lower alkyl$_2$, —OC(O)-lower alkyl, and —NH—C(O)-lower alkyl;
(a) is an integer from 1 to 5;
$R^5$ is lower alkyl;
each n is a positive integer from 10 to about 2000;
X is a spacer moiety; and
AA is an amino acid residue; or
a pharmaceutically acceptable salt or solvate thereof.

In one or more embodiments, the compound is a compound of Formula VI, wherein $R^4$ is —$CF_3$; (a) is 1; $R^5$ is methyl; ◎ is 1-naphthyl; each n is a positive integer from 10 to about 400; X is an optional spacer moiety; and AA is an amino acid residue; or a pharmaceutically acceptable salt or solvate thereof.

In one or more embodiments, the compound of Formula II-Cc is a compound of Formula VII:

Formula VI

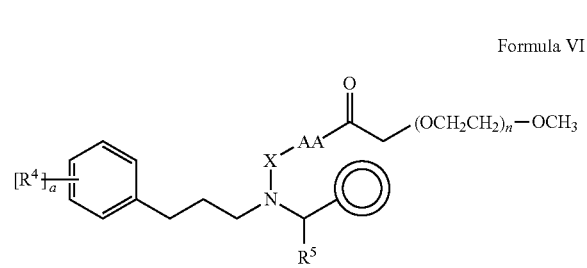

Formula VII

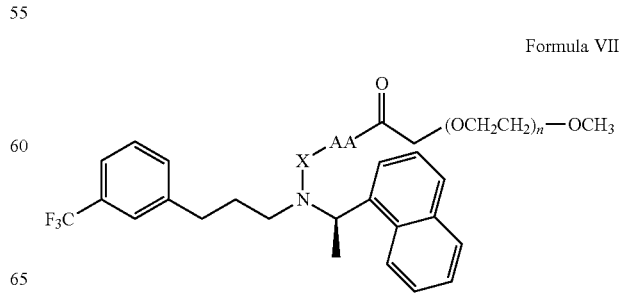

wherein:
each n is a positive integer from 10 to about 2000;
X is a spacer moiety; and
AA is an amino acid residue; or
a pharmaceutically acceptable salt or solvate thereof.

In one or more embodiments, the compound of Formula II-Cc is a compound of Formula VIII:

Formula VIII

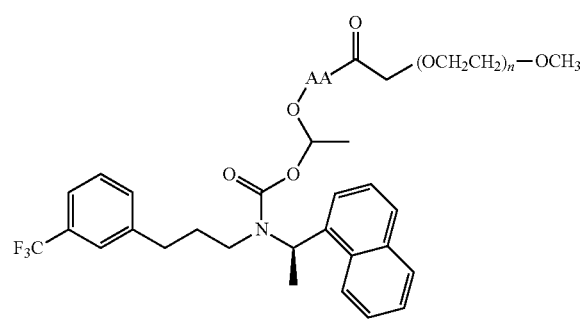

wherein:
each n is a positive integer from 10 to about 2000; and
AA is an amino acid residue; or
a pharmaceutically acceptable salt or solvate thereof.

In one or more embodiments of a compound of Formula VI, VII, and/or VIII, n is an integer from about 10 to about 950. In one or more embodiments of a compound of Formula VI, VII, and/or VIII, n is an integer from about 50 to about 950. In one or more embodiments of a compound of Formula VI, VII, and/or VIII, n is an integer from about 50 to about 800. In one or more embodiments of a compound of Formula VI, VII, and/or VIII, n is an integer from about 100 to about 800. In one or more embodiments of a compound of Formula VI, VII, and/or VIII, n is an integer from about 200 to about 800. In one or more embodiments of a compound of Formula VI, VII, and/or VIII, n is an integer from about 300 to about 700. In one or more embodiments of a compound of Formula VI, VII, and/or VIII, n is an integer from about 450 to about 700.

In one or more embodiments, AA refers to one or more amino acid residues. In one or more embodiments, AA refers to a single amino acid residue. In one or more embodiments, the amino acid residue is chosen from alanine, valine, leucine, isoleucine, glycine, threonine, serine, cysteine, methionine, tyrosine, phenylalanine, tryptophan, aspartic acid, glutamic acid, lysine, arginine, histidine, proline, and non-naturally occurring amino acids. In one or more embodiments AA is chosen from glycine, leucine, valine, and isoleucine. Included in this definition are both the representative L-amino acids and D-amino acids.

In one or more embodiments, the residue of the polyol, polythiol or polyamine, "R," is an organic radical-containing moiety. The polyol, polythiol or polyamine from which "R" is derived possesses from about 3 to about 150 carbon atoms (e.g., from about 3 to about 50 carbon atoms, such as 3, 4, 5, 6, 7, 8, 9, and 10). The residue may contain one more heteroatoms (e.g., O, S, or N). In addition, the residue may be linear. In some instances, the residue may be cyclic.

As previously indicated, the residue of the polyol, polythiol or polyamine, "R," that forms the basis of the branching for the multi-armed conjugates provided herein, originated from a corresponding polyol, polythiol or polyamine (prior to be incorporated into the multi-arm structures containing a water-soluble, non-peptidic polymer). In one or more embodiments, the corresponding polyol, polythiol, or a polyamine bears at least three hydroxyl, thiol, or amino groups, respectively, available for polymer attachment. A preferred polyol is a molecule comprising three or more hydroxyl groups. A preferred polythiol is a molecule that comprises three or more thiol groups. A preferred polyamine is a molecule comprising three or more amino groups.

In one or more embodiments, the polyol, polyamine or polythiol will typically contain 3 to about 25 hydroxyl, or amino groups or thiol groups, respectively, such as from 3 to about 10 (i.e., 3, 4, 5, 6, 7, 8, 9, 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —CH$_2$— is considered as having a length of one intervening atom, —CH$_2$CH$_2$— is considered as having a length of two atoms, and so forth.

Exemplary polyols and polyamines (for which corresponding residues could be present in the conjugates provided herein) have a (Radical)-(OH)$_q$ and (Radical)-(NH$_2$)$_q$ structure, respectively, where (Radical) corresponds to an organic-containing radical and q is a positive integer from 3 to about 50. Note that in Formula II-Ce, the variable "Q," when taken together with R, typically represents a residue of the core organic radical as described herein. That is to say, when describing polyols, polythiols and polymer amines, particularly by name, these molecules are being referenced in their form prior to incorporation into a water-soluble polymer-containing structure. So, for example, a conjugate of Formula II-Ce wherein R is a residue of the polyol, pentaerythritol [C(CH$_2$OH)$_4$], the residue "R" includes carbon (i.e., "C,") and, together with "Q," represents "C(CH$_2$O—)$_4$."

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl)alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol and ethoxylated forms of glycerol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N"-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al. (2002) *Antimicrobial Agents and Chemotherapy*, 46(1):55-61, which is incorporated by reference herein.

Provided below are illustrative structures corresponding to residues of polyols [although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of compounds of Formula I as corresponding to "R" and "Q." In any event, conjugates based on any of the illustrative structures set forth below are included as part of the invention.

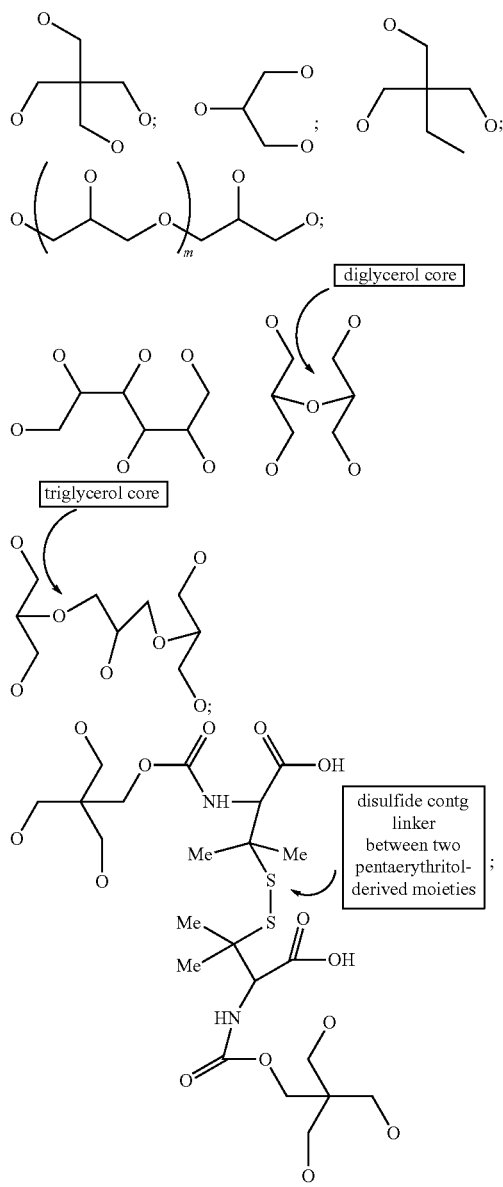

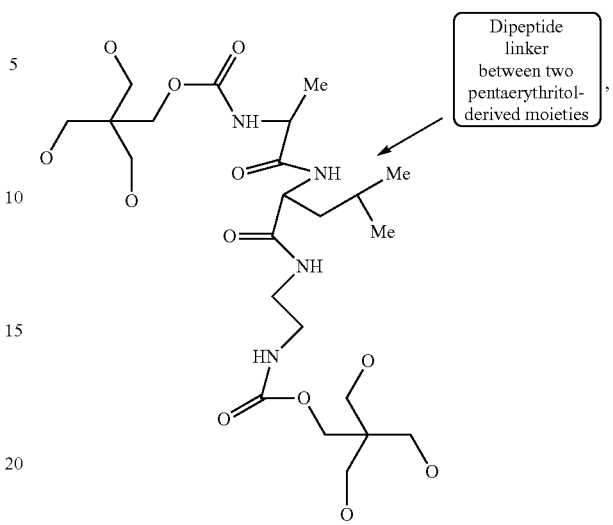

and wherein m is a positive integer from 0-40 [preferably 0-10, e.g., 0-5 (i.e., 0, 1, 2, 3, 4, 5)].

Water-soluble, non-peptidic-containing multi-arm polymers (used as, for example, multi-arm polymeric reagents to prepare conjugates encompassed by Formula II-Ce) based on the above-described polyols, polythiols and polyamines and others are described in WO 2007/098466, U.S. Patent Application Publication No. US 2010/0010158, U.S. Patent Application Publication No. US 2010/0010194, WO 2010/019233, U.S. Patent Application Publication No. 2011/0200550, and U.S. Pat. No. 7,744,861. These references and others describe methods for preparing such multi-arm polymers. In addition, some multi-arm polymers are available commercially from, for example, Creative PEGWorks (Winston Salem, N.C. USA), SunBio PEG-Shop (SunBio USA, Orinda, Calif.), JenKem Technology USA (Allen, Tex.), and NOF America Corporation (White Plains, N.Y.).

The linker "Q" serves to connect the residue of the polyol, polythiol or polyamine bearing at from 3 to about 50 hydroxyl, thiol or amino groups, "R," to each water-soluble, non-peptidic polymer, POLY', in conjugates according to Formula II-Ce. In this regard, the invention is not limited with respect to the specific linker used. In one or more embodiments, the linker between the residue, "R," and the water-soluble, non-peptidic polymer, POLY, is a hydrolytically stable linker.

In one or more embodiments of the invention, the linker, Q, is influenced by the approach used to form the multi-arm polymer employed in preparing the conjugates of the invention. For example, if a water-soluble, non-peptidic polymer bearing a functional group reactive to a hydroxyl, thiol or amine is reacted with a polyol, polythiol or polyamine, respectively, the linker, Q, may include one or more atoms incorporating the bond formed between the termini of the polyol, polythiol or polyamine and the beginning of the repeating monomers of the water-soluble, non-peptidic polymer, POLY. Illustrative linking chemistries in this regard (along with the resulting linkers) are described in the literature and in, for example, Wong (1991) "*Chemistry of Protein Conjugation and Crosslinking*", CRC Press, Boca Raton, Fla., and Brinkley (1992) *Bioconjug. Chem.* 3:2013.

In one or more embodiments of conjugates of Formula II-Ce, Q contains at least one heteroatom such as O, or S, or NH, where the atom proximal to R in Q, when taken together with R, typically represents a residue of an organic radical-containing core of the polyol, polythiol or polyamine. Generally, the linker, Q, contains from 1 to about 10 atoms (e.g., from 1 to about 5 atoms). The linker, Q, typically contains a number of atoms selected from the group consisting of: 1, 2, 3, 4, 5, 6, 7, 8, 9, or 10. Illustrative Qs include —O—, —S—, —NH—, —NH—C(O)— and —C(O)—NH—.

Use of oligomers (e.g., from a monodisperse or bimodal composition of oligomers, in contrast to relatively impure compositions) to form oligomer-containing compounds can advantageously alter certain properties associated with the corresponding small molecule drug. For instance, a compound of the invention, when administered by any of a number of suitable administration routes, such as parenteral, oral, transdermal, buccal, pulmonary, or nasal, exhibits altered metabolism at CYP2D6. Moreover, the compounds of the invention maintain a degree of bioactivity as well as bioavailability in comparison to the bioactivity and bioavailability of the compound free of all oligomers.

Assays for determining whether a given compound (regardless of whether the compound includes a water-soluble, non-peptidic oligomer or not) has calcimimetic activity are known and/or can be prepared by one of ordinary skill in the art.

Each of these (and other) calcimimetic moieties can be covalently attached (either directly or through one or more atoms) to a water-soluble and non-peptidic oligomer.

Exemplary molecular weights of small molecule drugs serving as a calcimimetic include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300, Daltons.

The small molecule drug (i.e., calcimimetic) used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The calcimimetic for coupling to a water-soluble, non-peptidic oligomer possesses a free hydroxyl, carboxyl, thio, amino group, or the like (i.e., "handle") suitable for covalent attachment to the oligomer. In addition, the calcimimetic can be modified by introduction of a reactive group, preferably by conversion of one of its existing functional groups to a functional group suitable for formation of a stable covalent linkage between the oligomer and the drug.

Amino groups on calicimetics provide a point of attachment between the calcimimetic and the oligomer.

There are a number of examples of suitable oligomers activated with one or more functional groups that are useful for forming covalent linkages with available amines of a calcimimetics. Specific examples, along with the corresponding conjugate, are provided in Table 1, below. In the table, the variable (n) represents the number of repeating monomeric units and "—NH-(Cal)" represents the residue of the calcimimetic following conjugation to the oligomer. While each oligomeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

Amine-Selective Oligomers Activated with a Funtional Group and the Calcimimetic Conjugate Formed Therefrom

| Polymeric Reagent | Corresponding Conjugate |
|---|---|
| mPEG-Oxycarbonylimidazole Reagent | H$_3$CO—(CH$_2$CH$_2$O)$_n$—C(=O)—NH—(Cal)<br>Carbamate Linkage |
| mPEG Nitrophenyl Reagent | H$_3$CO—(CH$_2$CH$_2$O)$_n$—C(=O)—NH—(Cal)<br>Carbamate Linkage |
| mPEG-Trichlorophenyl Carbonate Reagent | H$_3$CO—(CH$_2$CH$_2$O)$_n$—C(=O)—NH—(Cal)<br>Carbamate Linkage |
| mPEG-Succinimidyl Reagent | H$_3$C—(OCH$_2$CH$_2$)$_n$—O—CH$_2$—C(=O)—N—(Cal)<br>Amide Linkage |
| Homobifunctional PEG-Succinimidyl Reagent | (Cal)—NH—C(=O)—CH$_2$CH$_2$—(OCH$_2$CH$_2$)$_n$—O—CH$_2$CH$_2$—C(=O)—NH—(Cal)<br>Amide Linkages |

TABLE 1-continued

Amine-Selective Oligomers Activated with a Funtional Group and the Calcimimetic Conjugate Formed Therefrom

| Polymeric Reagent | Corresponding Conjugate |
|---|---|
| Biotin-(CH$_2$)$_4$—NH—CH$_2$CH$_2$—(OCH$_2$CH$_2$)$_n$—OCH$_2$C(O)—O—NHS<br>Heterobifunctional PEG-Succinimidyl Reagent | Biotin-(CH$_2$)$_4$—NH—CH$_2$CH$_2$—(OCH$_2$CH$_2$)$_n$—OCH$_2$CNH—(Cal)<br>Amide Linkage |
| H$_3$C—(OCH$_2$CH$_2$)$_n$—O—CH$_2$CH$_2$—C(O)—O—NHS<br>mPEG-Succinimidyl Reagent | H$_3$C—(OCH$_2$CH$_2$)$_n$—O—CH$_2$CH$_2$—C(O)—NH—(Cal)<br>Amide Linkage |
| H$_3$CO—(CH$_2$CH$_2$O)$_n$—CH$_2$CH$_2$NH—C(O)—CH$_2$CH$_2$—C(O)—O—NHS<br>mPEG-Succinimidyl Reagent | H$_3$CO—(CH$_2$CH$_2$O)$_n$—CH$_2$CH$_2$NH—C(O)—CH$_2$CH$_2$—C(O)—NH—(Cal)<br>Amide Linkage |
| H$_3$CO—(CH$_2$CH$_2$O)$_n$—CH$_2$CH$_2$S—CH$_2$CH$_2$—C(O)—O—NHS<br>mPEG Succinimidyl Reagent | H$_3$CO—(CH$_2$CH$_2$O)$_n$—CH$_2$CH$_2$S—CH$_2$CH$_2$—C(O)—NH—(Cal)<br>Amide Linkage |

TABLE 1-continued

Amine-Selective Oligomers Activated with a Funtional Group and the Calcimimetic Conjugate Formed Therefrom

| Polymeric Reagent | Corresponding Conjugate |
|---|---|
| H$_3$C—(OCH$_2$CH$_2$)$_n$—O—CH$_2$CH$_2$—C(=O)—O—N(succinimidyl)<br>mPEG-Succinimidyl Reagent | H$_3$C—(OCH$_2$CH$_2$)$_n$—O—CH$_2$CH$_2$—C(=O)—NH—(Cal)<br>Amide Linkage |
| H$_3$C—(OCH$_2$CH$_2$)$_n$—O—C(=O)—O—(benzotriazole)<br>mPEG-Benzotriazole Carbonate Reagent | H$_3$C—(OCH$_2$CH$_2$)$_n$—O—C(=O)—NH—(Cal)<br>Carbamate Linkage |
| H$_3$C—(OCH$_2$CH$_2$)$_n$—NH—C(=O)—(C$_6$H$_4$)—C(=O)—O—N(succinimidyl)<br>mPEG-Succinimidyl Reagent | H$_3$C—(OCH$_2$CH$_2$)$_n$—NH—C(=O)—(C$_6$H$_4$)—C(=O)—NH—(Cal)<br>Carbamate Linkage |
| H$_3$CO—(CH$_2$CH$_2$O)$_n$—(C$_6$H$_4$)—C(=O)—O—N(succinimidyl)<br>mPEG-Succinimidyl Reagent | H$_3$CO—(CH$_2$CH$_2$O)$_n$—(C$_6$H$_4$)—C(=O)—NH—(Cal)<br>Amide Linkage |

TABLE 1-continued

Amine-Selective Oligomers Activated with a Funtional Group and the Calcimimetic Conjugate Formed Therefrom

| Polymeric Reagent | Corresponding Conjugate |

TABLE 1-continued

Amine-Selective Oligomers Activated with a Funtional Group and the Calcimimetic Conjugate Formed Therefrom

| Polymeric Reagent | Corresponding Conjugate |
|---|---|
| mPEG-Succinimidyl Reagent | Amide Linkage |
| mPEG-Succinimidyl Reagent | Amide Linkage |
| Homobifunctional PEG-Succinimidyl Reagent | Amide Linkages |
| mPEG-Succinimidyl Reagent | Amide Linkage |

TABLE 1-continued

Amine-Selective Oligomers Activated with a Funtional Group and the Calcimimetic Conjugate Formed Therefrom

| Polymeric Reagent | Corresponding Conjugate |
|---|---|
| Homobifunctional PEG-Succinimidyl Propionate Reagent | Amide Linkages |
| mPEG-Succinimidyl Reagent | Amide Linkage |
| Branched mPEG2-N-Hydroxysuccinimide Reagent | Amide Linkage |
| Branched mPEG2-N-Hydroxysuccinimide Reagent | Amide Linkage |

TABLE 1-continued

Amine-Selective Oligomers Activated with a Funtional Group and the Calcimimetic Conjugate Formed Therefrom

| Polymeric Reagent | Corresponding Conjugate |
|---|---|
| $H_3C-(OCH_2CH_2)_n-O-CH_2-CH_2-C(=O)-S-\text{(2-pyridyl)}$<br>mPEG-Thioester Reagent | $H_3C-(OCH_2CH_2)_n-O-CH_2CH_2C(=O)-NH-(Cal)$<br>Amide Linkage |
| $H(C=O)-CH_2CH_2-(OCH_2CH_2)_n-O-CH_2CH_2-(C=O)H$<br>Homobifunctional PEG Propionaldehyde Reagent | $(Cal)-NH-CH_2CH_2CH_2-(OCH_2CH_2)_n-O-CH_2CH_2CH_2-NH-(Cal)$<br>Secondary Amine Linkages |
| $H_3C-(OCH_2CH_2)_n-O-CH_2CH_2-(C=O)H$<br>mPEG Propionaldehyde Reagent | $H_3C-(OCH_2CH_2)_n-O-CH_2CH_2CH_2-NH-(Cal)$<br>Secondary Amine Linkage |
| $H(C=O)CH_2CH_2CH_2-(OCH_2CH_2)_n-O-CH_2CH_2CH_2-(C=O)H$<br>Homobifunctional PEG Butyraldehyde Reagent | $HN(Cal)-CH_2CH_2CH_2CH_2-(OCH_2CH_2)_n-O-CH_2CH_2CH_2CH_2-NH-(Cal)$<br>Secondary Amine Linkages |
| $H_3C-(OCH_2CH_2)_n-O-CH_2CH_2CH_2-(C=O)H$<br>mPEG Butyraldehyde Reagent | $H_3C-(OCH_2CH_2)_n-O-CH_2CH_2CH_2CH_2-NH-(Cal)$<br>Secondary Amine Linkage |
| $H_3C-(OCH_2CH_2)_n-O-C(=O)-NH-(CH_2CH_2O)_4-CH_2CH_2CH_2(C=O)H$<br>mPEG Butyraldehyde Reagent | $H_3C-(OCH_2CH_2)_n-O-C(=O)NH-(CH_2CH_2O)_4-CH_2CH_2CH_2CH_2-NH-(Cal)$<br>Secondary Amine Linkage |
| $O=C(-(OCH_2CH_2)_n-O-C(=O)-NH-(CH_2CH_2O)_4-CH_2CH_2CH_2CH)(HN-(CH_2CH_2O)_4-CH_2CH_2CH_2CH=O)$<br>Homobifunctional PEG Butyraldehyde Reagent | $O=C(-(OCH_2CH_2)_n-O-C(=O)NH-(CH_2CH_2O)_4-CH_2CH_2CH_2CH_2-NH-(Cal))(HN-(CH_2CH_2O)_4-CH_2CH_2CH_2CH_2-NH-(Cal))$<br>Secondary Amine Linkages |

TABLE 1-continued

Amine-Selective Oligomers Activated with a Funtional Group and the Calcimimetic Conjugate Formed Therefrom

| Polymeric Reagent | Corresponding Conjugate |
|---|---|
| H₃C—(OCH₂CH₂)ₙ—O—C(=O)—NH—CH₂—CH₂—CH₂—CH₂—CH(—C(=O)—NH—(CH₂CH₂O)₄—CH₂CH₂CH)(—O—C(=O)—NH—) ; H₃C—(OCH₂CH₂)ₙ—O—C(=O)—NH—   Branched mPEG2 Butryaldehyde Reagent | H₃C—(OCH₂CH₂)ₙ—O—C(=O)—NH—CH₂—CH₂—CH₂—CH₂—CH₂(—C(=O)—NH—(CH₂CH₂O)₄—CH₂CH₂CH₂—NH—(Cal))(—O—C(=O)—NH—) ; H₃C—(OCH₂CH₂)ₙ—O—C(=O)—NH— ; Secondary Amine Linkage |
| H₃C—(OCH₂CH₂)ₙ—NH—C(=O)—O—CH₂—CH(—O—CH₂)—O—CH₂—CH₂—CH₂—C(=O)—NH—(CH₂CH₂O)₄—CH₂CH₂CH ; H₃C—(OCH₂CH₂)ₙ—NH—C(=O)—O—CH₂   Branched mPEG2 Butyraldehyde Reagent | H₃C—(OCH₂CH₂)ₙ—NH—C(=O)—O—CH₂—HC(—O—CH₂)—OCH₂CH₂—C ; H₃C—(OCH₂CH₂)ₙ—NH—C(=O)—O—CH₂ ; —NH—(CH₂CH₂O)₄—CH₂CH₂CH₂—NH—(Cal) ; H₃C—(OCH₂CH₂)ₙ—O—CH₂CH₂—NH—(Cal) ; Secondary Amine Linkage |
| H₃C—(OCH₂CH₂)ₙ—O—CH₂CH₂—O—CH₂—CH(OCH₂CH₃)—OCH₂CH₃   mPEG Acetyl Reagent | |
| piperidone: N(—C(=O)—CH₂—O—(OCH₂CH₂)ₙ—CH₃) with C=O on ring   mPEG Piperidone Reagent | piperidine: N(—C(=O)—CH₂—O—(OCH₂CH₂)ₙ—CH₃) with NH—(Cal) on ring ; Secondary Amine Linkage (to a secondary carbon) |
| H₃C—(OCH₂CH₂)ₙ—O—(CH₂)₂₋₅—C(=O)—CH₃   mPEG Methylketone Reagent | H₃C—(OCH₂CH₂)ₙ—O—(CH₂)₂₋₅—CH(NH—(Cal))—CH₃ ; secondary amine linkage (to a secondary carbon) |

TABLE 1-continued

Amine-Selective Oligomers Activated with a Funtional Group and the Calcimimetic Conjugate Formed Therefrom

| Polymeric Reagent | Corresponding Conjugate |
|---|---|
| <br>mPEG tresylate Reagent | <br>Secondary Amine Linkage |
| <br>mPEG Maleimide Reagent<br>(under certain reaction conditions such as pH > 8) | <br>Secondary Amine Linkage |
| 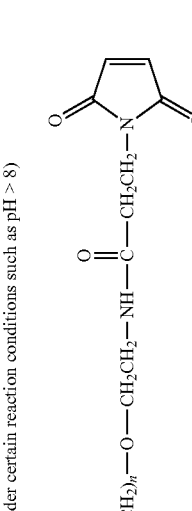<br>mPEG Maleimide Reagent<br>(under certain reaction conditions such as pH > 8) | 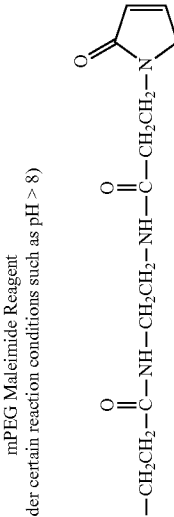<br>Secondary Amine Linkage |
| 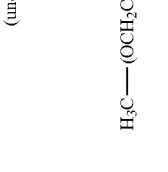<br>mPEG Maleimide Reagent<br>(under certain reaction conditions such as pH > 8) | 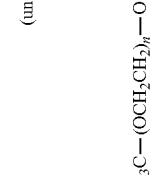<br>Secondary Amine Linkage |

TABLE 1-continued

Amine-Selective Oligomers Activated with a Functional Group and the Calcimimetic Conjugate Formed Therefrom

| Polymeric Reagent | Corresponding Conjugate |
|---|---|
| mPEG Forked Maleimide Reagent (under certain reaction conditions such as pH > 8) | Secondary Amine Linkages |
| branched mPEG2 Maleimide Reagent (under certain reaction conditions such as pH > 8) | Secondary Amine Linkage |

TABLE 1-continued

Amine-Selective Oligomers Activated with a Funtional Group and the Calcimimetic Conjugate Formed Therefrom

TABLE 1-continued
Amine-Selective Oligomers Activated with a Funtional Group and the Calcimimetic Conjugate Formed Therefrom
| Polymeric Reagent | Corresponding Conjugate |
|---|---|
| 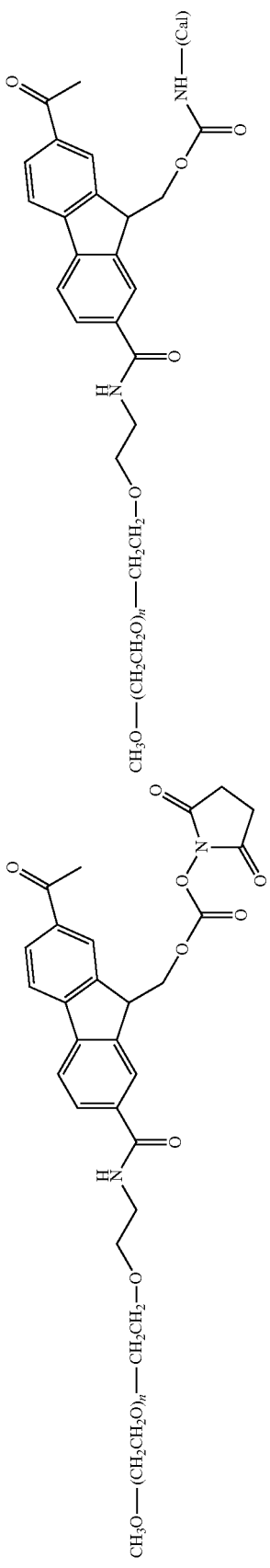 |  |

Conjugation of an oligomer to an amino group of a calcimimetic can be accomplished by a variety of techniques. In one approach, a calcimimetic can be conjugated to an oligomer functionalized with a succinimidyl derivative (or other activated ester or carbonate group, wherein approaches similar to those described for these alternative activated ester group-containing polymeric reagents can be used). In this approach, the oligomer bearing a succinimidyl derivative can be attached to the calcimimetic in an aqueous media at a pH of 7 to 9.0. In addition, an amide linkage can be formed by reacting an amine-terminated water-soluble, nonpeptidic oligomer with a calcimimetic bearing an activating a carboxylic acid group.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble and non-peptidic oligomers described above.

With respect to the compounds of the invention, the molecular weight of the oligomer can either be relatively small or relatively large. For example, and without being bound by theory, it is believed that orally available calcimimetics (in unconjugated form) can substantially retain the ability to be orally available when a relatively small molecular weight (e.g., less than 2,000 Daltons) oligomer is present in the compound. In addition, and again without being bound by theory, even if inclusion of a relatively large (e.g., a molecular weight of from between 2,000 Daltons to about 80,000 Daltons) would require intravenous administration, such administration may not represent a significant drawback inasmuch as patients receiving calicimimetics may already be relying on dialysis, thereby having relatively easy access to the infrastructure and health care providers necessary to administer intravenous drugs.

When the molecular weight of the water-soluble, non-peptidic oligomer, excluding the linker portion, in the compound is relatively small (e.g., less than 2,000 Daltons), exemplary values of the molecular weight of the water-soluble oligomer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers. In yet further embodiments, the oligomer (and the corresponding conjugate) possesses 21, 22, 23, 24, 25, 26, 27, 28, 29 or 30 monomers in series. Thus, for example, when the water-soluble and non-peptidic polymer includes $CH_3-(OCH_2CH_2)_n-$, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the molecular weight of the water-soluble, non-peptidic oligomer, excluding the linker portion, in the compound is relatively large (e.g., greater than 2,000 Daltons), the weight can fall within the range of 2,000 Daltons to about 150,000 Daltons. Exemplary ranges, however, include weight-average molecular weights in the range of from about 3,000 Daltons to about 120,000 Daltons; in the range of from about 5,000 Daltons to about 110,000 Daltons; in the range of from greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given oligomer, poly(ethylene oxides) having a molecular weight in one or more of these ranges are preferred.

Exemplary weight-average molecular weights for the water-soluble oligomer include about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble oligomer (e.g., a branched 40,000 Dalton water-soluble oligomer comprised of two 20,000 Dalton oligomers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGs will typically comprise a number of ($OCH_2CH_2$) monomers [or ($CH_2CH_2O$) monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, from about 1,200 to about 1,900, from about 10 to about 800, and from about 10 to about 400. For any given polymer in which the molecular weight is known, it is possible to determine the number of repeating units (i.e., "n") by dividing the total weight-average molecular weight of the polymer by the molecular weight of the repeating monomer When the water-soluble, non-peptidic oligomer is attached to the calcimimetic (in contrast to the step-wise addition of one or more monomers to effectively "grow" the oligomer onto the calcimimetic), it is preferred that the composition containing an activated form of the water-soluble, non-peptidic oligomer be monodisperse. In those instances, however, where a bimodal composition is employed, the composition will possess a bimodal distribution centering around any two of the above numbers of monomers. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication No. 2005/0136031.

When present, the spacer moiety, also referred herein as a "linker," (through which the water-soluble and non-peptidic polymer is attached to the calcimimetic) may be a single bond, a single atom, such as an oxygen atom or a sulfur atom, two atoms, or a number of atoms. A spacer moiety is typically but is not necessarily linear in nature. The spacer moiety, "X," can be stable or releasable. With respect to enzymes found within living systems, the spacer moiety, "X," can be stable to such enzymes or releasable upon interaction with such enzymes. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" (or "linkage") comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) other atoms, as described further below.

More specifically, in selected embodiments, a spacer moiety (or "linkage") of the invention, X, may be any of the following: "—" (i.e., a covalent bond, that may be stable or degradable, between the calcimimetic residue and the water-soluble, non-peptidic oligomer), —C(O)O—, —OC(O)—, —$CH_2$—C(O)O—, —$CH_2$—OC(O)—, —C(O)O—$CH_2$—, —OC(O)—$CH_2$—, —O—, —NH—, —S—, —C(O)—, C(O)—NH, NH—C(O)—NH, O—C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—

$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —$CH_2$—$CH_2$—$CH_2$—$CH_2$—C(O)—NH—NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$, —$CH_2$—$CH_2$—NH—C(O)—$CH_2$—$CH_2$, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, bivalent cycloalkyl group, —N($R^6$)—, $R^6$ is H or an organic radical selected from the group consisting of alkyl, substituted alkyl, alkenyl, substituted alkenyl, alkynyl, substituted alkynyl, aryl and substituted aryl.

For purposes of the present invention, however, a group of atoms is not considered a linkage when it is immediately adjacent to an oligomer segment, and the group of atoms is the same as a monomer of the oligomer such that the group would represent a mere extension of the oligomer chain.

In one or more embodiments of the invention, the spacer moiety, X, may include a cycloalkylene group, e.g. 1,3- or 1,4-cyclohexylene.

In one or more embodiments of the invention, the spacer moiety, X, has an atom length of from about 1 atom to about 50 atoms, or more preferably from about 1 atom to about 25 atoms, or even more preferably from about 1 atom to about 10 atoms. Typically, the spacer moiety is of an atom length selected from the group consisting of 1, 2, 3, 4, 5, 6, 7, 8, 9 and 10. When considering atom chain length, only atoms contributing to the overall distance are considered. For example, a spacer having the structure, —$\underline{CH_2}$—$\underline{C(O)}$—$\underline{NH}$—$\underline{CH_2CH_2}$—$\underline{O}$—$\underline{CH_2CH_2O}$—$\underline{C(O)}$—$\underline{O}$— has a chain length of 11 atoms, since substituents are not considered to contribute to the length of the spacer.

In one or more embodiments of the invention, the spacer moiety, X, is the spacer moiety, Y, optionally further attached to "Z" (i.e., Y—Z), in the latter case where Y is a spacer moiety covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable.

In one or more embodiments of the invention, when the spacer moiety, X, includes "Y," Y will have the structure: —$(CR_xR_y)_a$—$K_w$—$(CR_xR_y)_b$—$(CH_2CH_2O)_c$—$(CR_xR_y)_d$—$K_z$—, wherein each $R_x$ and $R_y$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), each of $K$, and $K$, is independently selected from —NH—, —C(O)—, —C(O)NH—, —NH—C(O)—, —O—, —S—, O—C(O)—, C(O)—O—, —O—C(O)—O—, O—C(O)—NH—, —NH—C(O)—O—, c ranges from 0 to 25, and Z is selected from C(O)—O—, O—C(O)—O—, —O—C(O)—NH— and —NH—C(O)—O—, d ranges from 0 to 12 (i.e., can be 0, 1, 2, 3, 4, 5, 6, 7, 8, 9, 10, 11, or 12). The particular structure of $K_w$, $K_z$ and of Z will depend upon the values of each of a, b, c, and d such that none of the following linkages result in the overall structure of the spacer moiety, X: —O—O—, NH—O—, —NH—NH—.

In one or more embodiments of the invention, when the spacer moiety, X, is Y—Z. Y will have the structure: —$(CR_xR_y)_a$—$K_w$—$(CR_xR_y)_b$—$(CH_2CH_2O)_c$—$(CR_xR_y)_d$—$K_z$—, where the variables $R_x$, $R_y$, a, b, c and d have the values described in the previous paragraph.

In one or more embodiments of the invention, $R_x$ and $R_y$ (as set forth in each of the two preceding paragraphs) is, in each occurrence, independently H or lower alkyl. In one or more embodiments of the invention, $R_x$ and $R_y$ are, in each occurrence, H. In yet another embodiment, "a" ranges from 0 to 5, i.e., is selected from 0, 1, 2, 3, 4, or 5. In yet another embodiment, b ranges from 0 to 5, i.e., is selected from 0, 1, 2, 3, 4, or 5. In yet another embodiment, c ranges from 0 to 10. In yet another embodiment, "d" ranges from 0 to 5, i.e., is selected from 0, 1, 2, 3, 4, or 5. In yet another embodiment, $K_w$ is —C(O)—NH.

In one or more embodiments, the spacer moiety, X, can also include one or more amino acid residues. In such embodiments, exemplary amino acid residues are residues from the amino acids selected from the group consisting of: alanine, valine, leucine, isoleucine, glycine, threonine, serine, cysteine, methionine, tyrosine, phenylalanine, tryptophan, aspartic acid, glutamic acid, lysine, arginine, histidine, proline, and non-naturally occurring amino acids.

The linkage "X" between the water-soluble, non-peptidic oligomer and the small molecule is typically formed by reaction of a functional group on a terminus of the oligomer (or nascent oligomer when it is desired to "grow" the oligomer onto the calcimimetic) with a corresponding functional group within the calcimimetic. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g., succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O$—$(CH_2$—$CH_2$—O$)_n$—$(CH_2)_p$—C(O)H, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, all but one termini of the water-soluble, non-peptidic oligomer not bearing a functional group is capped to render it unreactive. When the oligomer includes a further functional group at a terminus other than that intended for formation of a conjugate, that group is either selected such that it is unreactive under the conditions of formation of the linkage "X," or it is protected during the formation of the linkage "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative that reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —(CH$_2$)$_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g., hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e., aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the calcimimetic may not have a functional group suited for conjugation. In this instance, it is possible to modify (or "functionalize") the "original" calcimimetic so that it does have a functional group suited for conjugation. For example, if the calcimimetic has an amide group, but an amine group is desired, it is possible to modify the amide group to an amine group by way of a Hofmann rearrangement, Curtius rearrangement (once the amide is converted to an azide) or Lossen rearrangement (once amide is concerted to hydroxamide followed by treatment with tolyene-2-sulfonyl chloride/base).

It is possible to prepare a conjugate of small molecule calcimimetic bearing a carboxyl group wherein the carboxyl group-bearing small molecule calcimimetic is coupled to an amino-terminated oligomeric ethylene glycol, to provide a conjugate having an amide group covalently linking the small molecule calcimimetic to the oligomer. This can be performed, for example, by combining the carboxyl group-bearing small molecule calcimimetic with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule calcimimetic bearing a hydroxyl group wherein the hydroxyl group-bearing small molecule calcimimetic is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

Further, it is possible to prepare a conjugate of a small molecule calcimimetic bearing a hydroxyl group (such as, for example, the calcimimetic having structures encompassed within at least one of Formulae I and II) wherein the hydroxyl group-bearing small molecule calcimimetic is coupled to an oligomeric ethylene glycol bearing an haloformate group [e.g., CH$_3$(OCH$_2$CH$_2$OC(O)-halo, where halo is chloro, bromo, iodo] to result in an carbonate [—O—C(O)—O—] linked small molecule conjugate. This can be performed, for example, by combining a calcimimetic and an oligomeric ethylene glycol bearing a haloformate group in the presence of a nucleophilic catalyst (such as 4-dimethylaminopyridine or "DMAP") to thereby result in the corresponding carbonate-linked conjugate.

In another example, it is possible to prepare a conjugate of a small molecule calcimimetic bearing a ketone group by first reducing the ketone group to form the corresponding hydroxyl group. Thereafter, the small molecule calcimimetic now bearing a hydroxyl group can be coupled as described herein.

In still another instance, it is possible to prepare a conjugate of a small molecule calcimimetic bearing an amine group. In one approach, the amine group-bearing small molecule calcimimetic and an aldehyde-bearing oligomer are dissolved in a suitable buffer after which a suitable reducing agent (e.g., NaCNBH$_3$) is added. Following reduction, the result is an amine linkage formed between the amine group of the amine group-containing small molecule calcimimetic and the carbonyl carbon of the aldehyde-bearing oligomer.

In another approach for preparing a conjugate of a small molecule calcimimetic bearing an amine group, a carboxylic acid-bearing oligomer and the amine group-bearing small molecule calcimimetic are combined, typically in the presence of a coupling reagent (e.g., DCC). The result is an amide linkage formed between the amine group of the amine group-containing small molecule calcimimetic and the carbonyl of the carboxylic acid-bearing oligomer.

The compounds of the invention may be administered per se or in the form of a pharmaceutically acceptable salt, and any reference to the compounds of the invention herein is intended to include pharmaceutically acceptable salts. If used, a salt of a compound as described herein should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the compound with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulfonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

While it is believed that the full scope of the conjugates disclosed herein behave as described, an optimally sized oligomer can be identified as by testing a series of compounds, each having a difference oligomer size and the compound having the best activity is identified as a preferred compound.

With respect to bioavailability, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchioric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as cocoa butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, five times weekly, four times weekly, three times weekly, twice weekly, once weekly, twice monthly, once monthly, and any combination thereof. Once the clinical endpoint has been achieved, dosing of the composition is halted. In certain embodiments the dosing may be synchronized with dialysis, for certain patients.

All articles, books, patents, patent publications and other publications referenced herein are incorporated by reference in their entireties.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by an NMR spectrometer manufactured by Bruker. A list of certain compounds as well as the source of the compounds is provided below.

Example 1

Synthesis of mPEGn-Cinacalcet (n=1, 2, 3, 4, 5, 6, 7 and so Forth)

mPEGn-N-cinacalcet is prepared using a poly(ethylene glycol) bearing a chloroformate. Schematically, the approach followed for this example is shown below.

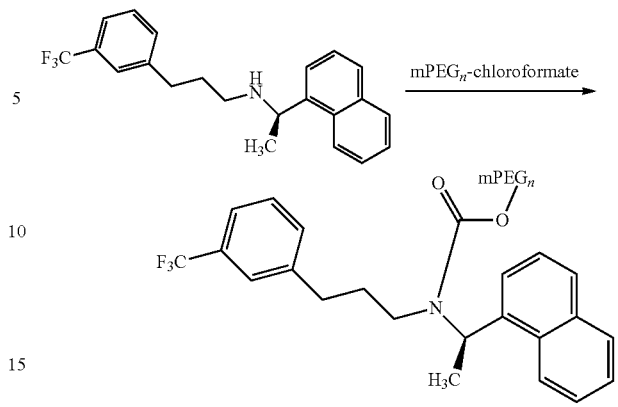

An excess of mPEG$_3$-chloroformate [Cl—C(O)O—CH$_2$CH$_2$O)$_n$CH$_3$] is added to a composition of cinacalcet in the presence of a base at a temperature of 20° C. for two to four hours. The conjugate thus formed is isolated using conventional techniques.

The approach is repeated several times in which each time the approach is repeated, a different mPEGn size [e.g., "n" number of ethylene oxide monomers, wherein n=1, 2, 4, 5, 6, 7 and so forth] is used.

Example 2

Synthesis of mPEGn-Cinacalcet (n=1, 2, 3, 4, 5, 6, 7 and so Forth)

mPEGn-N-cinacalcet is prepared using a poly(ethylene glycol) bearing a leaving group such as a sulphonate (e.g., mesylate or "Ms") or halide. Schematically, the approach followed for this example is shown below.

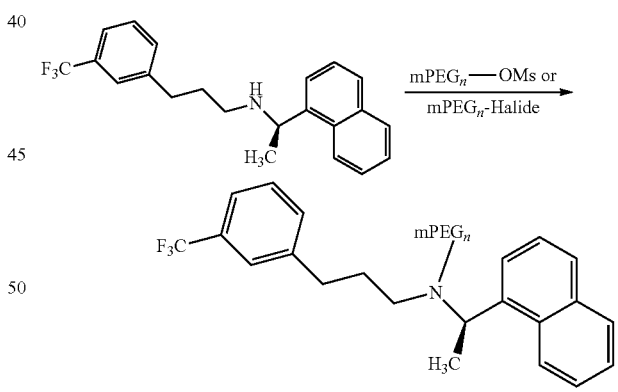

Cinacalcet is dissolved in DMF. To the solution, NaH is added with stirring. After 20 minutes, mPEG$_n$-Halide (e.g, mPEG$_n$-Br) is added to the solution, which is then stirred overnight at room temperature. Dichloromethane (150 mL) is added and the precipitated solid is collected by filtration. The organic filtrate is washed with water (100 mL×2) and then dried. The crude product is purified by column chromatography (SiO$_2$:DCM/Methanol 20:1).

The approach is repeated several times in which each time the approach is repeated, a different mPEGn size [e.g., "n" number of ethylene oxide monomers, wherein n=1, 2, 4, 5, 6, 7 and so forth] is used.

Example 3

Synthesis of mPEGn-Cinacalcet (Relatively Large Oligomer Sizes)

mPEGn-N-cinacalcet wherein the oligomer is relatively large is prepared in accordance with the approach described below.

Briefly, compound 1 is prepared using conventional techniques and reacted with tert-butyl 2-(bis(2-hydroxyethyl)amino)acetate obtained from reacting BICIN with t-BOC anhydride in the presence of the coupling agent N-ethyl-N'-(3-dimethylaminopropyl)carbodiimide (or EDC) to yield compound 2.

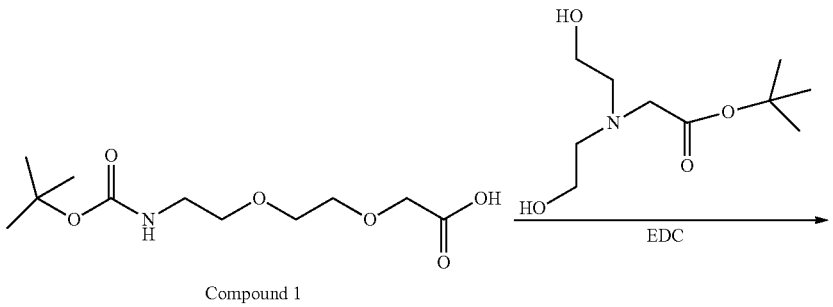

Compound 1

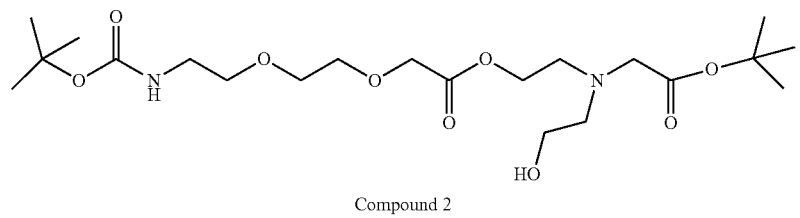

Compound 2

Thereafter, the hydroxyl group of compound 2 is acylated via treatment with reacted with acetyl chloride (AcCl) to provide compound 3.

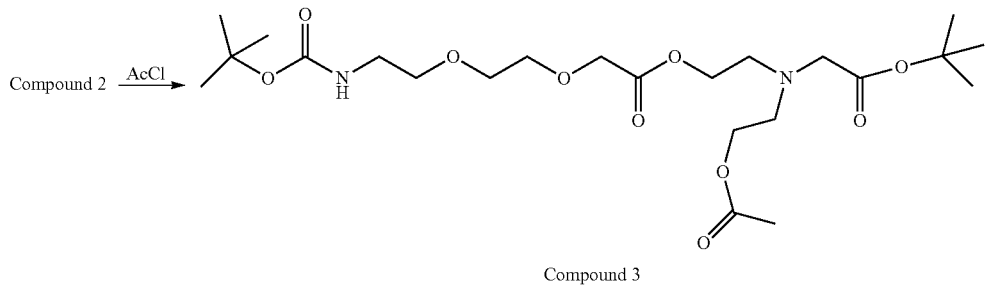 [SMILES: "AcCl" ; CC(=O)OCCN(CCOC(=O)COCCOCCNC(=O)OC(C)(C)C)CC(=O)OC(C)(C)C]

Compound 3

Next, compound 3 is treated with 20% trifluoroacetic acid (TFA) to the TFA salt (compound 4).

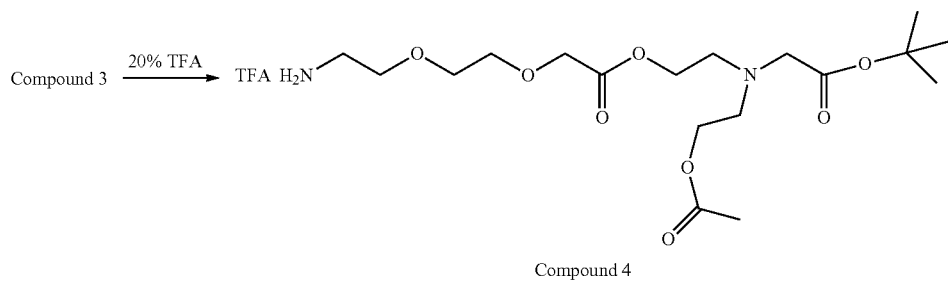 [SMILES: CC(=O)OCCN(CCOC(=O)COCCOCCN)CC(=O)OC(C)(C)C]

Compound 4

Then, compound 4 is dissolved in a suitable solvent and a succinimidyl carbonate-terminated mPEG reagent (molecular weight of about 2,000 Daltons) is coupled the base form of compound 4 to yield compound 5. This step can alternatively be carried out with a chloroformate-terminated mPEG reagent in place of the succinimidyl carbonate-terminated mPEG reagent.

Thereafter, the tert-butyl protecting group within compound 5 is deprotected with 33% TFA to provide a carboxylic acid-containing compound 6.

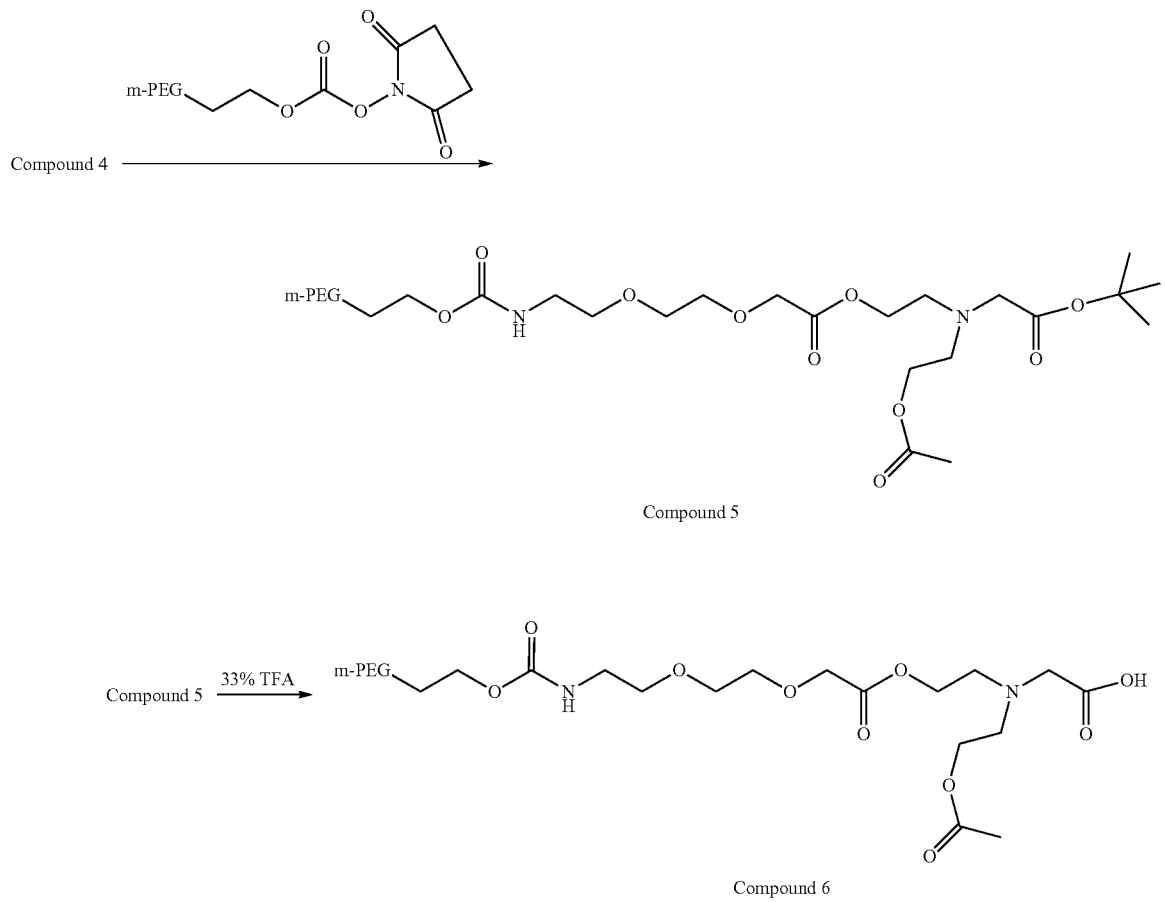

Compound 5

Compound 6

Next, the carboxylic acid of the carboxylic-containing compound 6, is activated with H-hydroxysuccinimide (NHS) in the presence of a coupling agent to provide compound 7.

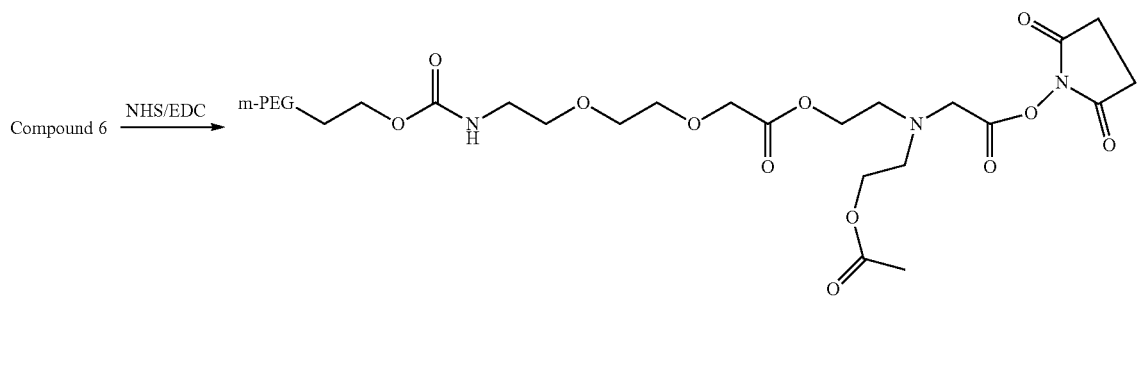

Compound 7

Thereafter, compound 7 is coupled to the secondary amine of cinacalcet to provide compound 8.

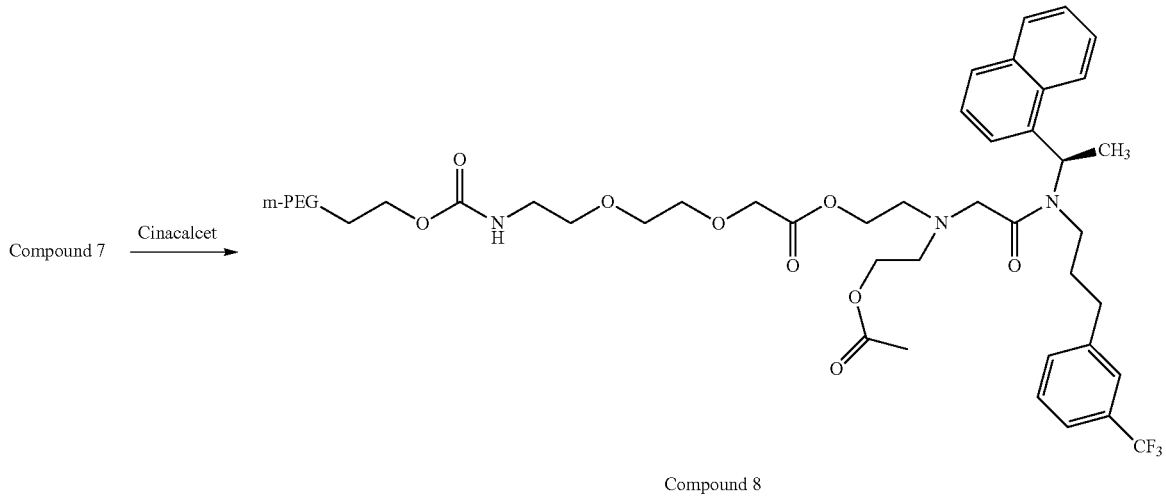

Compound 8

The approach is repeated several times in which each time the approach is repeated, a different mPEG weight (e.g., 5,000 Daltons, 10,000 Daltons, 15,000 Daltons, 20,000 Daltons, 30,000 and 40,000 Daltons) is used.

Example 4

Synthesis of mPEGn-Cinacalcet (Relatively Large Oligomer Sizes)

mPEGn-N-cinacalcet wherein the oligomer is relatively large is prepared in accordance with the schematic provided below. In the schematic, compound 9 (in which each mPEG has a molecular weight of about 2,000 Daltons) is the oligomeric reagent that can be prepared as described in U.S. Patent Application Publication No. 2006/0293499 and can be coupled to cinacalcet to provide compound 10.

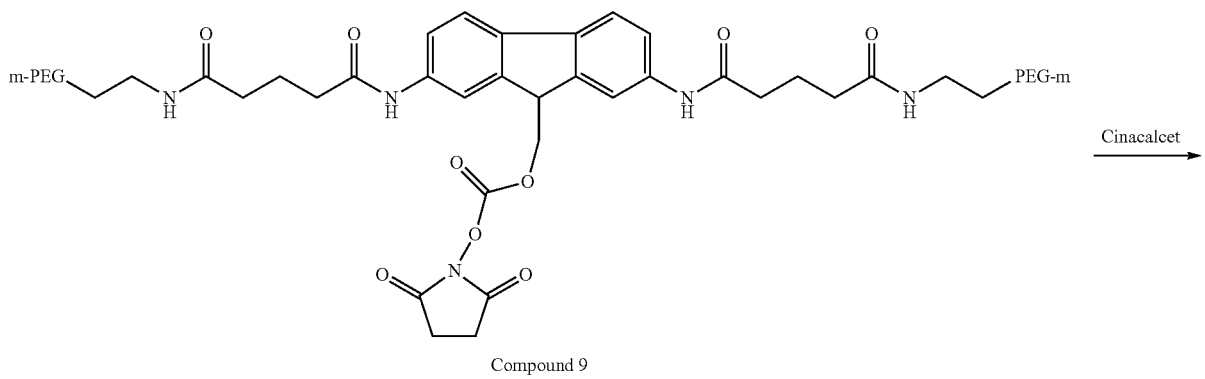

Compound 9

-continued

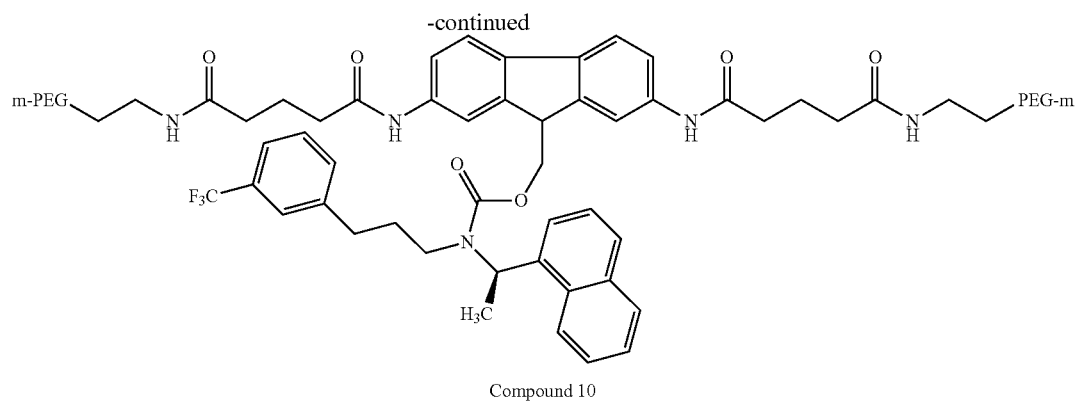

Compound 10

The approach is repeated several times in which each time the approach is repeated, a different mPEG weight (e.g., mPEG weight of 2,500 Daltons to provide a reagent weight of about 5,000 Daltons, mPEG weight of 5,000 Daltons to provide a reagent weight of about 10,000 Daltons, mPEG weight of about 7,500 Daltons to provide a reagent weight of about 15,000 Daltons, mPEG weight of 10,000 Daltons to provide a reagent weight of about 20,000 Daltons, mPEG weight of about 12,500 Daltons to provide a reagent weight of about 25,000 Daltons, mPEG weight of about 15,000 Daltons to provide a reagent weight of about 30,000 Daltons, and mPEG weight of 20,000 Daltons to provide a reagent weight of about 40,000 Daltons) is used.

Example 5

Synthesis of mPEG$_{10k}$-Glycine-Amide-Cinacalcet (15)

Cinacalcet can be linked to an oligomer through a spacer moiety (or "linkage") that contains one or more amino acids. By including one or more amino acids in the linkage, it is possible to affect the overall release rate. For example, a dipeptide can undergo self-cleavage, which represents an extra step in the overall release mechanism and thereby affect the overall release of the active moiety. A compound that includes an amino acid-containing linker between a residue of cinacalcet and an oligomer was prepared following the schematic provided below.

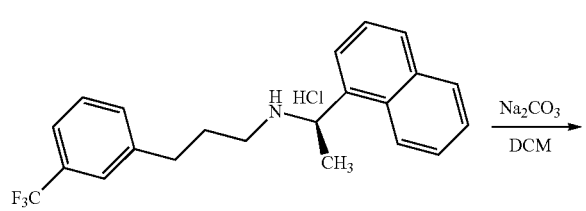

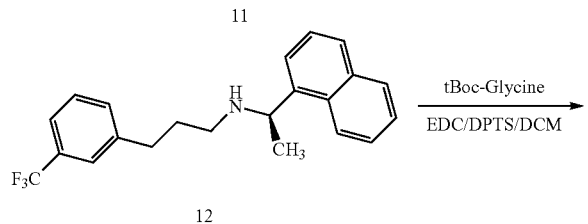

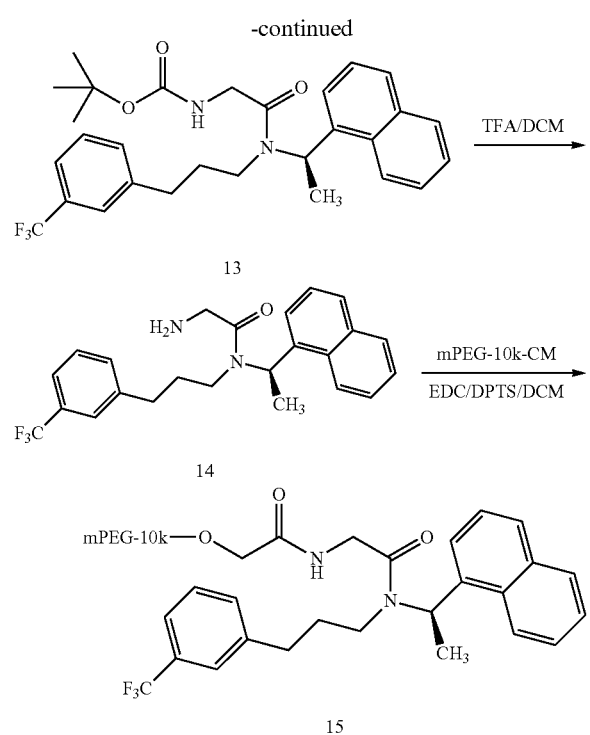

Preparation of Cinacalcet Free Base (12)

Cinacalcet HCl salt (~3.16 g, ~8.02 mmol, 11) was dissolved in dichloromethane (DCM) and the solution was washed with saturated aqueous Na$_2$CO$_3$ solution three times. The dichloromethane solution was dried over Na$_2$SO$_4$, filtered, and the solvent removed under reduced pressure to give cinacalcet free base (12) as a clear liquid (~2.75 g, ~96% yield).

Synthesis of tBoc-Glycine-Amide-Cinacalcet (13)

Cinacalcet free base (~1.0 g, ~2.80 mmol, 12), tBoc-glycine (~0.98 g, ~5.60 mmol) and 4-N,N-dimethylaminopyridinium-tolunesulfonate (DPTS, ~0.42 g, ~1.40 mmol) were dissolved in dichloromethane. N-ethyl-N'-(3-dimethylaminopropyl)carbodiimide (EDC, ~1.3 g, ~8.40 mmol) was then added. The reaction mixture was stirred at room temperature overnight (~18 hours). The dichloromethane reaction mixture was then washed with 0.2N HCl solution three times. The dichloromethane solution was dried over Na$_2$SO$_4$, filtered, and the solvent removed under reduced pressure to give the crude product as a yellow liquid. After chromatography purification, tBoc-glycine-amide-cinacalcet (13) was obtained as a white solid (~0.60 g, ~1.20 mmol, ~42% isolated yield).

Synthesis of Glycine-amide-cinacalcet (14)

tBoc-glycine-amide-cinacalcet (13) (~0.60 g, ~1.20 mmol) was dissolved in dichloromethane (~5 mL), and thereafter trifluoroacetic acid (TFA) (~3 mL) was added and the reaction mixture was stirred at room temperature for four hours. The reaction was monitored by HPLC analysis for completion. The dichloromethane product mixture was washed with saturated aqueous $Na_2CO_3$ solution twice, dried over $Na_2SO_4$. After removing all solvents, glycine-amide-cinacalcet (14) was obtained as a light-yellow liquid (~0.50 g, ~1.20 mmol, quantitative yield).

Preparation of mPEG$_{10k}$-Glycine-amide-cinacalcet (15)

mPEG$_{10k}$-CM [$CH_3O(CH_2CH_2O)_n$—$CH_2CH_2$—$OCH_2$—COOH, (~1.2 g, ~0.12 mmol)], glycine-amide-cinacalcet (14) (~314 mg, ~0.76 mmol) and 4-N,N-dimethylaminopyridinium p-tolunesulfonate (DPTS, ~227 mg, ~0.76 mmol) were dissolved in dichloromethane. N-ethyl-N'-(3-dimethylaminopropyl)carbodiimide (EDC, ~0.40 mL, ~353 mg, ~2.27 mmol) was then added. The reaction mixture was stirred at room temperature overnight (~21 hours). The product mixture was poured into 1:1 isopropanol/diethyl ether with strong stirring, the resulting white precipitate was collected, washed with 1:1 isopropanol/diethyl ether and diethyl ether, and dried in vacuum. mPEG$_{10k}$-glycine-amide-cinacalcet conjugate (15) was obtained as a white solid (~1.15 g, ~95% yield). HPLC showed that the product purity was >95% and there was no small molecule impurity. NMR indicated that the cinacalcet substitution was ~95%.

Example 6

Synthesis of a Multi-armed Oligomer-Cinacalcet (16)

A multi-armed oligomer-cinacalcet (also containing an amino acid-containing spacer moiety) was prepared in accordance with the schematic provided below.

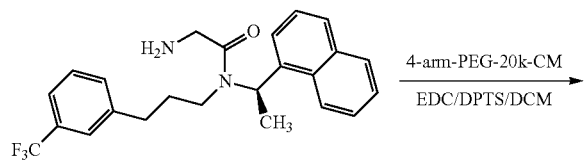

14

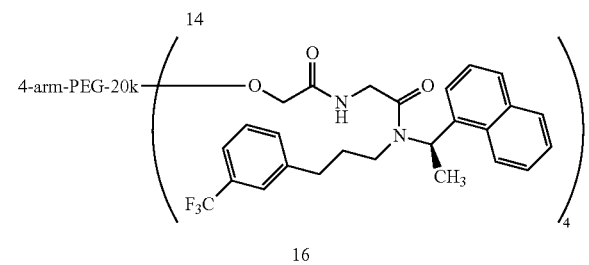

16

Four-arm-PEG$_{20k}$-CM [$C(CH_2O(CH_2CH_2O)_n$—$CH_2CH_2$—$OCH_2$—COOH)$_4$ (~2.0 g, 0.10 mmol)], glycine-amide-cinacalcet (14) (~212 mg, ~0.51 mmol) and 4-N,N-dimethylaminopyridinium p-tolunesulfonate (DPTS, ~154 mg, ~0.51 mmol) were dissolved in dichloromethane. N-ethyl-N'-(3-dimethylaminopropyl)carbodiimide (EDC, ~0.27 mL, ~239 mg, ~1.54 mmol) was then added. The reaction mixture was stirred at room temperature overnight (~18 hours). The product mixture was poured into 1:1 isopropanol/diethyl ether with strong stirring, the resulting white precipitate was collected, washed with 1:1 isopropanol/diethyl ether and diethyl ether, and dried in vacuum. Four-arm-PEG$_{20k}$-glycine-amide-cinacalcet conjugate (16) was obtained as a white solid (~1.9 g, ~95% yield). HPLC analysis showed that the product purity was >95% and there was no small molecule impurity. NMR indicated that the cinacalcet substitution was ~95%.

Example 7

Synthesis of mPEG$_{10k}$-L-Leucine-Acyloxymethyl-Carbamate-Cinacalcet (20)

A compound that includes an amino acid-containing spacer moiety between a residue of cinacalcet and an oligomer was prepared following the schematic provided below.

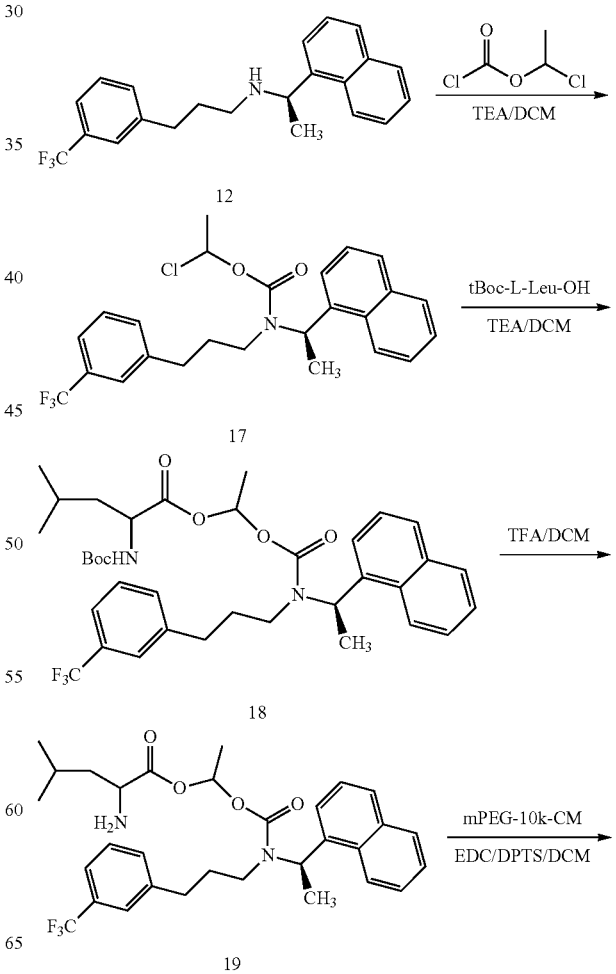

-continued

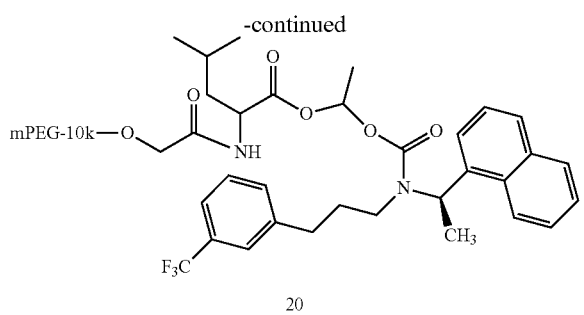

20

Synthesis of 1-chloroethyl-carbamate-cinacalcet (17)

To a dichloromethane solution of cinacalcet (~360 mg, ~1.0 mmol, 12) was added 1-chloroethyl chloroformate (~173 mg, ~1.20 mmol) and triethylamine (TEA, ~0.21 mL, ~153 mg, ~1.50 mmol), the solution was stirred at room temperature for three hours. The dichloromethane product mixture was then washed with 0.1N HCl/NH$_4$Cl aqueous solution twice and Na$_2$CO$_3$ aqueous solution once. The dichloromethane phase was dried over Na$_2$SO$_4$, after solvent evaporation, 1-chloroethyl-carbamate-cinacalcet (17) was obtained as a colorless liquid (~437 mg, ~94% isolated yield).

Synthesis of tBoc-L-leucine-acyloxymethyl-carbamate-cinacalcet (18)

To a dichloromethane solution of 1-chloroethyl-carbamate-cinacalcet (17) (~437 mg, ~0.92 mmol) and tBoc-L-leucine (~871 mg, ~3.77 mmol) was added triethylamine (TEA, ~0.39 mL, ~286 mg, ~2.83 mmol). The reaction mixture was stirred at room temperature overnight (~20 hours), then washed with 0.1N HCl/NH$_4$Cl aqueous solution twice and NaCl aqueous solution once. The crude product was purified by chromatography with hexane/ethyl acetate; tBoc-L-leucine-carbamate-cinacalcet (18) was obtained as a colorless liquid (~280 mg, ~0.43 mmol, ~45% isolated yield).

Synthesis of L-leucine-acyloxymethyl-carbamate-cinacalcet (19)

To a dichloromethane solution of tBoc-L-leucine-carbamate-cinacalcet (18) (~280 mg, ~0.43 mmol) was added trifluoroacetic acid (TFA) (~1.5 mL). The reaction mixture was stirred at room temperature for about one hour. The reaction was monitored by HPLC analysis for completion. The dichloromethane product mixture was washed with 0.1N HCl/NH$_4$Cl aqueous solution three times. The dichloromethane phase was dried over Na$_2$SO$_4$, all solvents were then removed under reduced pressure. L-leucine-acyloxymethyl-carbamate-cinacalcet (19) was obtained as a colorless liquid (~238 mg, quantitative yield).

Preparation of mPEG$_{10k}$-L-leucine-acyloxymethyl-carbamate-cinacalcet (20)

mPEG$_{10k}$-CM (~1.4 g, ~0.14 mmol), L-leucine-acyloxymethyl-carbamate-cinacalcet (19) (~115 mg, ~0.21 mmol) and 4-N,N-dimethylaminopyridinium p-tolunesulfonate (DPTS, ~43 mg, ~0.14 mmol) were dissolved in dichloromethane. N-ethyl-N'-(3-dimethylaminopropyl) carbodiimide (EDC, ~0.20 mL, ~170 mg, ~1.10 mmol) was then added. The reaction mixture was stirred at room temperature overnight (~20 h). The product mixture was poured into 1:1 isopropanol/diethyl ether with strong stirring, the resulting white precipitate was collected, washed with 1:1 isopropanol/diethyl ether and diethyl ether, and dried in vacuum. mPEG$_{10k}$-L-leucine-acyloxymethyl-carbamate-cinacalcet (20) was obtained as a white solid (~1.3 g, ~93% yield). HPLC analysis showed that there was no small molecule impurity. NMR indicated that the cinacalcet substitution was ~80%.

Example 8

Synthesis of Multi-armed Oligomer-Cinacalcet (21)

A multi-armed oligomer-cinacalcet (also containing an amino acid-containing spacer moiety) was prepared in accordance with the schematic provided below.

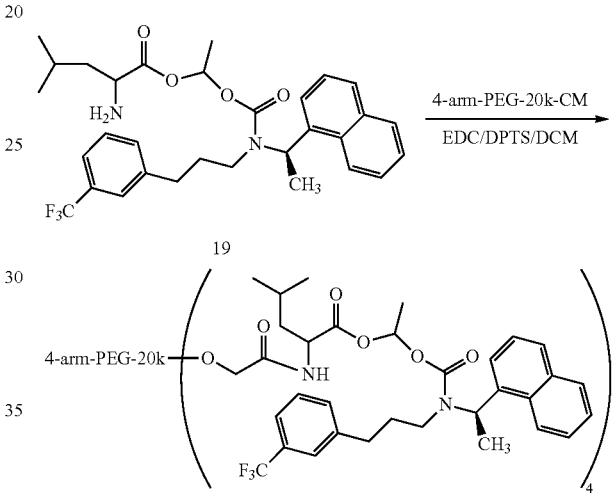

Four-arm-PEG$_{20k}$-CM (~760 mg, ~0.038 mmol), L-leucine-acyloxymethyl-carbamate-cinacalcet (19) (~122 mg, ~0.22 mmol) and 4-N,N-dimethylaminopyridinium p-tolunesulfonate (DPTS, ~65 mg, ~0.21 mmol) were dissolved in dichloromethane. N-ethyl-N'-(3-dimethylaminopropyl)carbodiimide (EDC, ~0.60 mL, ~520 mg, ~3.39 mmol) was then added. The reaction mixture was stirred at room temperature overnight (~22 hours). The product mixture was poured into 1:1 isopropanol/diethyl ether with strong stirring, the resulting white precipitate was collected, washed with 1:1 isopropanol/diethyl ether and diethyl ether, and dried in vacuum. Four-arm-PEG$_{20k}$-L-leucine-acyloxymethyl-carbamate-cinacalcet (21) was obtained as a white solid (~750 mg, ~98% yield). HPLC analysis showed that there was no small molecule impurity and the cinacalcet substitution was ~71%.

Example 9

Synthesis of mPEG$_{10k}$-L-Valine-Acyloxymethyl-Carbamate-Cinacalcet (24)

A compound that includes an amino acid-containing spacer moiety between a residue of cinacalcet and an oligomer was prepared following the schematic provided below.

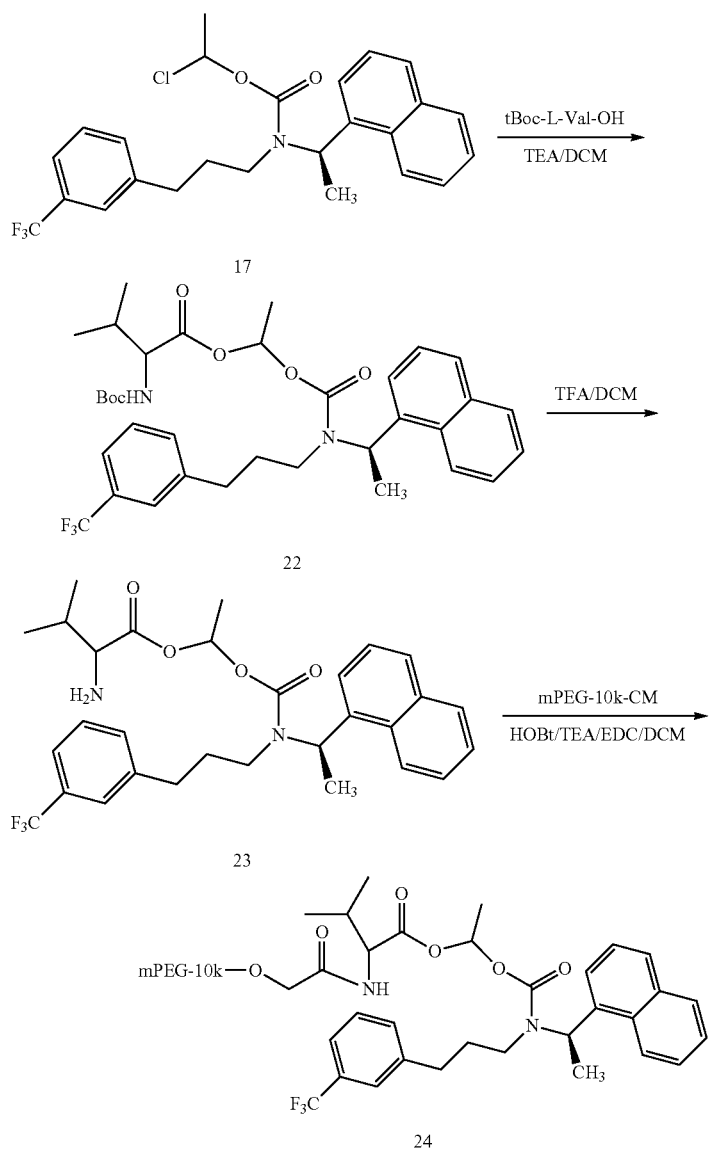

Synthesis of tBoc-L-valine-acyloxymethyl-carbamate-cinacalcet (22)

To a dichloromethane solution of 1-chloroethyl-carbamate-cinacalcet (17) (~748 mg, ~1.61 mmol) and tBoc-L-valine (~1.4 g, ~6.45 mmol) was added triethylamine (TEA, ~0.67 mL, ~489 mg, ~4.84 mmol). The reaction mixture was stirred at room temperature overnight (~20 hours), then washed with 0.1N HCl/NH$_4$Cl aqueous solution twice and NaCl aqueous solution once. The crude product was purified by chromatography with hexane/ethyl acetate; tBoc-L-valine-carbamate-cinacalcet (22) was obtained as a colorless liquid (~900 mg, ~1.40 mmol, ~87% isolated yield).

Synthesis of L-valine-acyloxymethyl-carbamate-cinacalcet (23)

To a dichloromethane solution of tBoc-L-valine-carbamate-cinacalcet (22) (~900 mg, ~1.40 mmol) was added trifluoroacetic acid (TFA) (~2 mL). The reaction mixture was stirred at room temperature for about three hours. The reaction was monitored by HPLC analysis for completion. The dichloromethane product mixture was washed with 0.1N HCl/NH$_4$Cl aqueous solution three times. The dichloromethane phase was dried over Na$_2$SO$_4$. After solvent evaporation, L-valine-acyloxymethyl-carbamate-cinacalcet (23) was obtained as a white solid (~735 mg, ~97% isolated yield).

Synthesis of mPEG$_{10k}$-L-valine-acyloxymethyl-carbamate-cinacalcet (24)

mPEG$_{10k}$-CM (~2.3 g, ~0.23 mmol), L-valine-acyloxymethyl-carbamate-cinacalcet (23) (~180 mg, ~0.33 mmol), triethylamine (TEA, ~0.14 mL, ~100 mg, ~0.99 mmol) and 1-hydroxybenzotriazole (HOBt, ~47 mg, ~0.35 mmol) were dissolved in dichloromethane. N-ethyl-N'-(3-dimethylaminopropyl)carbodiimide (EDC, ~0.20 mL, ~169 mg, ~1.10 mmol) was then added. The reaction mixture was stirred at room temperature overnight (~19 hours). The product mixture was poured into 1:1 isopropanol/diethyl ether with strong stirring, the white precipitate was collected, washed with 1:1 isopropanol/diethyl ether and diethyl ether, and dried in vacuum. mPEG$_{10k}$-L-valine-acyloxymethyl-carbamate-cinacalcet (24) was obtained as a white solid (~2.0 g, ~87% yield). HPLC analysis showed that there was no small molecule impurity. NMR indicated that the cinacalcet substitution was ~72%.

Example 10

Synthesis of Multi-armed Oligomer-Cinacalcet (25)

A multi-armed oligomer-cinacalcet (also containing an amino acid-containing spacer moiety) was prepared in accordance with the schematic provided below.

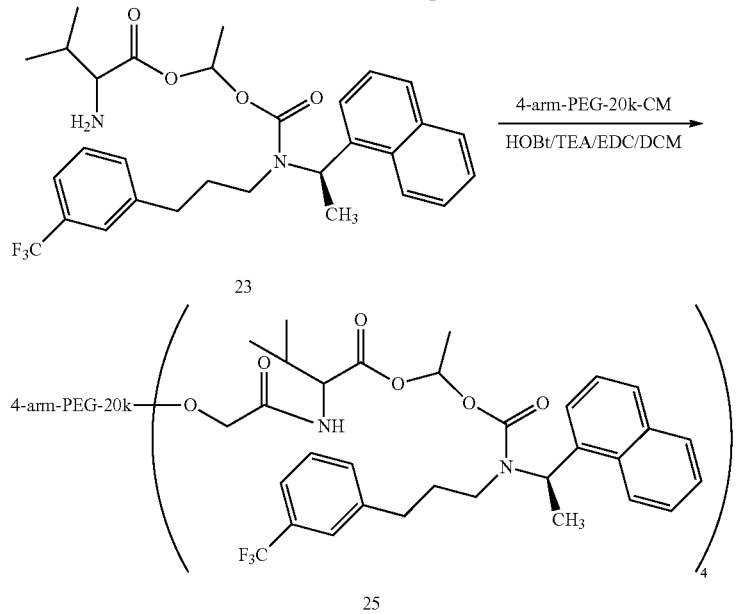

Four-arm-PEG$_{20k}$-CM (~1.2 g, ~0.059 mmol), L-valine-acyloxymethyl-carbamate-cinacalcet (23) (~180 mg, ~0.33 mmol), triethylamine (TEA, ~0.14 mL, ~100 mg, ~0.99 mmol) and 1-hydroxybenzotriazole (HOBt, ~47 mg, ~0.35 mmol) were dissolved in dichloromethane. N-ethyl-N'-(3-dimethylaminopropyl)carbodiimide (EDC, ~0.19 mL, ~154 mg, ~0.99 mmol) was then added. The reaction mixture was stirred at room temperature overnight (~24 hours). The product mixture was poured into 1:1 isopropanol/diethyl ether with strong stirring, the white precipitate was collected, washed with 1:1 isopropanol/diethyl ether and diethyl ether, and dried in vacuum. Four-arm-PEG$_{20k}$-L-valine-acyloxymethyl-carbamate-cinacalcet (25) was obtained as a white solid (~1.0 g, ~83% yield). HPLC analysis showed that there was no small molecule impurity and NMR indicated that the cinacalcet substitution was ~80%.

Example 11

Synthesis of mPEG$_{10k}$-D-Valine-Acyloxymethyl-Carbamate-Cinacalcet (28)

A compound that includes an amino acid-containing spacer moiety between a residue of cinacalcet and an oligomer was prepared following the schematic provided below.

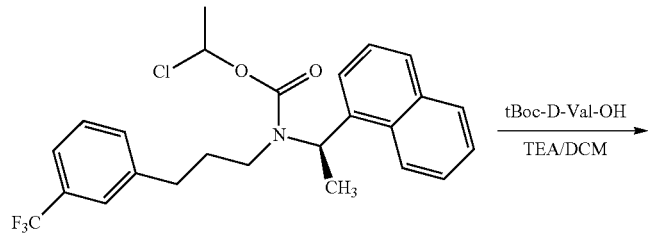

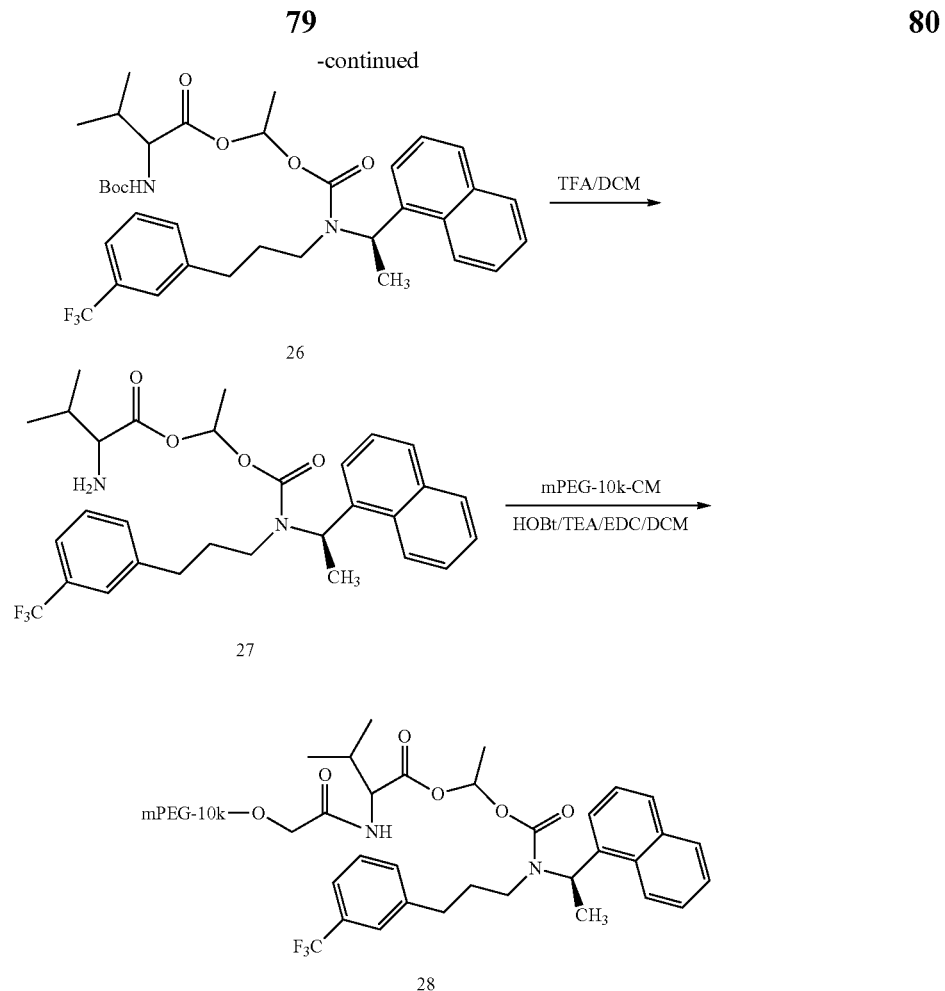

Synthesis of tBoc-D-valine-acyloxymethyl-carbamate-cinacalcet (26)

To a dichloromethane solution of 1-chloroethyl-carbamate-cinacalcet (17) (~670 mg, ~1.44 mmol) and tBoc-D-valine (~1.3 g, ~5.78 mmol) was added triethylamine (TEA, ~0.60 mL, ~438 mg, ~4.33 mmol). The reaction mixture was stirred at room temperature overnight (~20 hours), then washed with 0.1N HCl/NH$_4$Cl aqueous solution twice and NaCl aqueous solution once. The crude product was purified by chromatography with hexane/ethyl acetate; tBoc-D-valine-carbamate-cinacalcet (26) was obtained as a colorless liquid (~230 mg, ~0.36 mmol, ~25% isolated yield).

Synthesis of D-valine-acyloxymethyl-carbamate-cinacalcet (27)

To a dichloromethane solution of tBoc-D-valine-carbamate-cinacalcet (26) (~230 mg, ~0.36 mmol) was added trifluoroacetic acid (TFA) (~2 mL). The reaction mixture was stirred at room temperature for ~4.5 hours. The reaction was monitored by HPLC analysis for completion. The dichloromethane product mixture was washed with 0.1N HCl/NaCl aqueous solution three times. The dichloromethane phase was dried over Na$_2$SO$_4$. After solvent evaporation, D-valine-acyloxymethyl-carbamate-cinacalcet (27) was obtained as a white solid (~176 mg, ~91% isolated yield).

Synthesis of mPEG$_{10k}$-D-valine-acyloxymethyl-carbamate-cinacalcet (28)

mPEG$_{10k}$-CM (~1.1 g, ~0.11 mmol), D-valine-acyloxymethyl-carbamate-cinacalcet (27) (~88 mg, ~0.16 mmol), triethylamine (TEA, ~0.07 mL, ~49 mg, ~0.49 mmol) and 1-hydroxybenzotriazole (HOBt, ~23 mg, ~0.17 mmol) were dissolved in dichloromethane. N-ethyl-N'-(3-dimethylaminopropyl)carbodiimide (EDC, ~0.09 mL, ~75 mg, ~0.49 mmol) was then added. The reaction mixture was stirred at room temperature overnight (~18 hours). The product mixture was poured into 1:1 isopropanol/diethyl ether with strong stirring, the resulting white precipitate was collected, washed with 1:1 isopropanol/diethyl ether and diethyl ether, and dried in vacuum. mPEG$_{10k}$-D-valine-acyloxymethyl-carbamate-cinacalcet (28) was obtained as a white solid (~1.1 g, ~99% yield). HPLC analysis showed that there was no small molecule impurity and the cinacalcet substitution was ~89%.

Example 12

Synthesis of Multi-armed Oligomer-Cinacalcet (29)

A multi-armed oligomer-cinacalcet (also containing an amino acid-containing spacer moiety) was prepared in accordance with the schematic provided below.

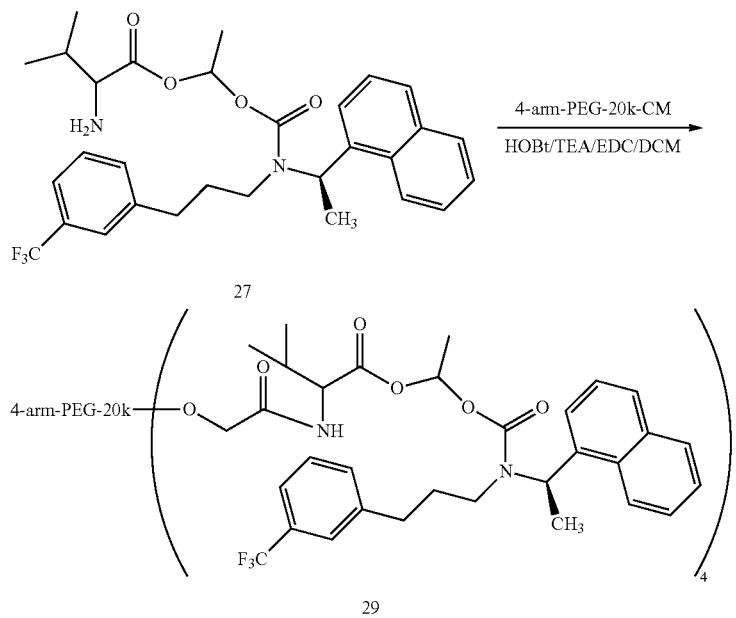

Four-arm-PEG$_{20k}$-CM (~582 mg, ~0.029 mmol), D-valine-acyloxymethyl-carbamate-cinacalcet (27) (~88 mg, ~0.16 mmol), triethylamine (TEA, ~0.07 mL, ~49 mg, ~0.49 mmol) and 1-hydroxybenzotriazole (HOBt, ~23 mg, ~0.17 mmol) were dissolved in dichloromethane. N-ethyl-N'-(3-dimethylaminopropyl)carbodiimide (EDC, ~0.09 mL, ~75 mg, ~0.49 mmol) was then added. The reaction mixture was stirred at room temperature for 41 hours. The product mixture was poured into 1:1 isopropanol/diethyl ether with strong stirring, the resulting white precipitate was collected, washed with 1:1 isopropanol/diethyl ether and diethyl ether, and dried in vacuum. Four-arm-PEG$_{20k}$-D-valine-acyloxymethyl-carbamate-cinacalcet (29) was obtained as a white solid (~550 mg, ~94% yield). HPLC analysis showed that there was no small molecule impurity and NMR indicated that the cinacalcet substitution was ~70%.

Example 13

Hydrolysis of Exemplary Compounds in pH 7.4 PBS Buffer

General procedure: ~5 mg of a compound of interest was dissolved in ~10 mL of pH 7.4 PBS buffer which contained ~12 mM phosphate and ~140 mM NaCl/KCl. The solution was placed into ten different HPLC vials and the HPLC vials were put into a 37° C. incubator. The samples were analyzed by HPLC at different timepoints. When hydrolysis occurred, HPLC confirmed that cinacalcet was released unaltered. The buffer half-lives $t_{1/2}$ of various PEG-cinacalcet conjugates are listed in Table 2.

TABLE 2

Hydrolysis of Tested Compounds in pH 7.4 PBS Buffer at 37° C.

| Compound Name | $t_{1/2}$ in PBS |
|---|---|
| mPEG$_{10k}$-L-leucine-acyloxymethyl-carbamate-cinacalcet (20), Example 7 | ~126 hours |
| mPEG$_{10k}$-D-valine-acyloxymethyl-carbamate-cinacalcet (28), Example 11 | ~208 hours |
| mPEG$_{10k}$-L-valine-acyloxymethyl-carbamate-cinacalcet (24), Example 9 | ~317 hours |
| mPEG$_{10k}$-L-isoleucine-acyloxymethyl-carbamate-cinacalcet (36), Example 25 | ~470 hours |
| mPEG$_{10k}$-glycine-amide-cinacalcet (15), Example 5 | stable |
| 4-Arm-PEG$_{20k}$-glycine-amide-cinacalcet (16), Example 6 | stable |

Example 14

Hydrolysis of Exemplary Compounds in an In Vivo Rat Study

The hydrolysis rates of exemplary compounds in an in vivo rat study was conducted. Briefly, cinacalcet hydrochloride was administered orally to four male rats to provide a cinacalcet equivalent dose of 10 mg/kg. For this cohort, blood was collected at the following time points: 0 (predose); 1, 2, 4, 6, 9, 12, 24, 48 and 72 hours following administration. Compound (15), Compound (20), Compound (16), Compound (21), Compound (24), Compound (25), Compound (28) and Compound (29), prepared in accordance with Examples, 5, 7, 6, 8, 9, 10, 11 and 12 respectively, were separately administered intravenously to four male rats to provide a cinacalcet equivalent dose of 1 mg/kg. Parent compound cinacalcet prepared in DMSO at 1 mg/kg was separately administrated intravenously to four male rats. For these cohorts, blood was collected at the following time points: 0 (predose), 2 minutes, 10 minutes, 1 hour, 2 hours, 4 hours, 8 hours, 24 hours, 48 hours and 72 hours following administration.

Figure 1B:
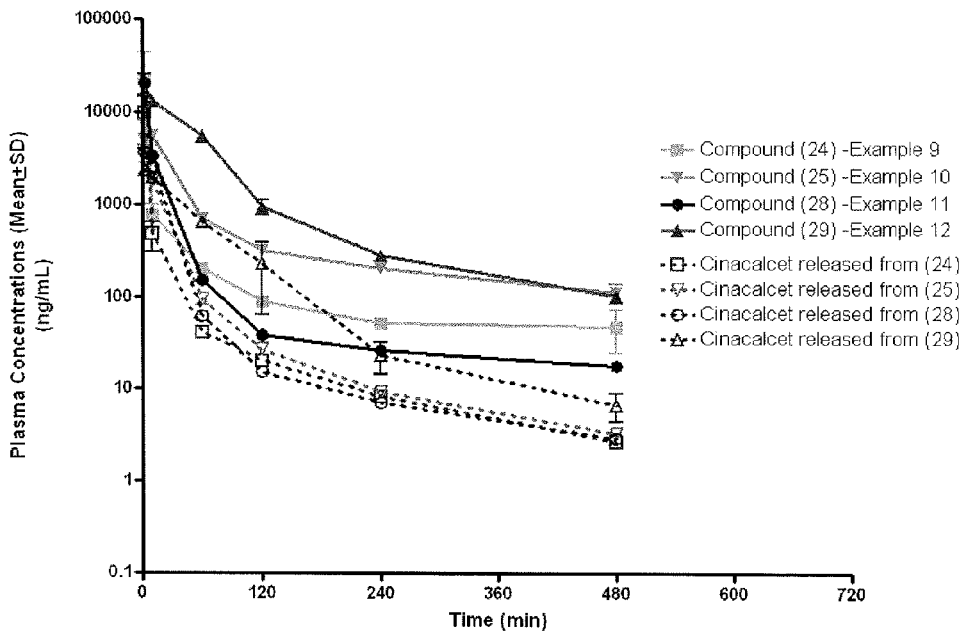

The results are provided in graph form in FIG. 1A and FIG. 1B, which show the plasma concentration-time profiles (averaged across the four rats) for the tested compounds.

Figure 2:
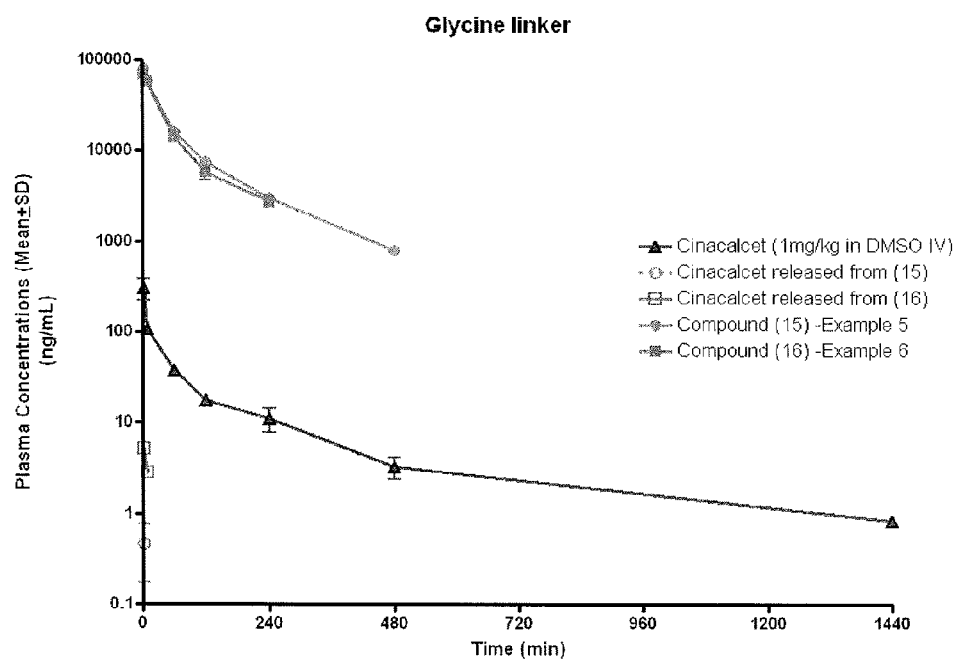
FIG. 2 is a graph showing plasma concentration-time profiles for exemplary compounds and released cinacalcet from the exemplary compounds, as further described in Example 14.

As shown in FIG. 2, comparisons of the plasma concentration-time profiles for released cinacalcet from each Compound (15) and Compound (16), Examples 5 and 6, respectively, and cinacalcet (unmodified) in DMSO after IV administration. In these two compounds using a glycine-based spacer moiety, only relatively low levels of cinacalcet (<10 ng/mL) release could be observed at earlier time points.

Figure 3:
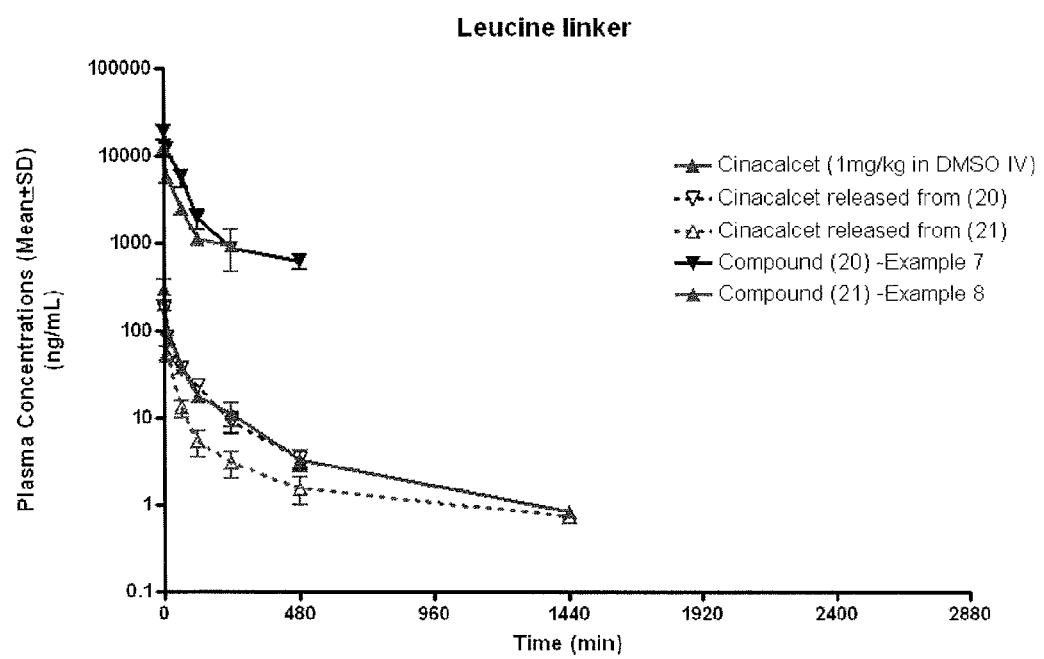
FIG. 3 is a graph showing plasma concentration-time profiles for exemplary compounds and released cinacalcet from the exemplary compounds, as further described in Example 14.

In FIG. 3, the plasma concentration-time profiles of Compound (20) and Compound (21), and the released cinacalcet from these two compounds were plotted with cinacalcet. In these two Compounds (20) and (21) using a leucine-based spacer moiety, relatively significant amounts of cinacalcet release were observed.

Figure 4:
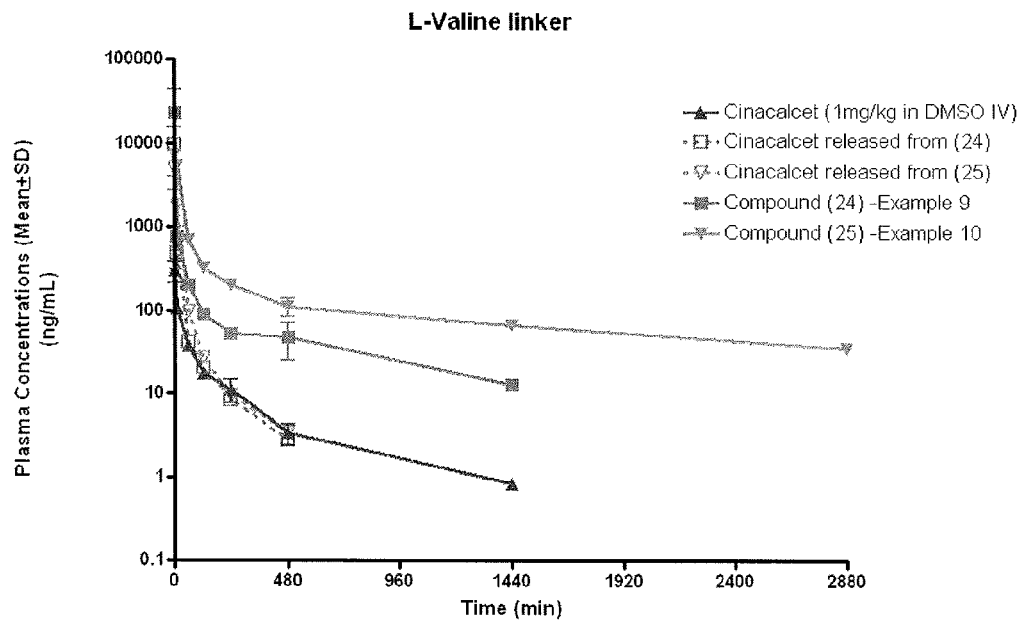
FIG. 4 is a graph showing plasma concentration-time profiles for exemplary compounds and released cinacalcet from the exemplary compound, as further described in Example 14.

In FIG. 4, the plasma concentration-time profiles of Compound (24) and Compound (25), and the released cinacalcet from these two compounds were plotted with cinacalcet. In these two Compounds (24) and (25) using a L-Valine-based spacer moiety, relatively significant amounts of cinacalcet release were observed.

Figure 5:
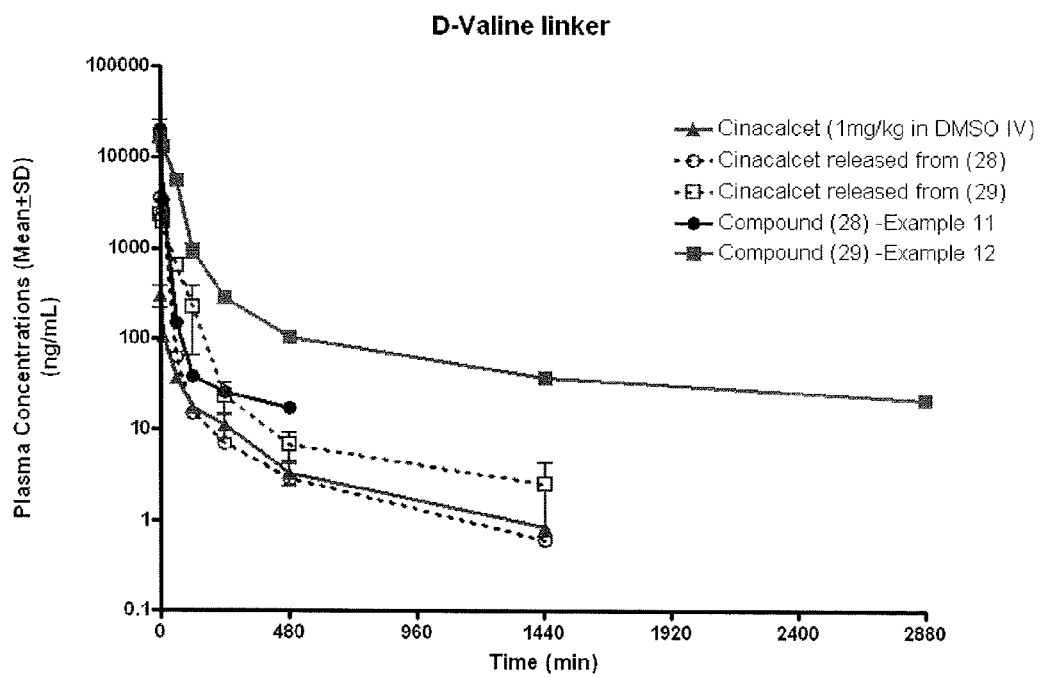
FIG. 5 is a graph showing plasma concentration-time profiles for exemplary compounds and released cinacalcet from the exemplary compound, as further described in Example 14.

In FIG. 5, the plasma concentration-time profiles of Compound (28) and Compound (29), and the released cinacalcet from these two compounds were plotted with cinacalcet. In these two Compounds (28) and (29) using a D-Valine-based spacer moiety, relatively significant amounts of cinacalcet release were observed.

Standard pharmacokinetic parameters were also determined for each of Compound (20) and Compound (21), Examples 7 and 8, respectively, and cinacalcet (unmodified) and are set forth in Table 3.

TABLE 3

Pharmacokinetic Parameters of Compound (20), Compound (21) and Cinacalcet

| PK Parameter | Compound (20) (Example 7) (1 mg/kg, IV) | | Compound 21 (Example 8) (1 mg/kg, IV) | | Cinacalcet (10 mg/kg, PO) | |
|---|---|---|---|---|---|---|
| | Mean | SD | Mean | SD | Mean | SD |
| AUCall (min*ng/mL) | 11200 | 2210 | 5730 | 2220 | 41400 | 10100 |
| Clearance (mL/min/kg) | 100 | 21.1 | 206 | 91.6 | — | |
| $C_{max}$ (ng/mL) | 178 | 45.8 | 200 | 58.8 | 97.4 | 14.2 |
| $T_{1/2}$ (min) | 139 | 38.8 | 280 | 143 | 179 | 34.8 |
| $V_{ss}$ (mL/kg) | 13600 | 2840 | 28000 | 8930 | — | |

In view of this data, it can be concluded that Compounds (15) and (16) shown substantially no release of cinacalcet after intervenous administration. With respect to Compounds (20), (21) (24), (25), (28) and (29), however, release of cinacalcet continues for up to about 8-12 hours following intravenous administration. In addition, Compound (20) showed approximately 2-fold higher exposure and approximately equal $C_{max}$ compared to Compound (21), which had a four-arm oligomer. Compound (21), however, appears to have 2-fold longer $t_{1/2}$ and 2-fold higher clearance and volume of distribution ($V_{SS}$) compared to Compound (20).

Thus, depending on the desired pharmacokinetic profile, the exemplary compounds provide a range of dosing options.

Example 15

In Vitro Screen—HEK 293 Cells

Using conventional techniques, human embryonic kidney cells (HEK 293 cells) are engineered to express the human parathyroid calcium sensing receptor (CaR). These cells can detect allosteric activators (calcimimetics) of the CaR using changes in cytoplasmic Ca2+ concentrations as an endpoint (flipper assay). Changes in cytoplasmic Ca2+ concentrations provide a quantitative and functional assessment of CaR activity in these cells. Compounds of the invention are tested using this in vitro model and are shown to function as calicimimetics.

Example 16

In Vitro Screen—Dissociated Parathyroid Cells

An in vitro screening based on CaR-dependent regulation of PTH secretion is used to test compounds of the invention. Primary cultures of dissociated bovine parathyroid cells are prepared and aliquots of compounds of the invention are allowed to come into contact with the prepared cells. PTH secretion in the presence of a compound of invention is then compared against a control. Compounds of the invention are tested using this in vitro model and are shown to function as calicimimetics.

Example 17

In Vivo Screen—PTH-lowering Effects in Normal Rats

PEG-Cinacalcet calcimmetic effects were studied in PTH (parathyroid hormone)-lowering experiments in normal rats. Male SD rats (~350 g) were IV dosed with different compounds at 1 mg/kg or orally ("PO") cinacalcet at 10 mg/kg. Plasma samples were collected and prepared at different timepoints (up to 72 hours) after drug administration. The plasma PTH levels were quantified by ELISA. Compounds of the invention were tested using this model and are shown to function as calicimimetics.

Figure 6:
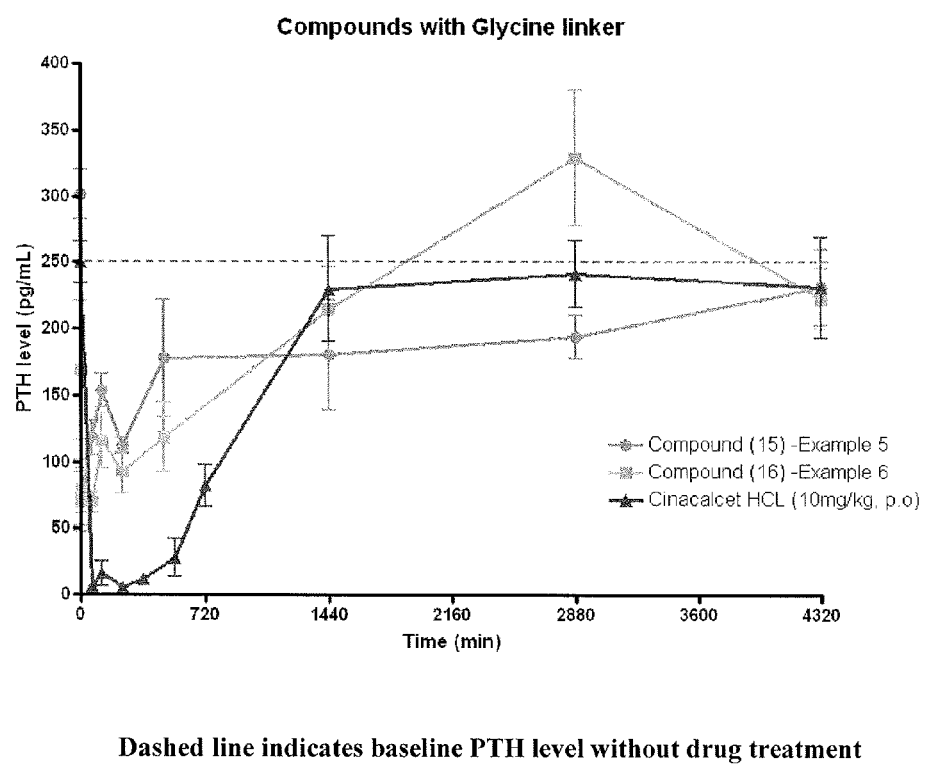
FIG. 6 is a graph of rat plasma PTH levels following administration of cinacalcet (10 mg/kg, po) and exemplary compounds (1 mg/kg, IV), as further described in Example 17.

In FIG. 6 are rat plasma PTH levels after cinacalcet (PO, 10 mg/kg) or Compounds (15) and (16) (IV, 1 mg/kg) treatments. At 10 mg/kg, parent cinacalcet oral treatment produced a PTH-lowering effect up to ~12 hours. Although Compound (15) and (16) did not show significant cinacalcet release in the earlier studies, both compounds showed PTH-lowering effects from 2 minutes to 8 hours after drug administration.

Figure 7:
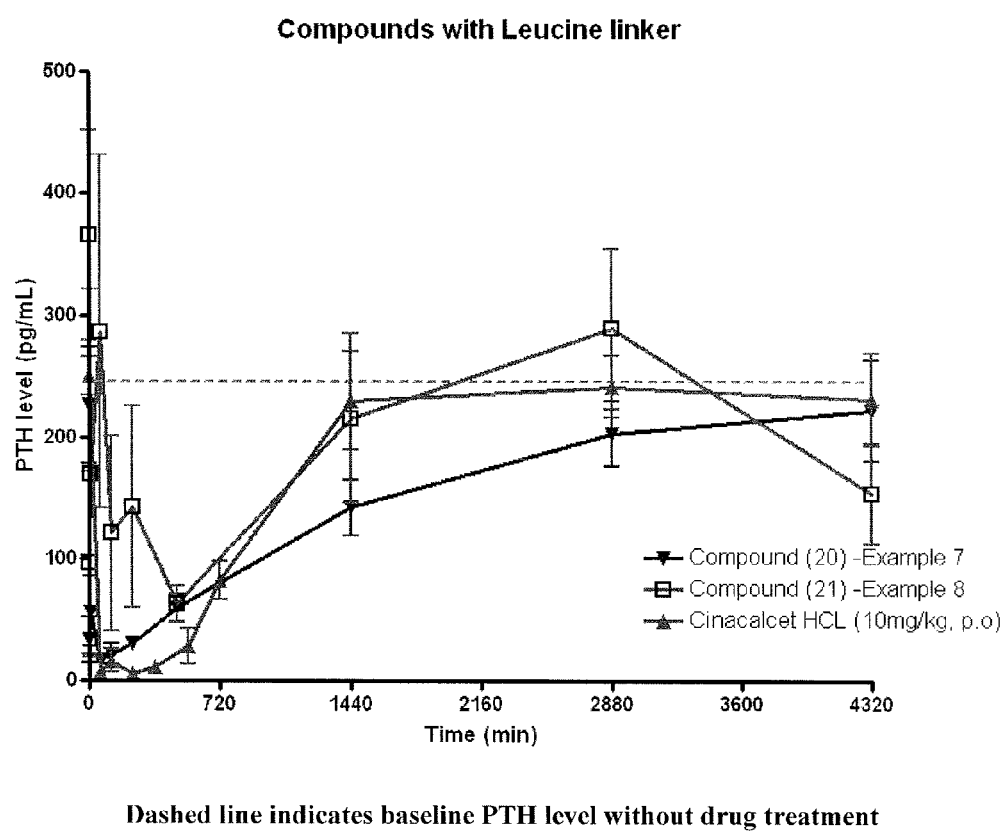
FIG. 7 is a graph of rat plasma PTH levels following administration of cinacalcet (10 mg/kg, po) and exemplary compounds (1 mg/kg, IV), as further described in Example 17.

In FIG. 7 are rat plasma PTH levels after cinacalcet (PO, 10 mg/kg) or Compounds (20) and (21) (IV, 1 mg/kg) treatments. Both compounds showed significant PTH-lowering effects. Compound (20) in particular exhibited prolonged PTH-lowering effects up to ~24-48 hours.

Figure 8:
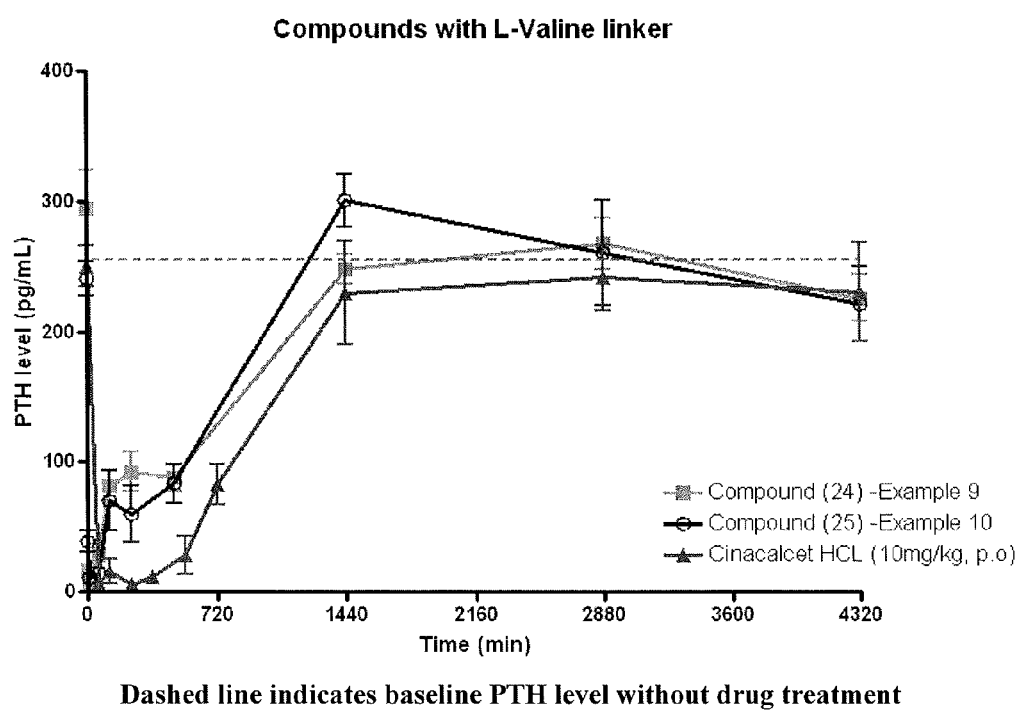
FIG. 8 is a graph of rat plasma PTH levels following administration of cinacalcet (10 mg/kg, po) and exemplary compounds (1 mg/kg, IV), as further described in Example 17.
Figure 9:
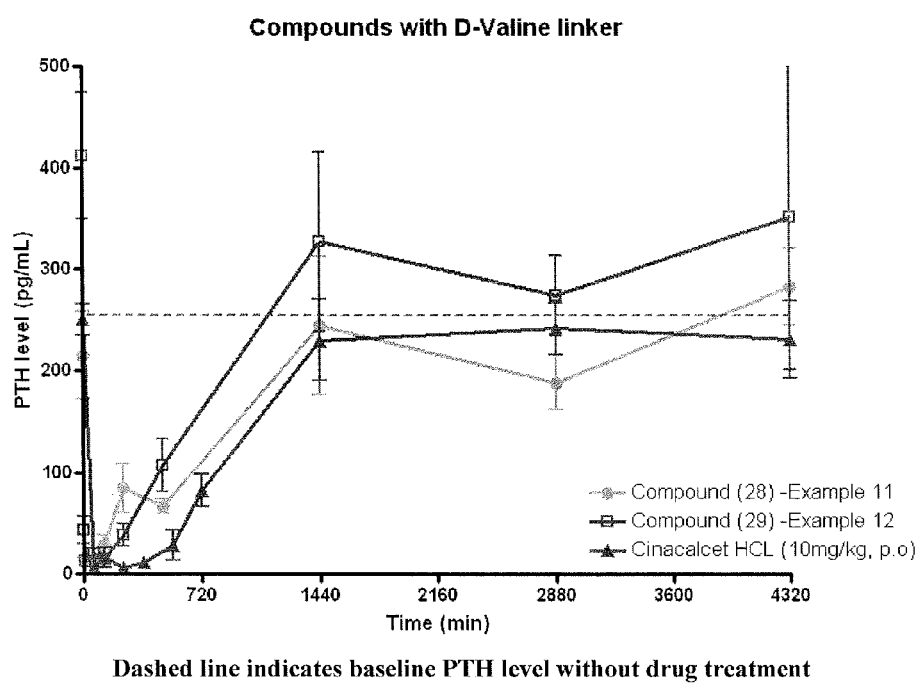
FIG. 9 is a graph of rat plasma PTH levels following administration of cinacalcet (10 mg/kg, po) and exemplary compounds (1 mg/kg, IV), as further described in Example 17.

In FIG. 8 are rat plasma PTH levels after cinacalcet (PO, 10 mg/kg) or Compounds (24) and (25) (IV, 1 mg/kg) treatments. In FIG. 9 are rat plasma PTH levels after cinacalcet (PO, 10 mg/kg) or Compounds (28) and (29) (IV, 1 mg/kg) treatments. All compounds showed variable PTH-lowering effects, with the animal PTH levels returning to baseline at ~24 hrs.

In summary, PTH-lowering effects of PEG-Cinacalcet compounds were tested in normal rats. The effects were dependent on different linkers and PEG structures being used. Compound (20) in particular exhibited prolonged PTH-lowering effect up to ~24-48 hours in this test, comparing to parent cinacalcet at 10 mg/kg PO that only exhibited PTH-lowering effects up to ~12 hours after dosing.

Example 18

In Vivo Screen—Rat Chronic Renal Insufficiency (CRI) Model

Figure 10A:
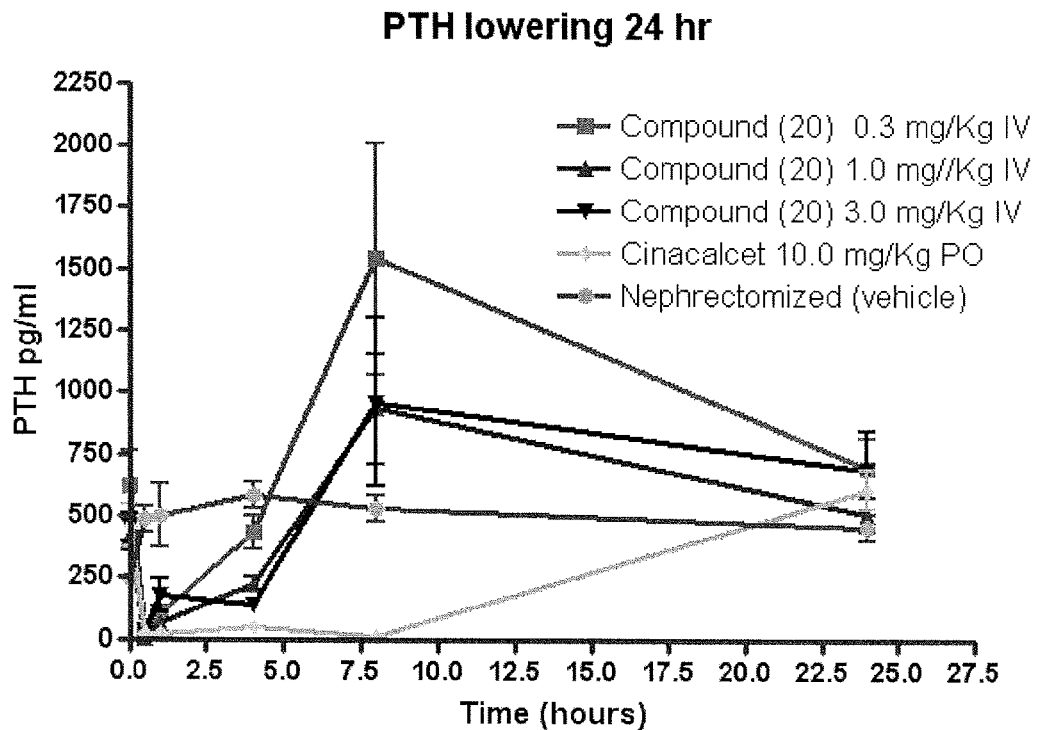
FIG. 10A is a graph of rat plasma PTH levels in a rat model of chronic renal insufficiency following administration of cinacalcet and an exemplary compound, as further described in Example 18.
Figure 10B:
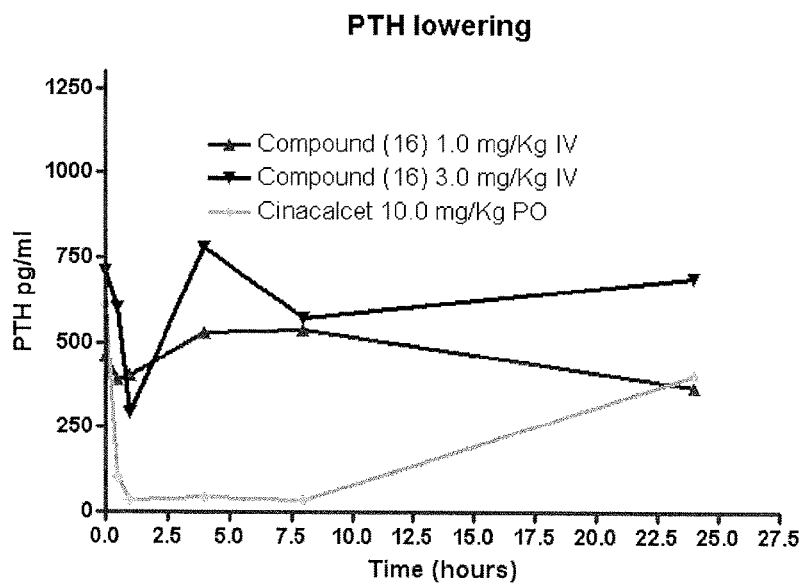
FIG. 10B is a graph of rat plasma PTH levels in a rat model of chronic renal insufficiency following administration of cinacalcet and an exemplary compound, as further described in Example 18.
Figure 10C:
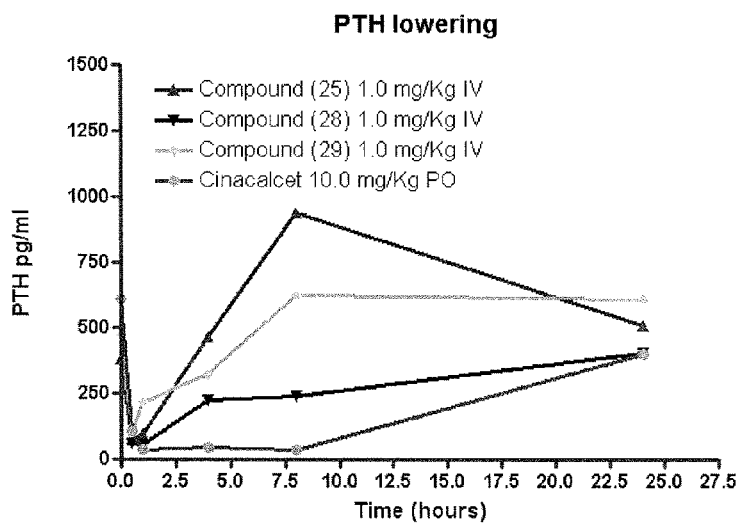
FIG. 10C is a graph of rat plasma PTH levels in a rat model of chronic renal insufficiency following administration of cinacalcet and exemplary compounds, as further described in Example 18.

The approach set forth in Example 14 is repeated except rats were surgically modified to mimic chronic renal insufficiency through the total removal of one kidney and ⅔ of the other kidney (a ⅚ nephrectomy or "⅚Nx"). Each compound was tested 6-8 weeks post 5/6 nephrectomy surgery after renal insufficiency had been established. Parathyroid hormone levels in normal rats are around 100 pg/ml and in ⅚ Nx rats they increase to 500-1000 pg/ml. Compounds of the invention are tested using this model and are shown to function as calicimimetics, with the potential to be used in chronic kidney disease. FIG. 10A is a plot of PTH (pg/ml) vs. time for cinacalcet and Compound (20). FIG. 10B is a plot of PTH (pg/ml) vs. time for cinacalcet and Compound (16). FIG. 10C is a plot of PTH (pg/ml) vs. time for cinacalcet, Compound (25), Compound (28), and Compound (29). Compared to the other tested compounds, Compound (16) contains a stable linker, which results in a diminished or no release of cinacalcet. As such, PTH levels are not reduced as significantly as Compounds (25), (28), and (29).

Example 19

In Vivo Screen—Rat Parathyroid Hyperplasia Model

5/6 Nx modified rats also mimics parathyroid hyperplasia. As such, compounds of the invention are tested in 5/6 nephrectimized rats and are shown to have potential as decreasing parathyroid hyperplasia (through parathyroid cell proliferation and gland size by removing the parathyroid gland at the end of the study, weighed, sectioned and stained for p21.

Example 20

Preparation of Compound 1 (Used in Example 3)

Compound 1 can be prepared using the schematic set forth below, wherein reaction conditions of temperature, amounts, time, pH, solvents and the like will be known to one of ordinary skill in the art upon a review of this schematic and the disclosure provided herein.

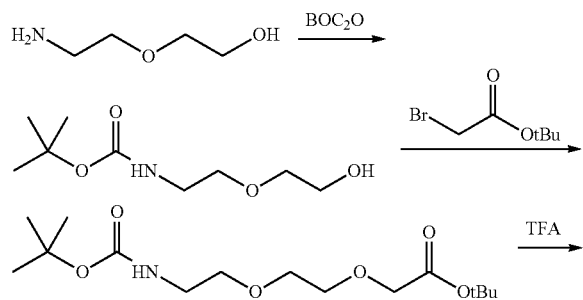

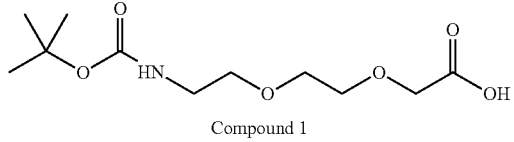

Compound 1

In addition, following this same general approach, $H_2N$—$CH_2CH_2(OCH_2CH_2)_n$—$OH$, wherein n is defined as something other than 1 and as otherwise defined herein (e.g., 2, 3, 4, 5, 6, 7, 8, 9, 10 or more) can be used, to provide $(CH_3)_3$—$OC(O)$—$NH$—$CH_2CH_2$—$O(OCH_2CH_2)_n$—$O$—$CH_2$—$C(O)OH$, wherein n is defined as something other than 1 and as otherwise defined herein (e.g., 2, 3, 4, 5, 6, 7, 8, 9, 10 or more).

Example 21

Synthesis of mPEG$_{20k}$-L-Leucine-Acyloxymethyl-Carbamate-Cinacalcet (30)

A compound that includes an amino acid-containing spacer moiety between a residue of cinacalcet and an oligomer was prepared following the schematic provided below.

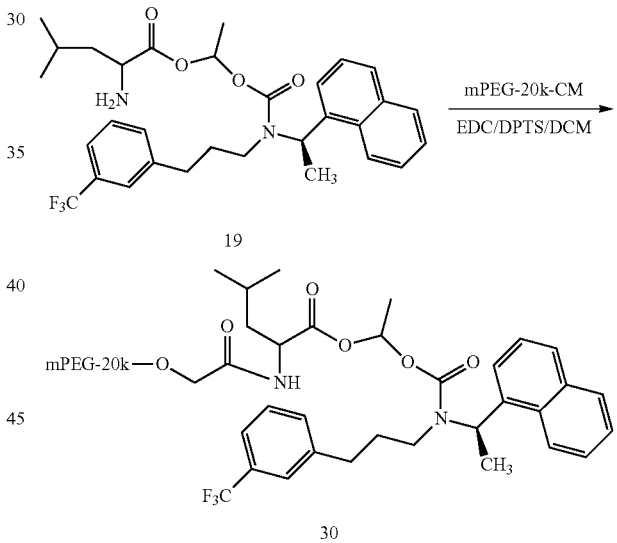

mPEG$_{20k}$-CM (~4.4 g, ~0.22 mmol), L-leucine-acyloxymethyl-carbamate-cinacalcet (19) (~176 mg, ~0.31 mmol) and 4-N,N-dimethylaminopyridinium p-tolunesulfonate (DPTS, ~95 mg, ~0.31 mmol) were dissolved in dichloromethane. N-ethyl-N'-(3-dimethylaminopropyl) carbodiimide (EDC, ~0.17 mL, ~146 mg, ~0.94 mmol) was then added. The reaction mixture was stirred at room temperature overnight (~23 h). The product mixture was poured into 1:1 isopropanol/diethyl ether with strong stirring, the resulting white precipitate was collected, washed with 1:1 isopropanol/diethyl ether and diethyl ether, and dried in vacuum. mPEG$_{20k}$-L-leucine-acyloxymethyl-carbamate-cinacalcet (30) was obtained as a white solid (~3.8 g, ~87% yield). HPLC analysis showed that there was no small molecule impurity. NMR indicated that the cinacalcet substitution was ~86%.

Example 22

Synthesis of Multi-armed Oligomer-Cinacalcet (31)

A multi-armed oligomer-cinacalcet (also containing an amino acid-containing spacer moiety) was prepared in accordance with the schematic provided below.

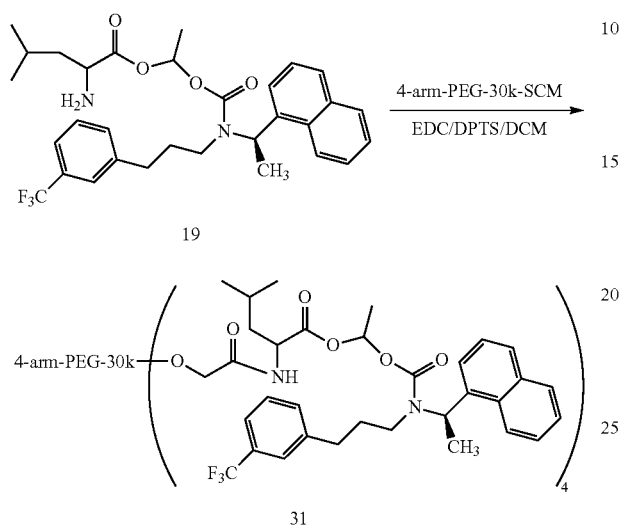

Example 23 (Prophetic)

Synthesis of mPEG$_{10k}$-D-Leucine-Acyloxymethyl-Carbamate-Cinacalcet (32)

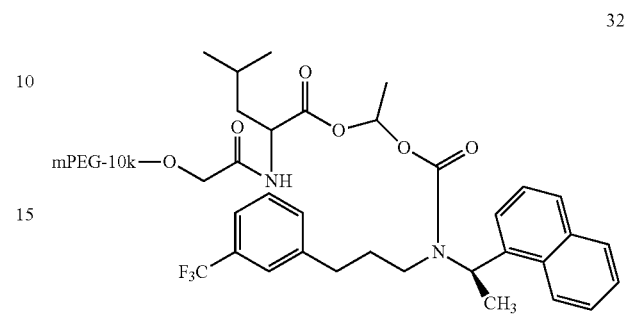

The compound (32) is prepared by modifying Example 7. Particularly, t-Boc-L-leucine is replaced with t-Boc-D-leucine. The reaction scheme otherwise follows that of Example 7.

Example 24 (Prophetic)

Synthesis of 4-arm-PEG-20k-D-Leucine-acyloxymethyl-carbamate-cinacalcet (33)

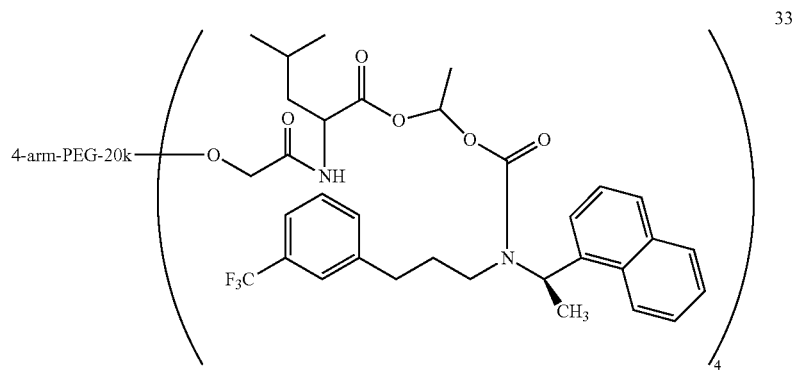

Four-arm-PEG$_{30k}$-SCM (~1.7 g, ~0.056 mmol), L-leucine-acyloxymethyl-carbamate-cinacalcet (19) (~180 mg, ~0.32 mmol) and 4-N,N-dimethylaminopyridinium p-toluenesulfonate (DPTS, ~97 mg, ~0.32 mmol) were dissolved in dichloromethane. N-ethyl-N'-(3-dimethylaminopropyl)carbodiimide (EDC, ~0.17 mL, ~150 mg, ~0.97 mmol) was then added. The reaction mixture was stirred at room temperature overnight (~23 hours). The product mixture was poured into 1:1 isopropanol/diethyl ether with strong stirring, the resulting white precipitate was collected, washed with 1:1 isopropanol/diethyl ether and diethyl ether, and dried in vacuum. Four-arm-PEG$_{30k}$-L-leucine-acyloxymethyl-carbamate-cinacalcet (31) was obtained as a white solid (~1.58 g, ~84% yield). HPLC analysis showed that there was no small molecule impurity and the cinacalcet substitution was ~90%.

The compound (33) is prepared by modifying Example 8. Particularly, L-leucine-acyloxymethyl-carbamate-cinacalcet (19) is replaced with D-leucine-acyloxymethyl-carbamate-cinacalcet. The reaction scheme otherwise follows that of Example 8.

Example 25

Synthesis of mPEG$_{10k}$-L-Isoleucine-Acyloxymethyl-Carbamate-Cinacalcet (36)

A compound that includes an amino acid-containing spacer moiety between a residue of cinacalcet and an oligomer was prepared following the schematic provided below.

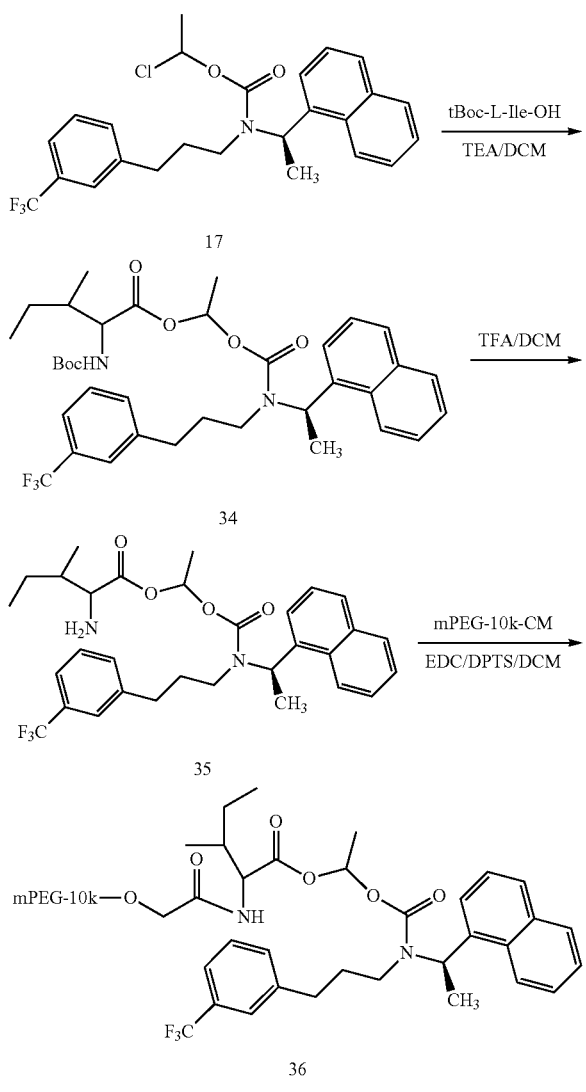

hours. The reaction was monitored by HPLC analysis for completion. The dichloromethane product mixture was washed with 0.1N HCl/NaCl aqueous solution three times. The dichloromethane phase was dried over $Na_2SO_4$. After solvent evaporation, L-isoleucine-acyloxymethyl-carbamate-cinacalcet (35) was obtained as a white solid (~0.45 g, ~0.81 mmol, ~84% isolated yield).

Synthesis of mPEG$_{10k}$-L-isoleucine-acyloxymethyl-carbamate-cinacalcet (36)

mPEG$_{10k}$-CM (~2.8 g, ~0.28 mmol), L-isoleucine-acyloxymethyl-carbamate-cinacalcet (35) (~221 mg, ~0.40 mmol) and 4-N, N-dimethylaminopyridinium p-tolunesulfonate (DPTS, ~119 mg, ~0.40 mmol) were dissolved in dichloromethane. N-ethyl-N'-(3-dimethylaminopropyl) carbodiimide (EDC, ~0.21 mL, ~184 mg, ~1.19 mmol) was then added. The reaction mixture was stirred at room temperature overnight (~21 hours). The product mixture was poured into 1:1 isopropanol/diethyl ether with strong stirring, the resulting white precipitate was collected, washed with 1:1 isopropanol/diethyl ether and diethyl ether, and dried in vacuum. mPEG$_{10k}$-L-isoleucine-acyloxymethyl-carbamate-cinacalcet (36) was obtained as a white solid (~2.8 g, ~99% yield). HPLC analysis showed that there was no small molecule impurity. Cinacalcet substitution was ~79% by NMR measurement.

Example 26

Synthesis of 4-Arm-PEG-20k-L-Isoleucine-Acyloxymethyl-Carbamate-Cinacalcet (37)

A multi-armed oligomer-cinacalcet (also containing an amino acid-containing spacer moiety) was prepared in accordance with the schematic provided below.

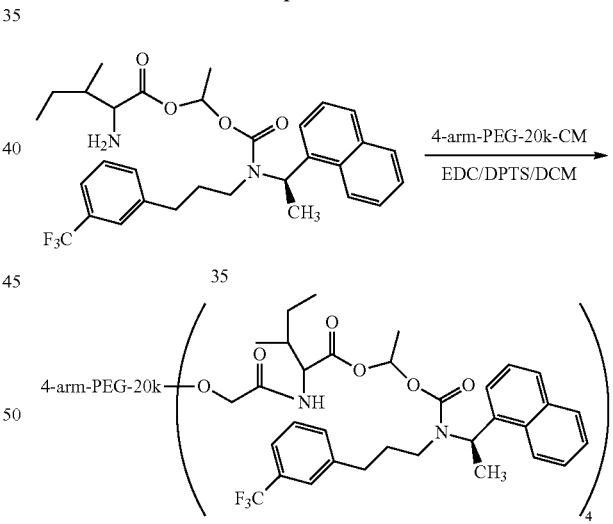

Synthesis of tBoc-L-isoleucine-acyloxymethyl-carbamate-cinacalcet (34)

To a dichloromethane solution of 1-chloroethyl-carbamate-cinacalcet (17) (~0.99 g, ~2.13 mmol) and tBoc-L-isoleucine (~4.94 g, ~21.3 mmol) was added triethylamine (TEA, ~2.4 mL, ~1.73 g, ~17.1 mmol). The reaction mixture was stirred at 36° C. overnight (~22 hours), HPLC showed that the reaction was complete. To the product mixture was added dichloromethane and washed with 0.1N HO/NH$_4$Cl aqueous solution twice and NaCl aqueous solution once. The crude product was purified by chromatography with hexane/ethyl acetate; tBoc-L-isoleucine-acyloxymethyl-carbamate-cinacalcet (34) was obtained as a colorless liquid (~0.63 g, ~0.96 mmol, ~45% isolated yield).

Synthesis of L-isoleucine-acyloxymethyl-carbamate-cinacalcet (35)

To a dichloromethane solution of tBoc-L-isoleucine-acyloxymethyl-carbamate-cinacalcet (34) (~0.63 g, ~0.96 mmol) was added trifluoroacetic acid (TFA) (~1.5 mL). The reaction mixture was stirred at room temperature for ~5

Four-arm-PEG$_{20k}$-CM (~1.5 g, ~0.074 mmol), L-isoleucine-acyloxymethyl-carbamate-cinacalcet (35) (Example 25) (~235 mg, ~0.42 mmol) and 4-N,N-dimethylaminopyridinium p-tolunesulfonate (DPTS, ~126 mg, ~0.42 mmol) were dissolved in dichloromethane. N-ethyl-N'-(3-dimethylaminopropyl) carbodiimide (EDC, ~0.23 mL, ~196 mg, ~1.26 mmol) was then added. The reaction mixture was stirred at room temperature for ~22 hours. The product mixture was poured into 1:1 isopropanol/diethyl ether with strong stirring, the resulting white precipitate was collected, washed with 1:1 isopropanol/diethyl ether and diethyl ether, and dried in vacuum. Four-arm-PEG$_{20k}$-L-isoleucine-acyloxymethyl-carbamate-cinacalcet (37) was obtained as a white solid (~1.3 g, ~85% yield). HPLC analysis showed that there was no small molecule impurity and NMR indicated that the cinacalcet substitution was ~79%.

Example 27

Hydrolysis of Compound (31) in an In Vivo Dog Study

Figure 11:
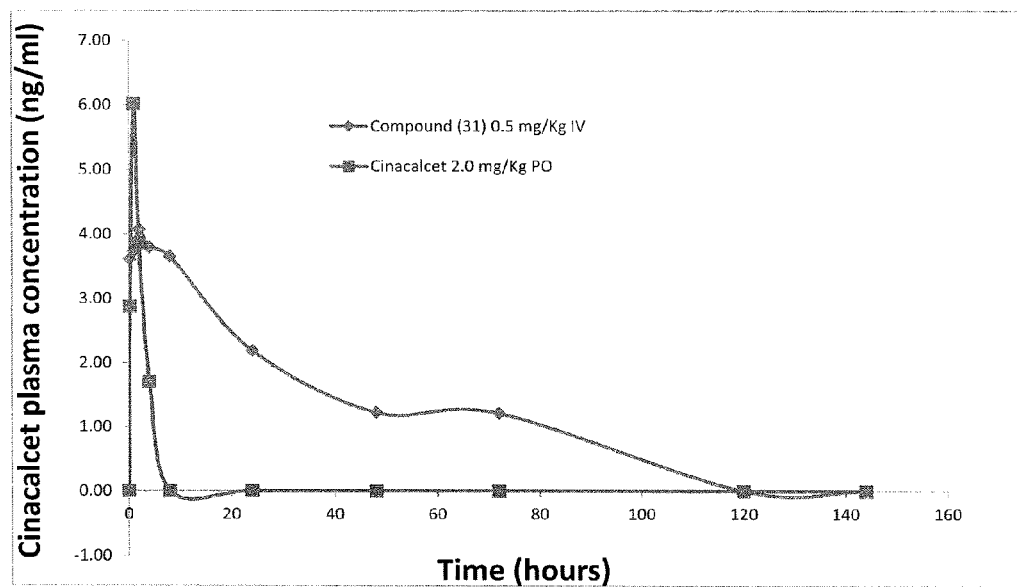
FIG. 11 is a graph of cinacalcet plasma concentration (ng/ml) over time for cinacalcet and an exemplary compound, as further described in Example 27.

The hydrolysis rates of exemplary compounds in an in vivo dog study was conducted, similar to that described in Example 14. Briefly, cinacalcet hydrochloride was administered orally to three male beagle dogs to provide a cinacalcet equivalent dose of 2.0 mg/kg. Compound (31), prepared in accordance with Example 22, was separately administered intravenously to three male beagle dogs to provide a cinacalcet equivalent dose of 0.5 mg/kg. For both the cohorts, blood was collected at the following time points: 0 (predose); 10 min, 1, 2, 4, 8, 24, 48, 72, 120 and 144 h. The results are provided in graph form in FIG. 11 which shows the plasma concentration-time profiles (averaged across the three dogs) for the tested compound.

Standard pharmacokinetic parameters were also determined for Compound (31) and cinacalcet (unmodified) and are set forth in Table 4. Thus it was observed that Compound (31) releases therapeutically relevant levels of cinacalcet up to 72 hours, suggesting a PK profile suitable for three times a week dosing. Half-life was increased and Cmax was blunted.

TABLE 4

| PK Parameter | Test Article | | | |
|---|---|---|---|---|
| | Compound (31) (1 mg/kg, IV) | | Cinacalcet (10 mg/kg, PO) | |
| | Mean | SD | Mean | SD |
| AUCall (hr*ng/mL) | 176 | 7.02 | 17.8 | 5.00 |
| Clearance (mL/hr/kg) | 2600 | 38.1 | 112000 | 32100 |
| $C_{max}$ (ng/mL) | 4.08 | 0.401 | 6.01 | 2.34 |
| $T_{1/2}$ (min) | 25.9 | 3.59 | 1.77 | 0.304 |
| Vz(F) (mL/kg) | 97200 | 12500 | 294000 | 134000 |

Example 28

In Vivo Screen—PTH-lowering Effects in Normal Rats of Compound (30) and Compound (31)

Figure 12:
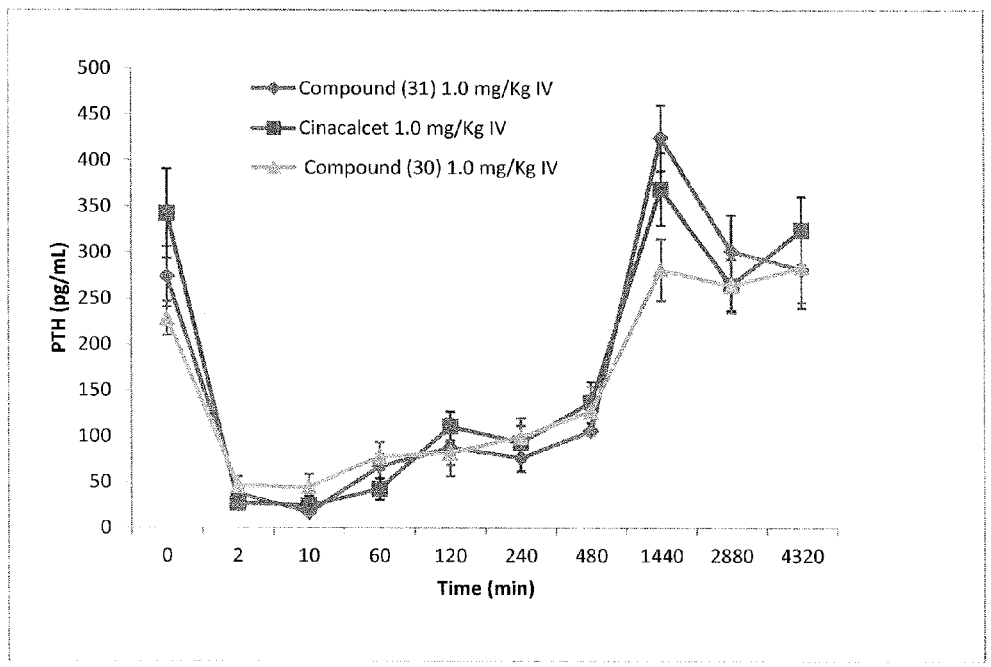
FIG. 12 is a graph of PTH (pg/ml) levels over time for exemplary compounds, as further described in Example 28.

PEG-Cinacalcet calcimmetic effects were studied in PTH (parathyroid hormone)-lowering experiments in normal rats for Compound (30) and Compound (31) as described in Example 17. FIG. 12 is a plot of PTH (pg/ml) levels over time for the presently tested compounds.

Example 29

Figure 13:
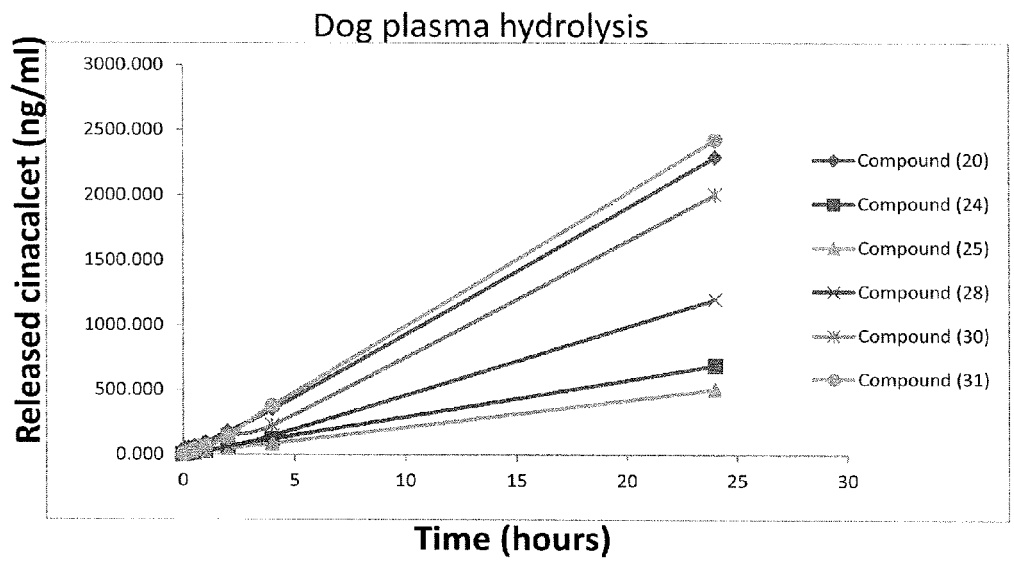
FIG. 13 is a graph of the released cinacalcet (ng/ml) over time (hr) in dog plasma for exemplary compounds, as further described in Example 29.
Figure 14:
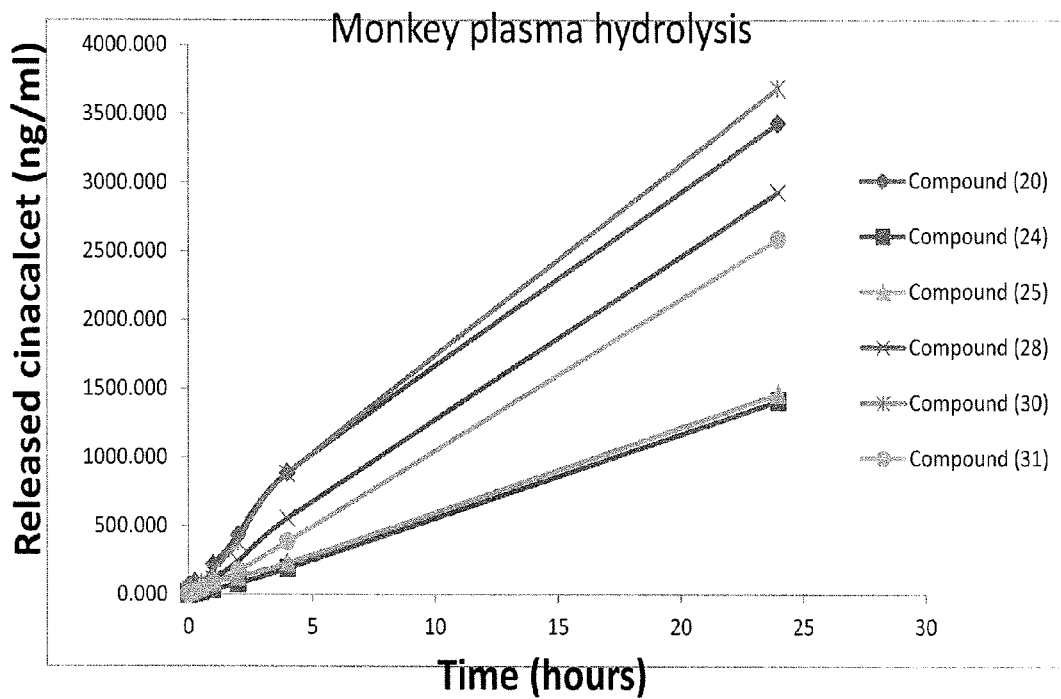
FIG. 14 is a graph of the released cinacalcet (ng/ml) over time (hr) in monkey plasma for exemplary compounds, as further described in Example 29.
Figure 15:
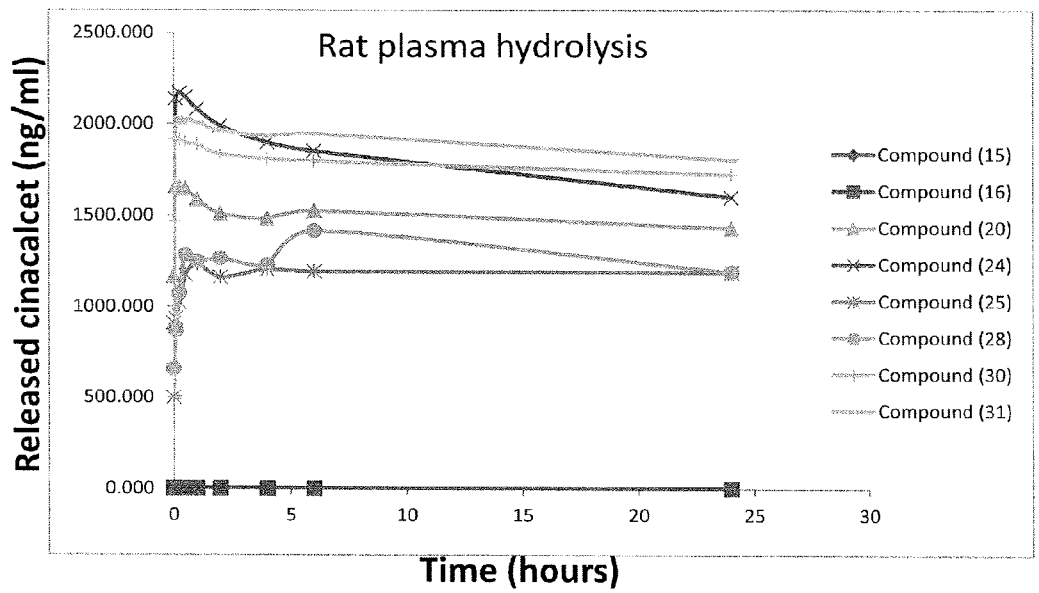
FIG. 15 is a graph of the released cinacalcet (ng/ml) over time (hr) in rat plasma for exemplary compounds, as further described in Example 29.
Figure 16:
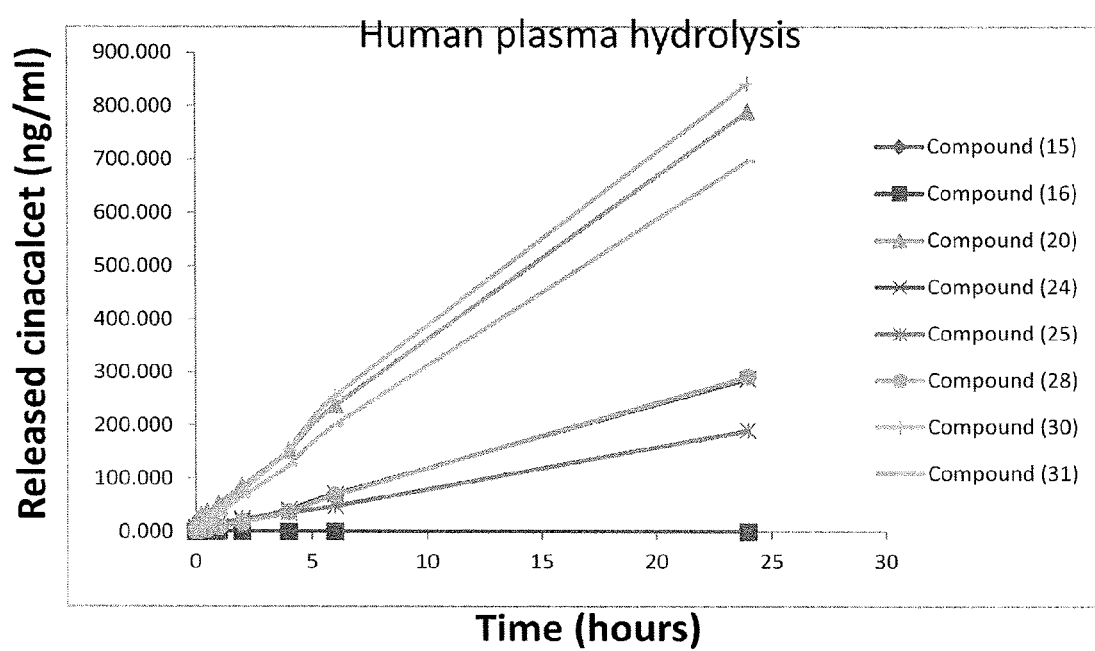
FIG. 16 is a graph of the released cinacalcet (ng/ml) over time (hr) in human plasma for exemplary compounds, as further described in Example 29.

Hydrolysis Studies of Certain Compounds of the Present Invention in Rat, Dog, Monkey and Human Plasma Certain compounds of the present invention and parent cinacalcet were added to 2.0 mL of untreated rat, dog, monkey or human plasma to obtain 5000 ng/mL of PEG-Cinacalcet derivatives (Cinacalcet equivalent concentration). Samples were incubated in a shaking water bath at 37° C. Aliquots were withdrawn at time points: 0, 5, 15, 30, 60, 120, 240 minutes and 24 hr, spiked with stabilizers (sodium fluoride (NaF), PMSF and Acetic Acid) and analyzed. FIG. 13 is a plot of the released cinacalcet (ng/ml) over time (hr) in dog plasma. FIG. 14 is a plot of the released cinacalcet (ng/ml) over time (hr) in monkey plasma. FIG. 15 is a plot of the released cinacalcet (ng/ml) over time (hr) in rat plasma. FIG. 16 is a plot of the released cinacalcet (ng/ml) over time (hr) in human plasma.

The compounds released cinacalcet much faster in rat plasma as compared to dog, monkey and human. This is most likely due to high levels of esterases in rat plasma. Slower release in higher species indicates release rates favorable for a long half-life and less frequent dosing.

What is claimed is:

1. A compound according to Formula II-Ce:

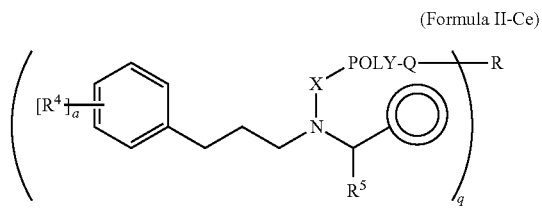

(Formula II-Ce)

or a pharmaceutically acceptable salt or solvate thereof, wherein:

◎ is 3-methoxyphenyl, 3-chlorophenyl or 1-naphthyl;
each $R^4$ is independently —H, —F, —Cl, —Br, —I, phenyl, —CF$_3$, —CF$_2$H, —CFH$_2$, lower alkyl, —O-lower alkyl, —OCH$_2$CF$_3$, —OH, —CN, —NO$_2$, —C(O)-lower alkyl, —C(O)O-lower alkyl, —C(O)NH-lower alkyl, —C(O)N-(lower alkyl)$_2$, —OC(O)-lower alkyl, or —NH—C(O)-lower alkyl;
a is an integer from 1 to 5;
$R^5$ is lower alkyl;
R is a residue of polyol, polythiol or polyamine bearing from 3 to about 50 hydroxyl, thiol or amino groups;
POLY is a water-soluble, non-peptidic polymer;
each of X and Q is independently —(CR$_x$R$_y$)$_{a'}$—K$_w$—(CR$_x$R$_y$)$_b$—(CH$_2$CH$_2$O)$_c$—(CR$_x$R$_y$)$_d$—K$_z$—, an amino acid residue, or combination thereof;
each of R$_x$ and R$_y$, in each occurrence, is independently H, alkyl substituted alkyl, alkenyl, substituted alkenyl, alkynyl, substituted alkynyl, aryl or substituted aryl;
each of K$_w$ and K$_z$ is independently —NH—, —C(O)—, —C(O)NH—, —NHC(O)—, —O—, —S—, —OC(O)—, —C(O)O—, —OC(O)O—, —OC(O)NH—, or —NHC(O)O—;
each a' is independently an integer from 0 to 12;
each b is independently an integer from 0 to 12;
each c is independently an integer from 0 to 25;
each d is independently an integer from 0 to 12;
with the proviso that neither X nor Q is —O—O—, —NH—O—, nor —NH—NH—; and
q is an integer from 3 to about 50.

2. The compound of claim 1, wherein POLY is a poly(alkylene oxide).

3. The compound of claim 2, wherein the poly(alkylene oxide) is a poly(ethylene oxide).

4. The compound of claim 1, wherein the water-soluble, non-peptidic polymer has a molecular weight of greater than 2,000 Daltons.

5. A composition comprising a compound of claim 1, and optionally, a pharmaceutically acceptable excipient.

6. A composition of matter comprising a compound of claim 1, wherein the compound is present in a dosage form.

7. A method comprising administering to a mammal a compound of claim 1.

8. The compound of claim 1, wherein $R^4$ is —H, —F, —Cl, —Br, —I, —$CF_3$, —$CF_2H$, —$CFH_2$, —$CH_3$, —$OCH_3$, —$OCH_2CF_3$, —OH, —CN, —$NO_2$, —C(O)$CH_3$, —C(O)O$CH_3$, —C(O)NH—$CH_3$, —C(O)N($CH_3$)$_2$, —OC(O)$CH_3$, or —NH—C(O)$CH_3$.

9. The compound of claim 8, wherein $R^4$ is —$CF_3$.

10. The compound of claim 1, wherein a is 1.

11. The compound of claim 1, wherein $R^5$ is methyl.

12. The compound of claim 1, wherein Q is a hydrolytically stable linker.

13. The compound of claim 1, wherein X is spacer moiety that includes a releasable linkage.

14. The compound of claim 13, wherein the releasable linkage is a hydrolysable linkage.

15. The compound of claim 13, wherein the releasable linkage is an enzymatically degradable linkage.

16. The compound of claim 1, wherein R is a residue of a polyol bearing from 3 to 6 hydroxyl groups.

17. The compound of claim 1, wherein R is a residue of pentaerythritol.

18. A compound according to Formula III:

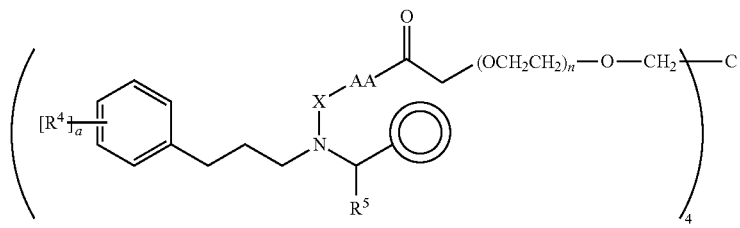

(Formula III)

or a pharmaceutically acceptable salt or solvate thereof, wherein:

n is an integer from 10 to about 500;

◎ is 3-methoxyphenyl, 3-chlorophenyl or 1-naphthyl;

each $R^4$ is independently —H, —F, —Cl, —Br, —I, phenyl, —$CF_3$, —$CF_2H$, —$CFH_2$, lower alkyl, —O-lower alkyl, —$OCH_2CF_3$, —OH, —CN, —C(O)-lower alkyl, —C(O)NH-lower alkyl, —C(O)N-(lower alkyl)$_2$, —OC(O)-lower alkyl, or —NH—C(O)-lower alkyl;

a is an integer from 1 to 5;

$R^5$ is lower alkyl;

X is —$(CR_xR_y)_{a'}$—$K_w$—$(CR_xR_y)_b$—$(CH_2CH_2O)_c$—$(CR_xR_y)_d$—$K_z$—, an amino acid residue, or combination thereof;

each of $R_x$ and $R_y$, in each occurrence, is independently H, alkyl, substituted alkyl, alkenyl, substituted alkenyl, alkynyl, substituted alkynyl, aryl or substituted aryl;

each of $K_w$ and $K_z$ is independently —NH—, —C(O)—, —C(O)NH—, —NHC(O)—, —O—, —S—, —OC(O)—, —C(O)O—, —OC(O)O—, —OC(O)NH—, or —NHC(O)O—;

each a' is independently an integer from 0 to 12;

each b is independently an integer from 0 to 12;

each c is independently an integer from 0 to 25;

each d is independently an integer from 0 to 12;

with the proviso that X is not —O—O—, —NH—O—, or —NH—NH—; and

AA is an amino acid residue.

19. The compound of claim 18, according to Formula IV:

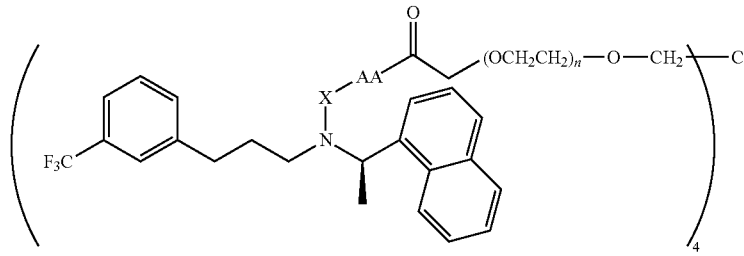

(Formula IV)

or a pharmaceutically acceptable salt or solvate thereof.

20. The compound of claim 18, according to Formula V:
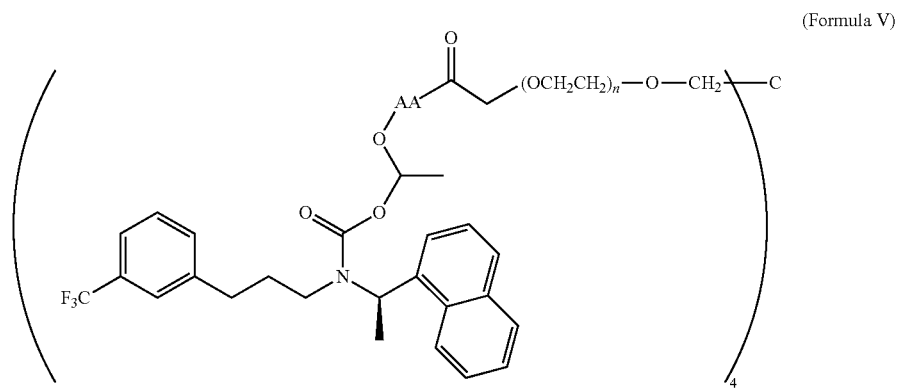
(Formula V)
or a pharmaceutically acceptable salt or solvate thereof.
\* \* \* \* \*